United States Patent [19]

Grudzinskas et al.

[11] 4,241,221

[45] * Dec. 23, 1980

[54] NOVEL 11-DEOXY-SUBSTITUTED PROSTAGLANDINS OF THE E AND F SERIES

[75] Inventors: Charles V. Grudzinskas, Garnerville, N.Y.; Martin J. Weiss, Oradell, N.J.

[73] Assignee: American Cyanamid Company, Stamford, Conn.

[*] Notice: The portion of the term of this patent subsequent to Nov. 8, 1994, has been disclaimed.

[21] Appl. No.: 776,444

[22] Filed: Mar. 10, 1977

Related U.S. Application Data

[63] Continuation of Ser. No. 552,403, Feb. 24, 1977, Pat. No. 4,057,571, which is a continuation-in-part of Ser. No. 274,559, Jul. 24, 1972, Pat. No. 4,141,914.

[51] Int. Cl.$^3$ .............................................. C07C 177/00
[52] U.S. Cl. ..................................... 562/470; 560/21; 560/60; 562/435
[58] Field of Search ............................. 560/53, 21, 60; 562/565, 70

[56] References Cited

U.S. PATENT DOCUMENTS

| | | | |
|---|---|---|---|
| 3,919,302 | 11/1975 | Strike et al. | 260/514 |
| 4,057,571 | 11/1977 | Grudzinskas et al. | 560/121 |

FOREIGN PATENT DOCUMENTS

2193613  2/1974  France ...................... 260/514

OTHER PUBLICATIONS

Samuelsson, Advances in Prostaglandin and Thromboxane Research, pp. 483–490 (1977).

*Primary Examiner*—Robert Gerstl
*Attorney, Agent, or Firm*—Richard J. Hammond

[57] ABSTRACT

This disclosure describes 11-deoxy-11-substituted members of the $E_2$, $F_2$, $E_1$, $F_1$, dihydro $E_1$ and dihydro $F_1$ prostaglandin series which are useful as hypotensive agents and as anti-ulcer agents.

13 Claims, No Drawings

NOVEL 11-DEOXY-SUBSTITUTED PROSTAGLANDINS OF THE E AND F SERIES

CROSS REFERENCE TO RELATED APPLICATION

This is a continuation of application Ser. No. 552,403 filed Feb. 24, 1977, now U.S. Pat. No. 4,057,571, which is a continuation-in-part of our copending application Ser. No. 274,559, filed July 24, 1972 now U.S. Pat. No. 4,141,914.

DETAILED DESCRIPTION OF THE INVENTION

This invention relates to novel organic compounds of the prostanoic acid class and their derivatives. In particular, the compounds of this invention are 11-deoxy-11-substituted derivatives of this class. The novel compounds of this invention embrace all of the optical antipodes, enantiomers, diastereoisomers, racemates, racemic mixtures and diastereoisomeric mixtures represented by the following general formulae; of which (A) represents the absolute configuration of the mammalian, naturally-occurring prostaglandins.

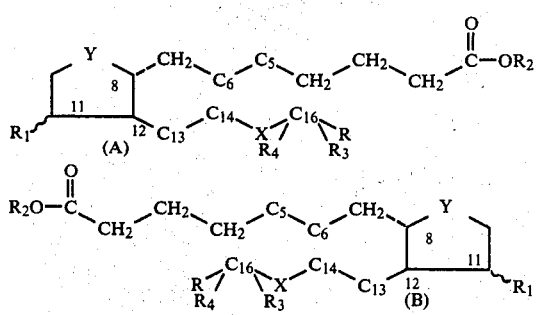

wherein R is a member of the group consisting of alkyl groups of 3 to 7 carbon atoms, alkenyl groups of 3 to 7 carbon atoms, phenyl, and phenoxy-unsubstituted or substituted with one or two groups selected from the group consisting of lower alkyl, lower alkoxy, nitro, halogen and trifluoromethyl; $R_1$ is a member of the group consisting of lower alkyl, lower 1-alkenyl, phenyl, lower alkylthio, lower alkanoylthio, sulfhydryl, ω-di(lower alkyl)amino lower alkylthio, cyano, carboxamido, carboxylic acid and alkyl esters thereof, α-nitro lower alkyl, α,α-di(lower carboalkoxy) lower alkyl, α,α-dicarboxy lower alkyl, α-carboxy lower alkyl, di(-lower alkyl)sulfonium halide, p-toluenesulfonylate or lower alkylsulfonate, formyl, lower alkanoyl, α,α-di(-lower alkoxy)methyl, α,α-ethylenedioxy lower alkyl, α-hydroxy-lower alkyl radicals; $R_2$ is selected from the group consisting of hydrogen and an alkyl group having from 1 to 12 carbon atoms; $R_3$ and $R_4$ are members of the group consisting of hydrogen, fluorine and lower alkyl radicals, not necessarily the same for each use; X is a divalent moiety selected from the group consisting of

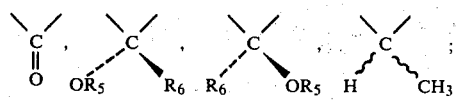

wherein $R_5$ is selected from the group consisting of hydrogen, lower alkanoyl, lower alkylsulfonyl, tetrahydropyranyl and tri(lower alkyl)silyl; $R_6$ is selected from the group consisting of hydrogen and lower alkyl radicals with the proviso that when $R_6$ is lower alkyl, then $R_5$ is hydrogen; Y is a divalent radical selected from the group consisting of:

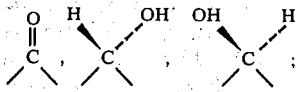

the moiety of -$C_5$-$C_6$- is ethylene or cis-vinylene; the moiety -$C_{13}$-$C_{14}$- is ethylene or trans-vinylene; with the proviso that when -$C_5$-$C_6$- is cis-vinylene, then -$C_{13}$-$C_{14}$- must be trans-vinylene; with the third proviso that the bonds represented as ∼∼∼ embrace both possible configurations; and with the further proviso that the three substituents at $C_8$, $C_{12}$ and $C_{11}$ of the cyclopentenone ring are not each cis to each other at the same time.

Suitable lower alkyl and lower alkanoyl groups contemplated by the present invention are those having up to four carbon atoms such as, for example, methyl, ethyl, isopropyl, sec-butyl, formyl, acetyl, propionyl, iso-butryl, etc.

Also embraced within the scope of the present invention are the non-toxic, pharmaceutically acceptable salts of the novel compounds of the present invention when $R_2$ is hydrogen. The cations comprised in these salts include, for example, the non-toxic metal cations such as the sodium ion, potassium ion, calcium ion, and magnesium ion as well as the organic amine cations such as the tri(lower alkyl)amine cations (e.g., triethylamine), procaine, and the like.

The novel compounds of the present invention are obtainable as yellow oils having characteristic absorption spectra. They are relatively insoluble in water but are relatively soluble in common organic solvents such as ethanol, ethyl acetate, dimethylformamide, and the like. The cationic salts of the compounds when $R_2$ is hydrogen are, in general, white to yellow crystalline solids having characteristic melting points and absorption spectra. They are relatively soluble in water, methanol, and ethanol but are relatively insoluble in benzene, diethyl ether, and petroleum ether.

The $C_{11}$ substituents of the compounds of this invention can be introduced by a conjugate addition reaction with $\Delta^{10}$-9-keto prostenoic acid and their derivatives, commonly referred to as prostaglandins of the A series, or by a subsequent transformation of an already present $C_{11}$-substituent.

A substituent at $C_{11}$ trans to the $C_{12}$ chain is said to be in the α configuration and its bond to $C_{11}$ is represented by ||||||. Conversely, a substituent at $C_{11}$ cis to the $C_{12}$ chain is in the β configuration (also termed 11-epi) and its bond to $C_{11}$ is represented by a solid line; a bond represented by a∼indicates that both the 11α and 11β possibilities are embraced. When the oxy substituent at $C_{15}$ is in the α or "normal" configuration, the bond is represented by |||| and when it is in the β or "epi" configuration the bond is indicated by—▪.

Among the reagents which can be utilized for conjugate addition are lithio di(lower alkyl)cuprates (e.g. lithio dimethylcuprate), lithio di(lower 1-alkenyl)cuprates, lithio diphenyl cuprate, lower alkyl mercaptans, ω-di(lower alkyl)amino lower alkyl mercaptans, thio lower alkanoic acids, acetone cyanohydrin (for cyanide introduction), 1-nitro-lower alkanes, di(lower alkyl)malonates as well as di(lower alkyl)mono-lower alkyl substituted malonates, lower primary and secondary alcohols, 1,3-dioxolan and lower 2-alkyl 1,3-dioxolans. With the exception of the lithio di(lower alkyl)cuprates and lithio di(lower alkenyl)cuprates, the various reagents generally require catalytic conditions for effective conjugate addition. The appropriate conditions for each reagent are apparent from the examples included herein. Illustrative conjugate addition reacts using the naturally occurring 1-15-O-acetylprostaglandin-A$_2$ methyl ester (I) are shown in Flowsheets A through G, wherein R$_7$ is a lower alkyl group, lower 1-alkenyl group, or phenyl, R$_8$ is a lower alkanoyl group, R$_9$ is hydrogen or a lower alkyl group, R$_{10}$ is a lower alkyl group, and X is halogen, p-toluenesulfonyloxy, or lower alkylsulfonyloxy.

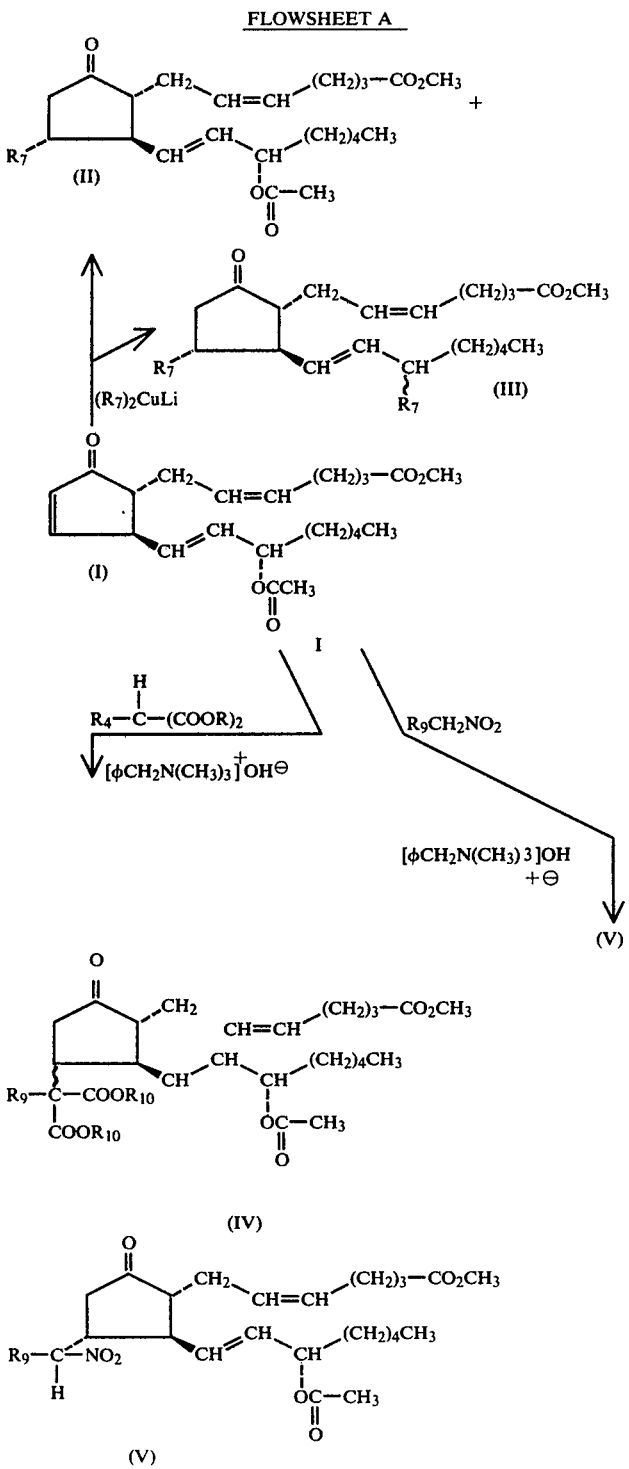

FLOWSHEET A

FLOWSHEET B
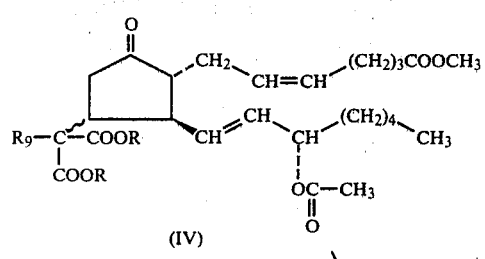
(IV)
↓
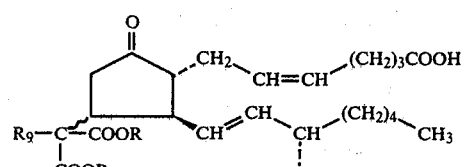
(VI)
↓
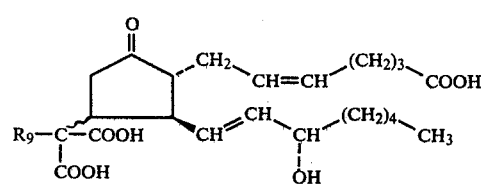
(VII)
↓
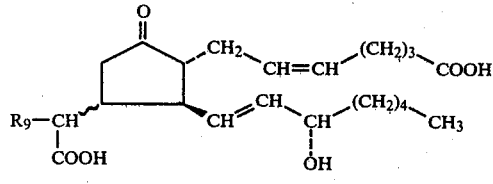
(VIII)
FLOWSHEET C
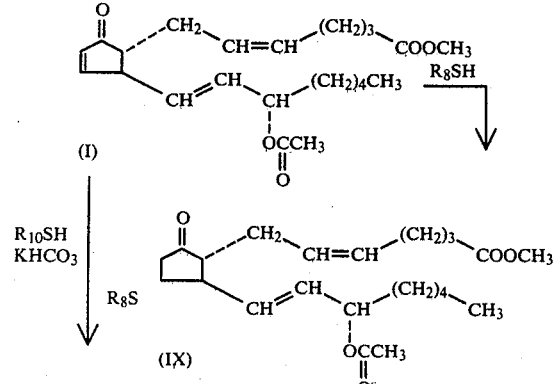
FLOWSHEET C
-continued
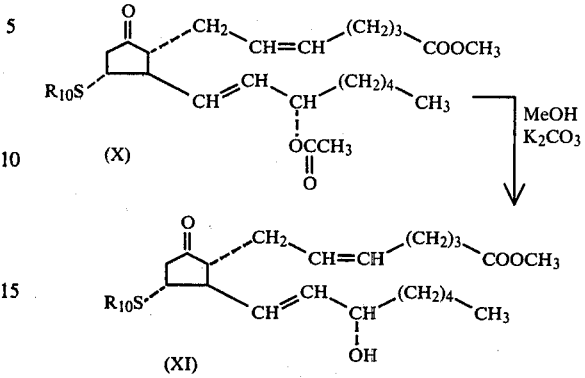
FLOWSHEET D
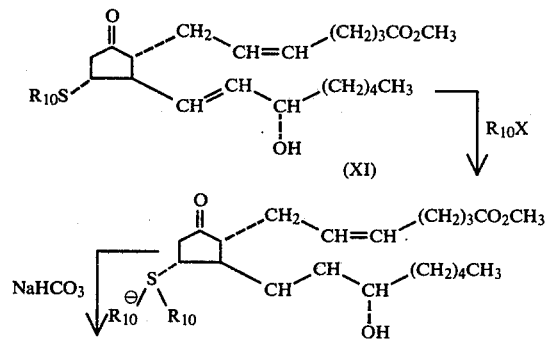
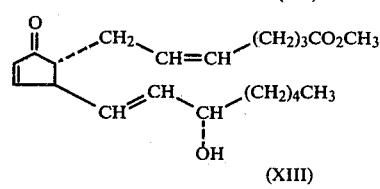
(XIII)
FLOWSHEET E
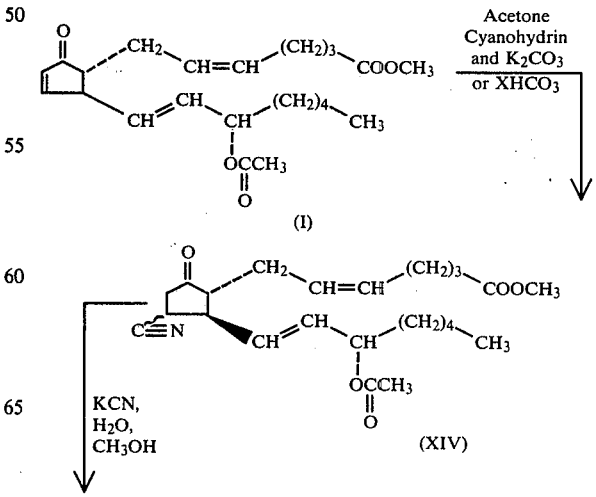

-continued
FLOWSHEET E
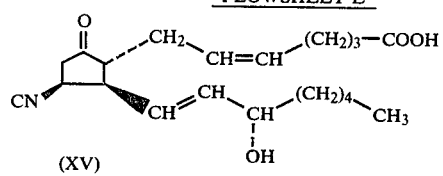
(XV)
+
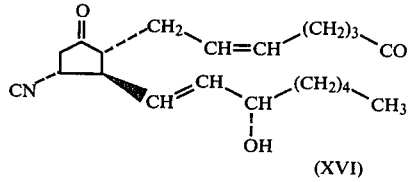
(XVI)
-continued
FLOWSHEET F
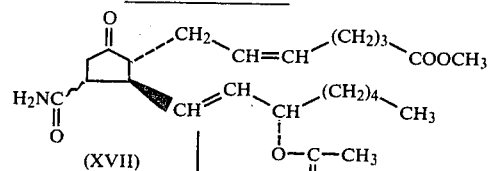
(XVII)
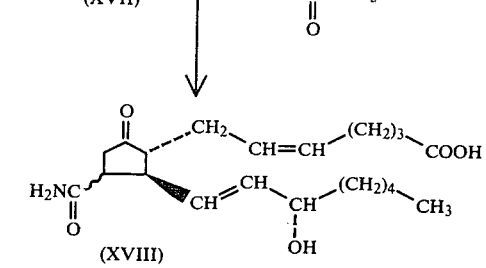
(XVIII)
FLOWSHEET F
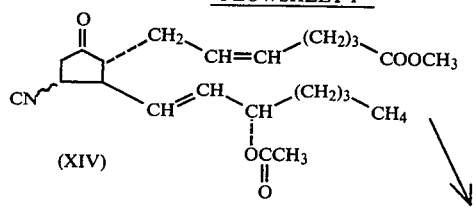
(XIV)
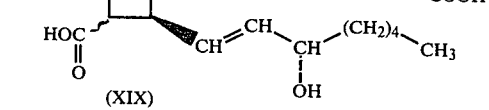
(XIX)
FLOWSHEET G
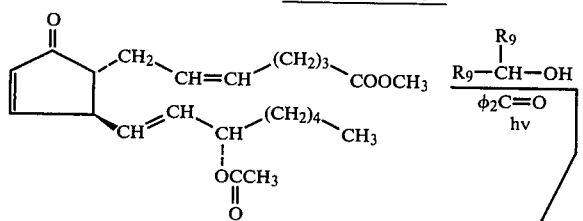
(I)
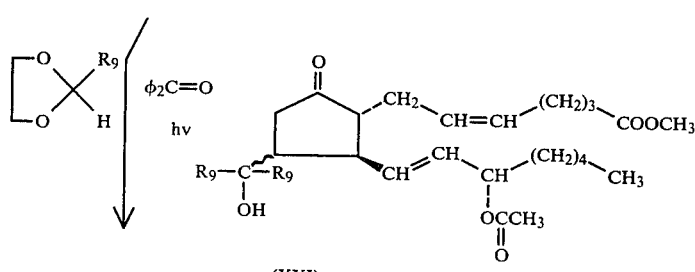
(XXI)
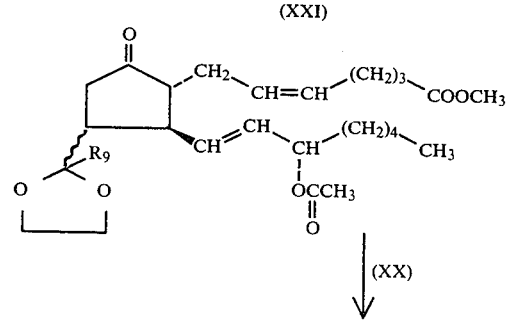
(XX)

FLOWSHEET G

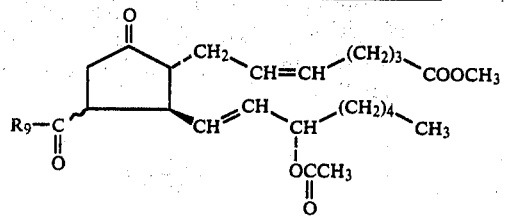

(XXII)

In accordance with Flowsheet A, treatment of 15-O-acetylprostaglandin-$A_2$ methyl ester with a lithio-dialkyl, dialkenyl or diphenylcuprate provides a mixture of the 11-deoxy-11-substituted-15-O-acetylprostaglandin-$E_2$ methyl ester and the 11-deoxy-11-substituted-15-substituted-prostaglandin-$E_2$ methyl ester. The use of the 15-hydroxy function to prevent the interaction of the 15-acetoxy group is described hereinbelow. Also in accordance with Flowsheet A is shown the conjugate addition of α,α-dicarboxylower alkyl and α-nitro lower alkyl groups.

The preparation of 11-deoxy-11-lower alkanoylthio-15-O-acetylprostaglandin-$E_2$ methyl esters by the heating of I in a thiolcarboxylic acid is illustrated in Flowsheet C. Also illustrated is the preparation of the 11-deoxy-11α-lower alkylthio-15-O-acetylprostaglandin-$E_2$ methyl ester (X) and its subsequent methanolysis to give XI.

The utility of XI to prepare $PGA_2$ methyl ester (XIII) is shown in Flowsheet D; (XIII) is not directly obtainable from I by the usual chemical procedures.

The preparation of the free 15-hydroxy derivative (XIII) from (I) is difficult to achieve directly by the usual acid-or-base-catalyzed conditions of hydrolysis. Under these circumstances (I) is too unstable and elimination to the novel tetraene (XXIII) is observed.

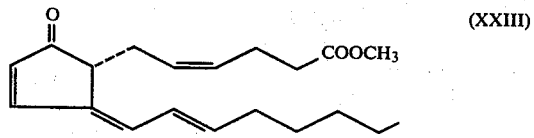

(XXIII)

In order to prepare the free 15-hydroxy derivative we have developed a convenient and novel procedure, which we consider to be a part of this invention. This procedure involves the conjugate addition to the diester of an alkyl/mercaptan (e.g., methyl mercaptan or ethyl mercaptan) to give the 11-alkylthio derivative (X). Saponification of diester (X) with potassium carbonate in the presence of excess alkyl mercaptan then procedes smoothly to provide the free 15-ol 11-alkylthio derivative (XI). The presence of alkyl mercaptan during this treatment presumably maintains the 11-alkylthio group, which otherwise would be eliminated under these conditions to give the $\Delta^{10}$-9-keto system, unstable to saponification conditions. Thus, in effect this procedure protects this latter system during saponification. The $\Delta^{10}$-function can then be regenerated under conditions to which it is stable by enhancing the leaving potential of the alkylthio group by conversion to a sulfonium salt (XII) which is eliminated readily with sodium bicarbonate to give the methyl ester (XIII) of $PGA_2$. The overall yield for the conversion of (I) to (XIII) is quite high, on the order of 70–85%, and several of the steps can be combined.

The free 15-ol (XIII) is a useful intermediate. For example, treatment with lithium dialkyl cuprates provides high yields of the 11-lower alkyl derivatives without involvement of the 15-oxy function. When the same reagent is used to treat the diester (I) the 15-acetoxy function becomes involved and a substantial portion of the product is the 11,15-di(lower alkyl) derivative (III).

As illustrated in the Flowsheet E, the treatment of the diester (I) with acetone cyanohydrin affords a mixture of 11α and 11β nitriles. Hydrolysis using saturated aqueous potassium cyanide in methanol yields the two epimeric nitriles (XV) and (XVI), separable by column chromatography (Example 212).

A unique photosensitized addition of lower primary and secondary alcohols, 1,3-dioxolan, and 2-substituted 1,3-dioxolans to the enone system of prostaglandins-A is also disclosed in this invention and is illustrated in Flowsheet G.

The irradiation of a solution of 15-O-acetylprostaglandin-$A_2$ methyl ester (I) in an alcohol containing benzophenone using a pyrex filter and medium pressure lamp provides the 11-deoxy-11-substituted-15-O-acetylprostaglandin-$E_2$ methyl ester (XXI). Likewise irradiation using 1,3-dioxolans as solvent yields 11-deoxy-11α-(1,3-dioxolan-2-yl)-15-O-acetylprostaglandin-$E_2$ methyl ester derivatives (XX); acid hydrolysis of which provides the corresponding 11-formyl or acyl derivatives.

Other novel compounds embraced by this invention can be prepared by further transformations of the above-described conjugate addition products. Thus, for example, hydrolysis of the malonate addition product (VI) furnishes the 11-(α,α-dicarboxy lower alkyl) derivative (VII), decarboxylation of which provides the 11-(α-carboxy lower alkyl) derivative (VIII). Treatment of the 11-cyano derivative (XIV), with alkaline hydrogen peroxide gives the 11-caboxamido diester (XVII), which on mild hydrolysis (three equivalents of potassium hydroxide, three hours, ambient temperature) gives the corresponding 15-hydroxy carboxylic acid (XVIII). Vigorous alkaline hydrolysis of (XVIII) then yields the 11-carboxylic acid derivatives (XIX).

Certain of the other products embraced by this invention can be obtained by substituting members from the following Table of prostaglandins A for l-15-O-acetylprostaglandin-$A_2$ methyl ester (I) or the corresponding free 15-ol (XIII) of Flowsheets A through G:

TABLE I l-13-dihydroprostaglandin-$A_1$[a]
l-prostaglandin-$A_1$[a]
l-prostaglandin-$A_2$[b]
l-15-epi-O-acetylprostaglandin-$A_2$ methyl ester[c]
l-15-epi-prostaglandin-$A_2$[c]
dl-prostaglandin-$A_1$[d]

TABLE I-continued l-15-methylprostaglandin-A$_1$ methyl ester[e]
d-15-methylprostaglandin-A$_2$ methyl ester[e]
l-16,16-dimethylprostaglandin-A$_1$[f]
l-16(S)-methylprostagladin-A$_2$[g]
l-16(R)-methylprostaglandin-A$_2$[g]
l-16(S)-methylprostaglandin-A$_1$[g]
l-16(R)-methylprostaglandin-A$_1$[g]
l-16,16-difluoroprostaglandin-A$_2$[h]
l-16-fluoroprostaglandin-A$_2$[h]
l-20-methylprostaglandin-A$_2$ (Example 108)
l-20-ethylprostaglandin-A$_2$ (Example 103)
d,l-17,20-tetranor-16-p-fluorophenoxyprostaglandin-A$_2$ (Example 113)
l-17,20-tetranor-16-p-fluorophenoxyprostaglandin-A$_2$ (Example 106)
d,l-17,20-tetranor-16-m-chlorophenoxyprostaglandin-A$_2$ (Example 111)
l-17,20-tetranor-16-m-chlorophenoxyprostaglandin-A$_2$ (Example 104)
d,l-17,20-tetranor-16-m-trifluoromethylphenoxyprostaglandin-A$_2$ (Example 114)
l-17,20-tetranor-16-m-trifluoromethylphenoxyprostaglandin-A$_2$ (Example 107)
l-17,20-tetranor-16-phenoxyprostaglandin-A$_2$ (Example 105)
d,l-17,20-tetranor-16-phenoxyprostaglandin-A$_2$ (Example 112)

REFERENCES
[a]F.H. Lincoln et al., Journ. Org. Chem., 38, 956 (1973).
[b]W.P. Schneider, R.D. Hamilton, L.E. Rhuland, Journ. Amer. Chem. Soc., 94 2122 (1972).
[c]R.L. Spraggins and A. Weinheimer, Tetrahedron Letters, 5185, (1969).
[d]E.J. Corey et al., Journ. Amer. Chem. Soc., 90, 2246 (1968).
[e]G.L. Bundy et al., Advances in the Biosciences, 9, International Conference on Prostaglandins, 128 (1972).
[f]Belgium Patent No. 782,822.
[g]M. Hayashi et al., Journ. Org. Chem., 38 1250 (1973).
[h]Netherlands Patent No. 7,305,817.

The configuration of the various substituents introduced at C-11 has been established for nearly all of the compounds disclosed herein.

In the case of the 11-alkylthio derivatives, a single isomer (11α) almost totally predominates although traces of the 11β epimer are detected. In the 11-alkyl and 11-alkenyl series the available evidence indicates that a single isomer predominates. The evidence and theoretical considerations leads to the assignment to these epimers of the 11-normal configuration, i.e., a trans-relationship between the 11-substituent and the adjacent side chain.

The introduction of the 11-cyano moiety appears to yield mearly equal amounts of both the 11α and 11β epimers. This epimeric mixture is obtained when one uses either a diester such as l-15-O-acetylprostaglandin-A$_2$ methyl ester or a free hydroxy acid such as l-PGA$_2$. These epimers are separable from each other by chromatographic procedures.

The stereochemistry of the 11-hydroxy-lower alkyl derivatives is dependent upon the alcoholic reagent utilized. Methanol leads to a separable epimeric mixture of 11α-hydroxymethyl and 11β-hydroxymethyl epimers in about a 1:3 ratio, respectively. With isopropanol the product is largely the 11α-(1-hydroxy-1-methylethyl) derivative.

The photoesensitized introduction of 1,3-dioxolan yields a separable mixture of 11α and 11β-(1,3-dioxolan-2-yl) derivatives in a 1:3 ratio.

The 11α-substituted products of this invention can be epimerized to a mixture containing the 8-normal and 8-iso epimers. This is illustrated in Flowsheet H using 11-deoxy-11α-hydroxymethylprostaglandin-E$_2$ as an example.

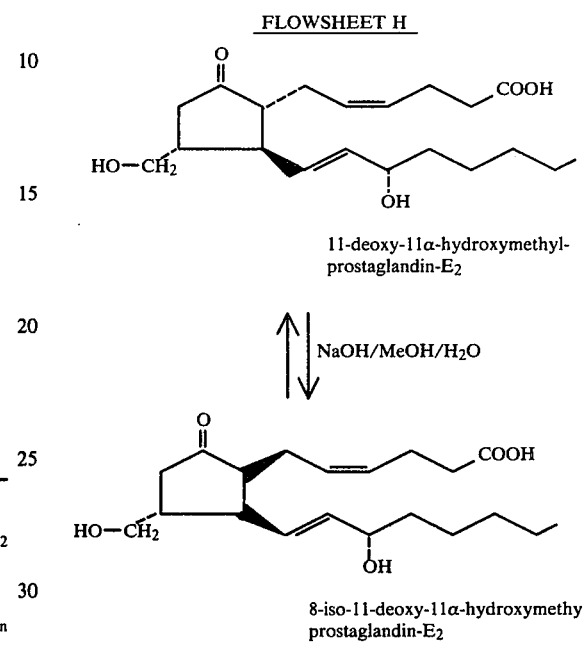

FLOWSHEET H 11-deoxy-11α-hydroxymethyl-prostaglandin-E$_2$

NaOH/MeOH/H$_2$O 8-iso-11-deoxy-11α-hydroxymethyl-prostaglandin-E$_2$

Esterification of the free 15-hydroxy function as well as of the free carboxylic acid function by the usual procedures provides the other ester derivatives of this invention.

The products of this invention that have the 15-oxy function in the (S) or "normal" configuration can be converted to the alternate (R) or "epi" configuration by two procedures, illustrated below in Flowsheet I for the 11-methyl series.

Treatment of (XXV) with a solution of sodium formate in formic acid induces racemization of the 15-oxy function and a mixture of the 15(R) and 15(S) formyloxy derivatives (XXIII) and (XXIV) are obtained. Separation of this mixture by chromatography provides the individual components and formate hydrolysis gives the original 15(S)-ol (XXV) and the inverted 15(R)-ol (XXVIII).

Epimerization of the 15(S)-ol (XXV) can be accomplished by conversion to a sulfonyloxy derivative (XXVI), such as methanesulfonyloxy, by treatment with methanesulfonic acid anhydride at low temperatures in the presence of an organic base such as triethylamine. The sulfonyloxy derivative (XXVI) is then treated with tetraethyl ammonium formate in a suitable organic solvent to produce the inverted 15(R)-formyloxy derivative (XXIV). Formate hydrolysis then provides the 15(R)-alcohol (XXVIII).

Likewise, compounds of this invention that contain the 15(R)-hydroxy function can be epimerized to either the 15(S) or a mixture of 15(S) and 15(R) derivatives.

FLOWSHEET I

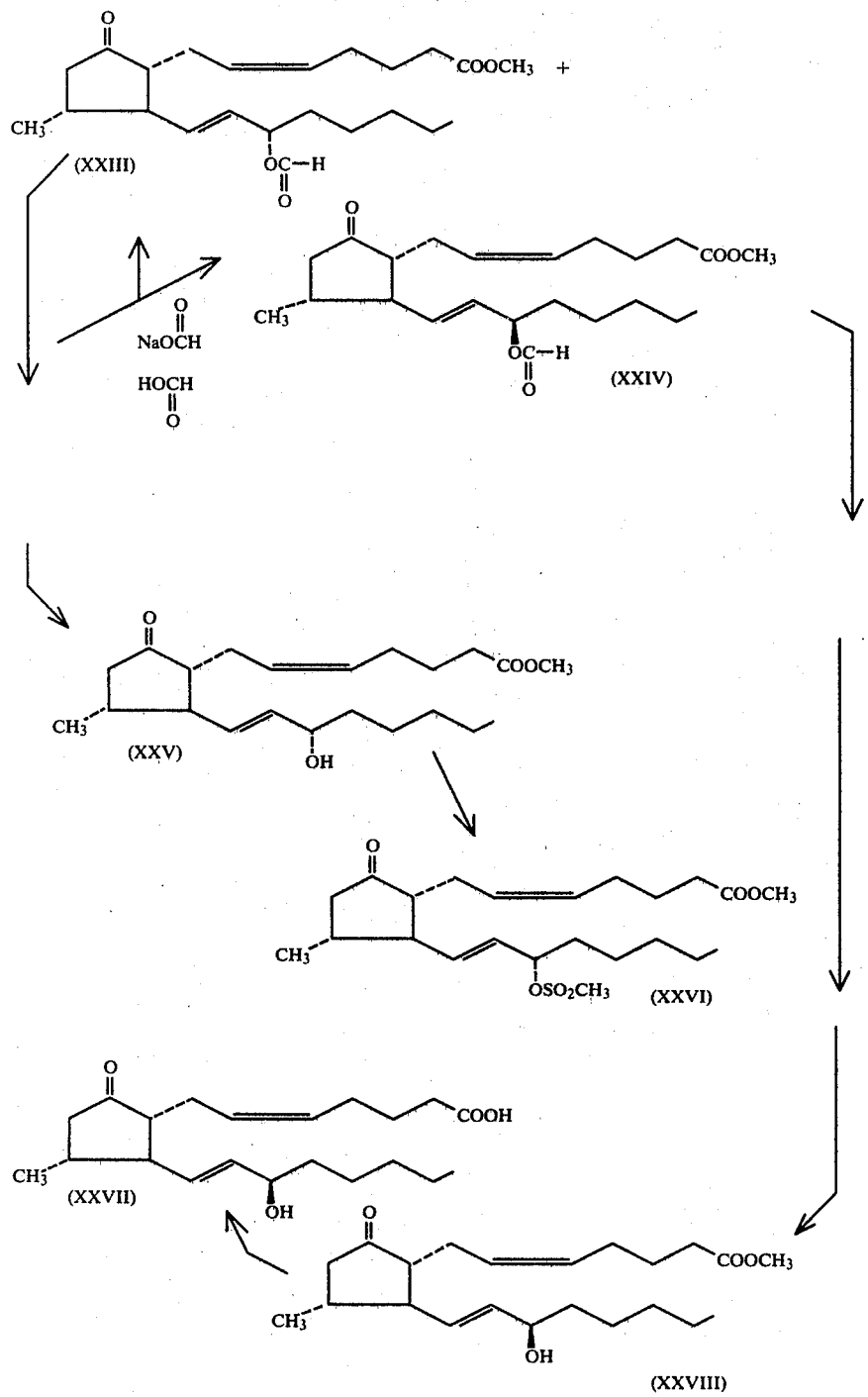

The 9-oxo derivatives (E-series) of this invention can be converted to the corresponding 9-hydroxy derivatives (F-series) by either a non-selective carbonyl reduction with a reagent such as sodium borohydride in an alcohol solvent, or stereoselectively with a reagent such as lithium-9b-boraphenalyl hydride (XXIX) [H. C. Brown and W. C. Dickason, Journ. Amer. Chem. Soc. 92, 709 (1970)] or lithium tri-sec-butylborohydride (XXX) in an ether solvent [H. C. Brown and S. Krishnamurthy, Journ. Amer. Chem. Soc., 94, 7159 (1972)].

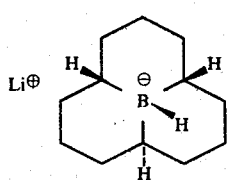

(XXIX)

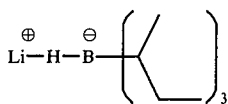

FLOWSHEET J

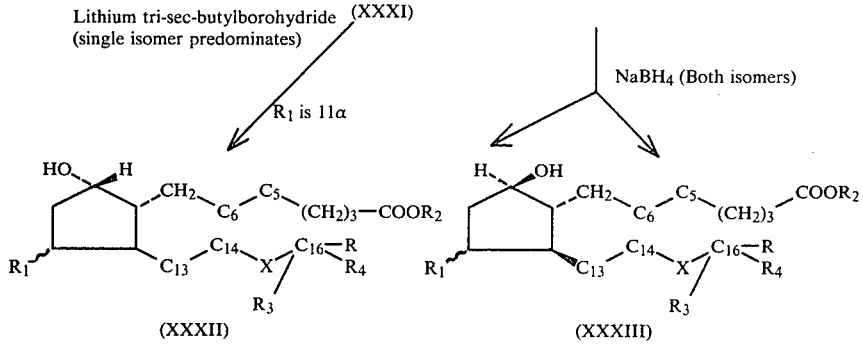

FLOWSHEET K

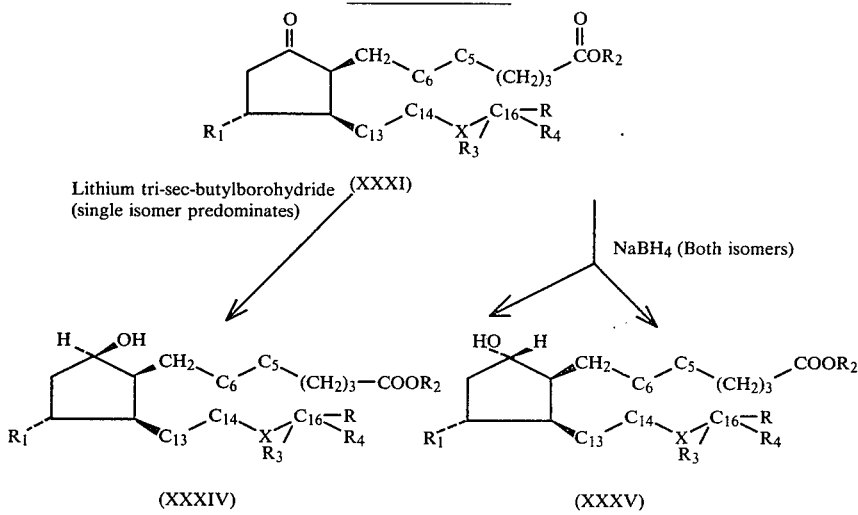

In accordance with Flowsheet J, treatment of the 9-keto derivative (XXXI) in a solvent such as ethanol with sodium borohydride will provide a mixture of the corresponding 9α and 9β hydroxy products which can be separated into their individual components by the usual chromatographic techniques. Stereoselectivity in this reduction can be realized by using a bulky reagent such as (XXIX) or (XXX) in a solvent such as tetrahydrofuran to provide, after borane hydrolysis, predominately, the cis-hydroxy (9α) species (XXXII) when the 11-substituent is in the α-configuration. In the particular case of compounds containing the 8-iso configuration (the two side chains being cis to each other) sodium borohydride again yields a mixture of 9α and 9β hydroxy compounds. However, the use of the bulky stereoselective reagents (XXIX) and (XXX) will yield predominantly the 9β hydroxyl, that is, the hydroxyl at the 9 position is cis to the carboxylic acid side chain. These reductions are illustrated in Flowsheet K.

The novel compounds of this invention which are members of the prostaglandin $E_2$ and $F_2$ series can be converted to other novel derivatives of the 11-deoxy prostaglandin $E_1$ and $F_1$ series by preferential reduction of the $\Delta^5$ cis-double bond. This can be achieved by careful catalytic hydrogenation in the presence of a metal catalyst such as palladium-carbon or RhCl [P(C$_6$H$_5$)$_3$]$_3$ or by use of diimide. Selectivity for the reduction of the $\Delta^5$ bond can be enhanced by first converting the 15-ol to a derivative which sterically hinders the approach to the competing $\Delta^{13}$ double bond. Useful 15-hydroxy derivatives for this purpose include the tetrahydropyranyl derivative and the dimethylisopropylsilyl ether.

This invention also includes the novel 11-substituted derivatives of 13-dihydro-11-deoxy-prostaglandin $E_1$ and $F_1$. These compounds, in which all of the double bonds are saturated, can be prepared by catalytic hydrogenation in the usual manner of the corresponding members of the $E_3$, $F_3$, $E_2$, $F_2$, $E_1$, or $F_1$ series. (F derivative of the 1 or dihydro-1 series can be prepared from the corresponding $F_2$ derivative by partial or full hydrogenation as just described or by reduction of the 9-carbonyl function of the corresponding E compound).

The compounds of this invention are useful as protective agents against the ulcerogenic and gastrointestinal effects induced by certain otherwise valuable pharmaceutical agents, particularly non-steroidal anti-inflammatory agents such as indomethacin, phenylbutazone, and aspirin. Indicative of the serious nature of this problem are the following statements concerning indomethacin (Indocin ®) taken from *Physician's Desk Reference* 1972 (Medical Economics Inc., Oradell, New Jersey), p. 964.

"Gastrointestinal Effects:

Because of the occurrence and, at times, severity of gastrointestinal reactions to INDOCIN, the prescribing physician must be continuously alert for any sign of symptom signalling a possible gastrointestinal reaction. The risks of continuing INDOCIN therapy in the face of such symptoms must be weighed against the possible benefits to the individual patient. The gastrointestinal effects may be reduced by giving the drug immediately after meals, with food, or with antacids. As advancing years appear to increase the possibility of adverse reactions, INDOCIN should be used with concomitantly greater care in the aging."

"Gastroinestinal Reactions:

Single or multiple ulcerations, including perforation and hemorrhage of the esophagus, stomach, duodenum or small intestines. Fatalities have been reported to occur in some instances. Gastrointestinal bleeding without obvious ulcer formation. Perforation of pre-existing sigmoid lesions (diverticulm, carcinoma, etc.). Increased abdominal pain in ulcerative colitis patients or the development of ulcerative colitis and regional ileitis have been reported to occur rarely. Gastritis may persist after the cessation of the drug. Nausea, vomiting, anorexia, epigastric distress, abdominal pain and diarrhea."

It is further to be noted that although prostaglandins in general are not effective when administered by oral route, the compounds of this invention are effective orally. The assay to determine the protective effect of these compounds is carried out in the following manner.

Rats were starved for 48 hours (water was given ad libitum). Indomethacin (20 mg./kg. of body weight) was administered by the subcutaneous route and one-half the dose of the test compound was administered by gavage at the same time. After three hours, the second half of the test compound was administered, also by gavage. Five hours after the administration of indomethacin the animals were decapitated and the stomachs removed. The stomachs were washed with distilled water, blotted on gauze, cut along the larger curvature, and the contents rinsed with distilled water. The stomachs were spread out, pinned on a cork and visualized under magnifying glass for ulcers. The criteria for scoring of ulcers was as previously reported. [Abdel-Galil et al. *Brit. J. Pharmac. Chemotherapy* 33:1-14 (1968)].

| Score | |
|---|---|
| 0 | Normal Stomach |
| 1 | Petechial hemorrhage of pin point ulcers |
| 2 | 1 or 2 small ulcers |
| 3 | Many ulcers, a few large |
| 4 | Many ulcers, mainly large |

Control animals treated with indomethacin but not test compound consistenly give scores of about 2.5–3.5. Control animals treated with neither indomethacin not test compound give scores of about 0.5–0.8. The results obtained in this assay with typical compounds of the present invention are set forth in the table below. Compounds diminishing the control ulcer score by 0.5 unit or more are considered to be active.

TABLE I

| Compound | Total oral dose; mg./kg. of body weight | SCORE Treated Animals | SCORE Controls |
|---|---|---|---|
| 1-11α/β-cyano-11-deoxyprostaglandin-$E_2$-methyl ester | 25 | 1.3 | 2.7 |
| 1-11α/β-cyano-11-deoxyprostaglandin-$E_2$ | 12.5 | 1.2 | 2.5 |
| 1-11α-nitromethyl-11-deoxyprostaglandin-$E_2$ | 100 | 1.0 | 3.2 |
| 1-11α-methylthio-11-deoxyprostaglandin-$E_2$ 15-O-acetate methyl ester | 50 | 2.0 | 2.7 |
| 1-11α-methyl-11-deoxyprostaglandin-$E_2$ | 6.25 | 2.5 | 3.0 |
|  | 12.5 | 2.0 | 3.0 |
|  | 25.0 | 1.7 | 3.0 |
| 1 11α-carboxamido-11-deoxyprostaglandin-$F_{2\alpha}$ | 50 | 2.3 | 3.2 |
| 1-11α-β-cyano-11-deoxyprostaglandin-$E_2$ 15-O-acetate methyl ester | 50 | 1.3 | 3.0 |
|  | 12.5 | 2.0 | 2.7 |
| 1-11α-methyl-11-deoxy-13-dihydroprostaglandin-$E_1$ | 50 | 1.7 | 3.0 |
|  | 12.5 | 2.3 | 3.0 |
| 1-11α-methyl-11-deoxyprostaglandin-$F_{2\alpha}$ | 25 | 1.8 | 2.7 |
| 1-11α,15-dimethyl-11,15-bisdeoxyprostaglandin-$E_{2\alpha}$ | 50 | 2.2 | 3.0 |
| 1-11α-cyano-11-deoxyprostaglandin-$F_{2\alpha}$ | 25 | 1.3 | 2.8 |
| 1-11α-ethyl-11-deoxyprostaglandin-$E_2$ | 25 | 2.2 | 3.0 |
| 1-11α-ethyl-11-deoxyprostaglandin-$F_{2\alpha}$ | 25 | 2.2 | 3.0 |
| 1-11α-phenyl-11-deoxyprostaglandin-$F_{2\alpha}$ | 25 | 2.0 | 3.9 |
| 1-11α-nitromethyl-11-deoxyprostaglandin-$F_{2\alpha}$ | 50 | 1.8 | 2.5 |
| 1-11α-methylthio-11-deoxyprostaglandin-$F_{2\alpha}$ | 12.5 | 1.2 | 2.7 |

The novel compounds of the present invention are effective inhibitors of gastric acid secretion and of ulcer development in experimental animals, and thus are potentially valuable as agents for the control of gastric secretion and of gastric erosion and as anti-ulcer agents. Gastric acid secretion inhibotory action is usually measured by the "Shay rat" procedure [1,2] with some modifications as follows.

(1) Shay et al., *Gastroenterology*, 5, 43 (1945).
(2) Shay et al., *Gastroenterology*, 5, 26, 906 (1954).

The rats (male, CFE strain) were starved for 48 hours (water was given ad libitum) to permit evacuation of stomach contents. On the morning of the experiment, under ether anesthesia, the abdominal region was shaved and a midline incision (1-½") was made with a scapel. With the help of a closed curved hemostat the duodenum was picked up. Upon getting the duodenum into view, fingers were used to pull the stomach through the opening, the stomach was then gently manipulated with fingers to rid stomach of air and residual matter which were pushed through the pylorus. Two-5 inch sutures were drawn under the pyloric-duodenal puncture. A ligature, at the juncture, was formed with one of the threads. The second ligature was also formed but not tightened.

The test compound or the vehicle, usually 1 ml./100 g. body weight, were injected into the duodenum as close as possible to the first ligature. After injection the second ligature was tightened below the injection site to minimize leakage. The stomach was placed back through the opening into the abdominal cavity, the area of incision was washed with saline and the incision was closed with autoclips. (Occasionally, instead of an intraduodenal injection, animals were dosed by the oral or subcutaneous route. In the latter case, dosing was done thirty to sixty minutes before the operation.)

Three hours later, the rats were decapitated and exanguinated, taking care that blood did not drain into the esohagus. The abdominal cavity was exposed by cutting with scissors and the esophagus close to the stomach was clamped off with a hemostat, the stomach was removed by cutting above the hemostat (the esophagus was cut) and between the two sutures. Extraneous tissue was removed, the stomach washed with saline and blotted on gauze. A slit was carefully made in the stomach which was held over a funnel and the contents were collected in a centrifuge tube. The stomach was further cut along the outside edge and turned inside out. Two ml. $H_2O$ were used to wash the stomach contents into the respective centrifuge tube. The combined stomach contents and wash were then centrifuged out for 10 minutes in the International Size 2 Centrifuge (setting at 30). The supernatant was collected, volume measured and recorded, 2 drops of a phenylphthalein indicator (1% in 95% ethanol) were added and the solution was titrated with 0.02 N NaOH (or with 0.04 N NaOH when large volumes of stomach contents were encountered) to pH 8.4 (because of usual coloring of the stomach contents, phenolphthalein was only used to permit visual indication that the end point was near) and the amount of acid present was calculated.

Compounds inducing inhibition of gastric acid secretion of 20% or more were considered active. In a representative operation, and merely by way of illustration, the results obtained with this assay with typical compounds of the present invention are given in Table II below.

TABLE II

| Compound | Intraduodenal dose, mg./kg. of body weight | Percent Inhibition |
|---|---|---|
| 1-11α/β-cyano-11-deoxyprostaglandin-$E_2$ 15-O-acetyl methyl ester | 25 | 51 |
| 1-11α/β-cyano-11-deoxyprostaglandin-$E_2$ methyl ester | 50 | 33 |
| 1-11α/β-cyano-11-deoxyprostaglandin-$E_2$ | 50 | 79 |
| | 25 | 31 |
| 1-11α-cyano-11-deoxyprostaglandin-$F_{2\alpha}$ | 50 | 43 |
| 1-11α-ethylthio-11-deoxyprostaglandin-$E_2$ 15-O-acetyl methyl ester | 50 | 27 |
| 1-11α-methylthio-11-deoxyprostglandin-$E_2$ 15-O-acetyl methyl ester | 50 | 35 |
| 1-11α-methyl-11-deoxyprostaglandin-$E_2$ | 50 | 63 |
| 1-11α-methyl-11-deoxyprostaglandin-$F_{2\alpha}$ | 50 | 70 |
| 1-11α-methyl-11-deoxy-13-dihydroprostaglandin-$E_1$ | 50 | 45 |
| 1-11α-methyl-11-deoxyprostaglandin-$E_2$ 15-O-acetyl methyl ester | 50 | 63 |
| 1-11α,15-dimethyl-11,15-bisdeoxyprostaglandin-$E_2$ methyl ester | 50 | 40 |
| 1-11α,15-dimethyl-11,15-bisdeoxyprostaglandin-$E_2$ | 50 | 60 |
| 1-11-carboxamido-11-deoxyprostaglandin-$E_2$ | 50 | 27 |
| 1-11-carboxamido-11-deoxyprostaglandin-$F_{2\alpha}$ | 50 | 27 |
| 1-11α-nitromethyl-11-deoxyprostaglandin-$E_2$ | 100 | 74 |
| 1-11α-vinyl-11-deoxyprostaglandin-$E_2$ | 50 | 59 |
| 1-11α-methylthio-11-deoxyprostaglandin-$E_2$ methyl ester | 100 | 55 |
| 1-11α-isopropyl-11-deoxyprostaglandin-$E_2$ | 50 | 42 |
| 1-11α-phenyl-11-deo deoxyprostaglandin-$E_2$ | 50 | 58 |
| 1-11α-(1-hydroxy-1-methylethyl)-11-deoxyprostaglandin-$E_2$ | 8* | 31 |
| 1-11α-hydroxymethyl-11-deoxyprostaglandin-$E_2$ | 8* | 44 |
| 1-11α-nitromethyl-11-deoxyprostaglandin-$F_{2\alpha}$ | 50 | 38 |
| 1-11α-methylthio-11-deoxyprostaglandin-$F_{2\alpha}$ | 50 | 61 |

*subcutaneous route of administration

Inhibition of basal gastric acid secretion can be determined by the following procedure.

Female Sprague-Dawley rats weighing 140–160 grams are fasted in individual cages for 18–24 hours. The rats are then lightly anesthetized with ether and their front teeth extracted to avoid destruction of the plastic cannula. A midline incision is then made and the stomach and duodenum exposed. A flanged polyvinyl tube is inserted into the fundic portion of the stomach and secured with a purse string suture line using 4-O Mersilene. The rat is then dosed by injection of the compound into the duodenum (1.0 ml. per 100 gram body weight). After dosing, the abdominal wall and skin are closed using metal wound clips. The rat is replaced in a cage containing a longitudinal slit to allow the polyvinyl tube to hang freely. An 8 ml. plastic collecting tube is attached to the flanged cannula and hangs freely below the cage. The first 30 minute sample is discarded designating this time as zero. The collecting tube is attached again and samples removed at the end of 60 and 120 minutes. These samples are referred to as "A" and "B" in the table. The hourly samples are then transferred to a 15 ml. centrifuge and centrifuged for 5-10 minutes. Total and sediment volume are then recorded with the supernatent volume being used as volume of secretion. A 1 ml. or less aliquot is then removed and placed in a 50 ml. beaker containing 10 ml. of distilled water. This sample is then titrated using 0.01 N NaPH to pH 7.0 using a Beckman zeromatic pH meter. Volume, titratable acidity (mew/L) and total acid output (ueq/hour) are recorded. Percent inhibition is determined by comparison with the appropriate control. Groups of three rats were used for preliminary testing, and groups of six rats were used for dose-response evaluations. All compounds are administered in a vehicle consisting of 0.5% methocel, 0.4% tween 80, and saline at a constant volume of 1 ml./100 gram rat. Samples are dispersed by sonification. Percent inhibition is calculated on basis of concurrent vehicle control.

In Table III which follows is given the effect on total acid output after 60 minutes and 120 minutes of intraduodenal dose, of representative compounds of this invention.

Female Sprague-Dawley rats (Charles River Laboratories) weighing less than 100 grams are fasted in individual cages for at least 18 hours. They are then anesthetized with ether and a midline incision made. The duodenum is exposed and the test drug or control injected intraduodenally. The ileocecal junction is then exposed and the terminal ileum is ligated using 3–0 silk thread just proximal to the junction. The incision is then closed using wound clips. Rats are placed back in individual cages without food or water for four hours. After this time the rats were sacrificed, the stomach and small intestine carefully removed, and cleaned of adherent mesentery. The removed portion of gut is then weighed to the nearest 0.1 gram. Compounds inducing diarrhea such as prostaglandins, cholera toxin, etc. produce an increase in weight of the ligated intestine. This increase from control is noted in Table IV, as change in weight in grams after standardizing weights of gut to grams/100 gram rat. An increase in intestinal weight of about 1.0 g. is considered indicative of diarrheagenic potential.

When measured by this assay at effective gastric acid secretion inhibiting doses, as determined by the acute rat fistula assay representative novel compounds of Table IV are non-diarrheagenic.

TABLE III

Inhibition of Total Acid Output in the Acute Gastric Fistula Rat

| Compound | Dose mg./kg. of body weight | % Inhibition of Total Acid Output After 60 minutes (A) | After 120 minutes (B) |
|---|---|---|---|
| l-11-acetylthio-11-deoxyprostaglandin-$E_2$ | 10 | 66 | 68 |
| l-11$\alpha$-ethylthio-15-O-acetyl-11-deoxy-prostaglandin-$E_2$ methyl ester | 10 | 80 | 24 |
|  | 5 | 19 | 59 |
|  | 2.5 | 54 | 51 |
| l-11$\alpha$-ethyl-11-deoxyprostaglandin-$E_2$ | 10 | 57 | 66 |
| l-11$\beta$-cyano-11-deoxyprostaglandin-$E_2$ | 10 | 26 | 43 |
| l-11$\alpha$-cyano-11-deoxyprostaglandin-$E_2$ | 10 | 49 | 18 |
| l-11-cyano-16-O-acetyl-11-deoxy-prostaglandin-$E_2$ methyl ester | 10 | 40 | 34 |
| l-11-carboxamido-11-deoxyprostaglandin-$E_2$ | 10 | 27 | 35 |
| l-11-mercapto-11-deoxyprostaglandin-$F_2\alpha$ | 10 | 44 | 55 |
| l-11$\beta$-hydroxymethyl-11-deoxyprostaglandin-$F_2\alpha$ | 10 | 0 | 43 |
| l-11$\alpha$-(1-hydroxy-1-methylethyl)-11-deoxy-prostaglandin-$F_2\alpha$ | 10 | 36 | 35 |
| l-11$\alpha$-vinyl-11-deoxyprostaglandin-$F_2\alpha$ | 5 | 53 | 67 |
|  | 2.5 | 15 | 37 |
| l-11$\alpha$-isopropyl-11-deoxyprostaglandin-$F_2\alpha$ | 10 | 44 | 35 |
| l-9$\alpha$-hydroxy-11$\alpha$,15-dimethyl-5-cis, 13-trans-prostadienoic acid | 10 | 25 | 20 |
| l-11$\alpha$-hydroxymethyl-11-deoxyprostaglandin-$F_2\beta$ | 5 | 49 | 49 |
| l-11$\alpha$-hydroxymethyl-15-O-acetyl-11-hydroxyprostaglandin-$F_2\beta$ methyl ester | 5 | 47 | 33 |

An important consideration in the use of prostaglandin like substances for the inhibition of gastric acid secretion and the treatment of ulcers, etc. is that they do not at the same time induce diarrhea, a common phenomenon observed on administration of the prostaglandins. It is therefore unexpected and novel that in general, the compounds of this invention are not diarrheagenic at dose levels at which they are effective gastric acid secretion inhibitors. One measure of diarrheagenic potential is the ileal ligated rat assay, a description of which follows directly.

TABLE IV

Ideal-Ligated Rat Assay

| Compound | Intraduodenal dose, mg./kg. of body weight | Increase in weight of intestine, g. |
|---|---|---|
| l-11-acetylthio-11-deoxyprostaglandin-$E_2$ | 20 | −0.1 |
|  | 10 | −0.02 |
| l-11$\alpha$-ethylthio-11-deoxyprostaglandin-$E_2$ | 10 | −0.2 |
| l-11$\alpha$-vinyl-11-deoxy-prostaglandin-$F_2\alpha$ | 10 | −0.36 |
| l-11$\alpha$-hydroxymethyl-11-deoxyprostaglandin-$F_2\beta$ | 10 | +0.6 |
| l-11$\alpha$-hydroxymethyl-15-O-acetyl-11-deoxy-prostaglandin-$F_2\beta$ | | |

TABLE IV-continued

Ideal-Ligated Rat Assay

| Compound | Intraduodenal dose, mg./kg. of body weight | Increase in weight of intestine, g. |
|---|---|---|
| methyl ester | 10 | +0.15 |

The E-type prostaglandin of this invention show bronchodilator activity in experimental animals and are potentially useful in the treatment of bronchial asthma.

Bronchodilator activity was determined in guinea pigs against bronchospasms elicited by intravenous injections of 5-hydroxytryptamine, histamine or acetylchlorine by the Konzeti procedure. [See J. Lulling, P. Lievens, F. El Sayed and J. Prignot, *Arzneimittel-Forschung*, 18, 995 (1968).]

In the Table which follows bronchodilator activity for representative compounds of this invention against one or more of the three spasmogenic agents is expressed as an $ED_{50}$ determined from the results obtained with three logarithmic cumulative intravenous doses.

TABLE V

Bronchodilator Activity (Konzett Assays) $ED_{50}$, mg./kg.

| Compound | Spasmogenic Agent | | |
|---|---|---|---|
| | 5-hydroxy-tryptamine | histamine | acetyl-choline |
| l-11α-methyl-11-deoxy-13-dihydro-prostaglandin-$E_1$ | | | 0.773 |
| l-11α-cyano-11-deoxyprostaglandin-$F_{2\alpha}$ | | 1.66 | |
| l-11-α-methyl-11-deoxyprostaglandin-$F_{2\alpha}$ | 0.038 | 0.013 | |
| l-11α-methyl-11-deoxyprostaglandin-$E_2$ | 0.0022 | 0.050 | 1.19 |
| l-11α,15-dimethyl-11,15-bis-deoxy-prostaglandin-$E_2$ | 18.1 | | |
| l-11α/β-cyano-11-deoxy-prostaglandin-$E_2$ | .0036 | 0.0054 | 0.091 |
| l-11α-vinyl-11-deoxyprostaglandin-$E_2$ | 1.20 | 1.30 | |
| l-11α-isopropyl-11-deoxyprosta-glandin-$E_2$ | 8.95 | | |
| l-11α-phenyl-11-deoxyprostaglandin-$E_2$ | .46 | | |
| l-11α-carboxamido-11-deoxyprosta-glandin-$E_2$ | 1.7 | 0.53 | |
| l-11α-carboxymethyl-11-deoxyprosta-glandin-$E_2$ | 5.5 | 3.4 | 4.6 |
| l-11α-dicarboxymethyl-11-deoxy-prostaglandin-$E_2$ | 3.3 | | |
| l-11α-nitromethyl-11-deoxyprosta-glandin-$E_2$ | | 1.4 | 1.7 |
| l-11α-cyano-11-deoxyprostaglandin-$F_{2\alpha}$ | 0.03 | 0.019 | 0.015 |
| l-11α-methylthio-11-deoxyprosta-glandin-$F_{2\alpha}$ | 2.63 | 1.6 | |
| l-11α-ethyl-11-deoxyprostaglandin-$E_2$ | | 1.24 | 3.9 |
| l-11β-hydroxymethyl-11-deoxyprosta-glandin-$E_2$ | 0.30 | 0.065 | 0.25 |
| l-11β-cyano-11-deoxyprostaglandin-$E_2$ | 3.1 | 54.9 | |
| l-11α-cyano-11-deoxyprostaglandin-$E_2$ | $0.30 \times 10^{-3}$ | $1.4 \times 10^{-3}$ | $5.3 \times 10^{-3}$ |

The novel compounds of the present invention also have potential utility as hypotensive agents, abortifacients, agents for the induction of labor, agents for the induction of menses, fertility-controlling agents, central nervous system regulatory agents, salt and water-retention regulatory agents, diuretics, and as inhibitors of platelet aggregation. Certain of the novel compounds of this invention possess utility as intermediates for the preparation of other of the novel compounds of this invention.

This invention will be described in greater detail in conjunction with the following specific examples.

EXAMPLE 1

Isolation of the methyl ester of 15-O-acetylprostaglandin $A_2$ from Plexaura Homomalla (esper)

Specimens of Plexaura Homomalla (esper) are collected in Puerto Rican waters, air dried and stored under a nitrogen atmosphere at 0° C. The cortex is removed, ground and extracted with isomeric hexanes. The organic solvent is evaporated in vacuo to afford a prostaglandin containing residue. The residue is dissolved in nitromethane and extracted with isomeric hexanes. The nitromethane solution is evaporated to give a residue that is approximately 50% by weight of the residue prior to the nitromethane treatment. This process, in addition to the removal of unwanted materials, (largely fatty esters), also has the benefit of selectively removing the sterols that have nearly the same rf index on silica gel as that of the methyl ester of 15-O-acetylprostaglandin $A_2$.

Purification of the residue via dry column chromatography using acid washed silica gel and 5% ethyl acetate as elutant yields the 15-O-acetyl-prostaglandin $A_2$ methyl ester and prostaglandin $A_2$ methyl ester. The combined yield of the two prostaglandins is 1-2%.

The configuration of the C-15 carbon is established by degradation with ozone followed by chromic acid oxidation to yield α-acetoxyheptanoic acid. The configuration of the acetoxy grouping is established by comparison of the circular dichromism curves of α-acetoxyheptanoic acid and D-α-acetoxypropanoic acid prepared from the calcium salt of D-lactic acid (R-configuration). Compounds of like configuration will display curves of the same sign. D-α-acetoxypropanoic acid displays a negative circular dichromism curve whereas the degradation product, α-acetoxyheptanoic acid gives a positive circular dichromism curve.

EXAMPLE 2

Preparation of 11-deoxy-11α-ethylthio-15-O-acetyl prostaglandin $E_2$ methyl ester—Method A To a solution of 7.23 gm. of the methyl ester of 15-O-acetyl-prostaglandin $A_2$ in a mixture of 15 ml. ethanethiol, 15 ml. of tetrahydrofuran and 15 ml. of methanol is added 1.8 ml. of aqueous 5% sodium bicarbonate. The solution is stirred for twenty minutes and is evaporated in vacuo at 30° C. to a paste. To the paste is added 25 ml. ether and 10 ml. of water. The ether is separated and washed with brine. The aqueous layer is extracted with ether and the ether is washed with brine and the ether extracts are combined, dried with magnesium sulfate, and evaporated in vacuo to afford 8.375 gm. of 11-deoxy-11α-ethylthio-prostaglandin $E_2$ methyl ester as an oil; λmax: 1740 $cm^{-1}$ (saturated ketone and esters), 1225 $cm^{-1}$ (acetate); $[\alpha]_D^{25} = -59.67°$ (C=0.481 chloroform).

EXAMPLE 3

Preparation of 11-deoxy-11α-methylthioprostaglandin $E_2$—Method B

A solution of prostaglandin $A_2$ is treated as in Example 2 except that one equivalent of sodium bicarbonate in water is added before the addition of a catalytical amount of 5% aqueous sodium bicarbonate. In addition, the solution is acidified with a sodium biphosphate buffer prior to the extraction with ether to yield 11-deoxy-11α-methylthioprostaglandin $E_2$ after evaporation in vacuo of the organic solvents.

EXAMPLE 4

Conversion of 15-O-acetylprostaglandin $A_2$ methyl ester to prostaglandin $A_2$ methyl ester To a 0° C. solution containing 12.15 gm. of 15-O-acetylprostaglandin $A_2$ methyl ester in 50 ml. of methanethiol and 100 ml. of methanol is added a small amount of potassium carbonate. The solution is stirred 30 minutes and 75 ml. of methanol and 8.55 gm. of potassium carbonate is added. The flask is tightly stoppered, secured with rubber bands and stirred at room temperature for two weeks. The solution is cooled to an ice bath and poured into 350 ml. of ether and 500 ml. of ice water. The aqueous layer is extracted with ether and the combined ether extracts are washed with brine and dried with magnesium sulfate. The ether is evaporated in vacuo and the residue is dissolved in 100 ml. of methanol and filtered through celite to remove stop-cock crease. The methanol is evaporated in vacuo to afford 11.67 gm. of crude 11-deoxy-11α-methylthioprostaglandin $A_2$ methyl ester as an oil.

To a solution of 11.67 gm. of crude 11-deoxy-11α-methylthioprostaglandin $A_2$ methyl ester in a solution of 60 ml. tetrahydrofuran, 30 ml. of methanol and 25 ml. of iodomethane is added 70 ml. of a 5% aqueous sodium bicarbonate solution. The resulting solution is stirred vigorously and heated under reflux for four hours to form 11-deoxy-11α-dimethylsulfonium iodide prostaglandin $A_2$ methyl ester which is decomposed in solution to afford prostaglandin $A_2$ methyl ester.

The solution is cooled and added to 200 ml. of ether and 100 ml. of water. The aqueous layer is extracted with ether and the ether extracted are combined, washed with brine, dried with magnesium sulfate and evaporated in vacuo to afford 10.63 gm. of the crude prostaglandin $A_2$ methyl ester as an oil.

The oil is purified by dry column chromatography using acid washed silica gel. The material in methylenechloride is placed onto a 62"×3" flat diameter nylon tube containing the acid washed silica. The column is developed with ether and is then cut up into 10 equal sections. Sections 6, 7 and 8 are combined and the product is eluted from the silica gel with 20% methanol in chloroform.

Evaporation in vacuo of the solvents affords 8.64 gm. (80%) of prostaglandin $A_2$ methyl ester; λmax 1735 $cm^{-1}$, 1710 $cm^{-1}$, 1660 $cm^{-1}$, 3400 $cm^{-1}$; $[\alpha]_D^{25} = +137.5$ (C=0.4, chloroform).

Elution of the material from sections 9 and 10 of the column in like fashion yields 1.2 gm. of the starting 15-O-acetyl prostaglandin methyl ester.

Substitution of ethanethiol for methanethiol in the above procedure results in the formation of 11-deoxy-11α-ethylthioprostaglandin $A_2$ methyl ester and 11-deoxy-11α-(ethyl methyl sulfonium iodide) prostaglandin $A_2$ methyl ester as intermediates in the preparation of prostaglandin $A_2$ methyl ester.

EXAMPLES 5–12

Treatment of the following A type prostaglandins with the following alkyl mercaptans in the manner of Example 2 (Method A) or Example 3 (Method B) is productive of the 11α-alkylthioprostaglandins (E type) of the table.

| Example | Starting Prostaglandin | Alkyl Mercaptan | Method | Product 11α-alkylthio-prostaglandin E |
|---|---|---|---|---|
| 5 | 15-O-acetyl prostaglandin $A_2$ methyl ester | ethanethiol | A | 11-deoxy-11α-ethylthioprostaglandin $E_2$ methyl ester |
| 6 | prostaglandin $A_2$ | methanethiol | B | 11-deoxy-11α-methylthioprostaglandin $E_2$ |
| 7 | prostaglandin $A_2$ | ethanethiol | B | 11-deoxy-11α-ethylthioprostaglandin $E_2$ |
| 8 | prostaglandin $A_2$ | 1-propanethiol | B | 11-deoxy-11α-isopropylthioprostaglandin $E_2$ |
| 9 | prostaglandin $A_1$ | methanethiol | B | 11-deoxy-11α-methylthioprostaglandin $E_1$ |
| 10 | prostaglandin $A_1$ | 1-butanethiol | B | 11-deoxy-11α-butylthioprostaglandin $E_1$ |
| 11 | 13,14-dihydroprostaglandin $A_1$ | methanethiol | B | 11-deoxy-11α-methylthio-13,14-dihydroprostaglandin $A_1$ |
| 12 | 13,14-dihydroprostaglandin $A_1$ | 1-propanethiol | B | 11-deoxy-11α-propylthio-13,14-dihydroprostaglandin $A_1$ |

EXAMPLE 13

Preparation of 11-deoxy-11α/β-15-O-acetylprostaglandin $E_2$ methyl ester

A solution of 5 g. of the methyl ester of 15-O-acetylprostaglandin $A_2$ in 10 ml. of thiolacetate acid is refluxed three hours. The solution is evaporated in vacuo at 45° C. and the residue is dissolved in benzene and the solution evaporated in vacuo to afford 5.18 g. of an oil.

Thin layer chromatography indicates two compounds (epimers at C-11); λmax 1735 cm$^{-1}$ (saturated carbonyls), 1700 cm$^{-1}$

EXAMPLES 14-16

Treatment of the following A type prostaglandins with thiolacetic acid by the procedure of Example 13 affords the 11-acetylthio E-type prostaglandins of the following table.

| Example | Starting Prostaglandin-A | Product 11-acetylthio-prostaglandin E |
|---|---|---|
| 14 | Prostaglandin A$_2$ | 11-deoxy-11α/β-acetylthioprostaglandin E$_2$ |
| 15 | Prostaglandin A$_1$ | 11-deoxy-11-60 /β-acetylthioprostaglandin E$_1$ |
| 16 | 13,14-dihydroprostaglandin A$_1$ | 11-deoxy-11α/β-acetylthio-13,14-dihydroprostaglandin E$_1$ |

EXAMPLE 17

Preparation of 11-deoxy-11α-methyl-15-deoxy-15-methylprostaglandin E$_2$ methyl ester To a solution, maintained at −10° C., of lithium dimethyl cuprate (4.87 g. cuprous iodide in 10 cc ether titrated with 2 M methyllithium until the solution is clear) is added dropwise a solution of 5.0 g. of the methyl ester of 15-O-acetyl-prostaglandin A$_2$ in 25 ml. of ether. The solution is stirred for 15 minutes and then is added to 200 ml. of saturated aqueous ammonium chloride. The aqueous solution is extracted with ether. The ether extracts are combined, washed with brine, dried with anhydrous magnesium sulfate and evaporated in vacuo to yield 4.65 g. of an oil. The oil is purified by silica gel chromatography with 3% ethyl acetate/benene to afford 2.56 g. of the product as an oil; λmax 1740 cm$^{-1}$ (saturated carbonyls); $[\alpha]_D^{25}$ = −75.4° (C=0.5, chloroform) in addition is obtained 11-deoxy-11α-methyl-15-O-acetylprostaglandin A$_2$ methyl ester.

EXAMPLE 18

Preparation of 11-deoxy-11α-methyl-propstaglandin E$_2$ methyl ester

To a −20° C. solution of lithium dimethyl cuprate (prepared from 3.9 gm. cuprous iodide in ten ml. ether by titration with 1 M methyllithium until the resulting solution is clear) is added a solution of 3.36 g. of the methyl ester of prostaglandin A$_2$ (Example 4) in ten ml. of ether. The resulting solution is stirred forty-five minutes and then poured into 250 ml. of saturated ammonium chloride and stirred 15 minutes. The solution is extracted with ether and the ether extracts are combined, washed with brine, dried with anhydrous magnesium sulfate and evaporated in vacuo to afford 3.37 g. of an oil that is homogenous by thin layer chromatography; λmax 3400 cm$^{-1}$ (hydroxyl), 1740 (saturated carbonyls); $[\alpha]_D^{25}$ = −47.8° (C=0.5, chloroform).

EXAMPLE 19

Preparation of 11-deoxy-11α-vinylprostaglandin E$_2$ methyl ester

To a solution of (17.5 mM) lithium divinyl cuprate (prepared from 6.87 g. of the cuprous iodide-tributylphosphine complex and 17.5 ml. of 2 molar vinyllithium) in tetrahydrofuran at −78° C. is added a solution of 3 g. (8.65 mM) of prostaglandin A$_2$ methyl ester (Example 4) in 10 ml. of ether. The resulting viscous solution is diluted with 10 ml. of tetrahydrofuran and stirred at −78° C. for 60 minutes.

The solution is poured into 150 ml. of saturated aqueous ammonium chloride and stirred 1 hour at room temperature with 200 ml. of ether. The ether solution is separated and is extracted with water, washed with brine, dried with magnesium sulfate and evaporated in vacuo to yield 12.1 gm. of an oil.

The oil is triturated with methanol several times and the methanol washes are combined, filtered through celite and evaporated in vacuo to afford 5.9 g. of an oil; λmax: 3400 cm$^{-1}$ (hydroxyl), 1740 cm$^{-1}$ (saturated ketone and ester), 1635 cm$^{-1}$ (vinyl group); 970 cm$^{-1}$ (trans double bond), 920 cm$^{-1}$ (terminal vinyl).

EXAMPLES 20-28

Treatment of the A-type prostaglandin methyl esters listed in the table below with the indicated organolithium cuprates and by the indicated procedure is productive of the 11-alkyl or 11-alkenyl E-type prostaglandins of the table.

| Example | Cuprate Reagent | Method of Example | Starting Prostaglandin Ester | Product 11α-alkyl/alkenyl-11-deoxyprostaglandin-E |
|---|---|---|---|---|
| 20 | diethylcopperlithium | 18 | prostaglandin A$_2$ methyl ester | 11-deoxy-11α-ethylprostaglandin E$_2$ methyl ester |
| 21 | dipropylcopperlithium | 18 | prostaglandin A$_2$ methyl ester | 11-deoxy-11α-propylprostaglandin E$_2$ methyl ester |
| 22 | diisopropylcopperlithium | 18 | prostaglandin A$_2$ methyl ester | 11-deoxy-11α-isopropylprostaglandin E$_2$ methyl ester |
| 23 | dipropenylcopperlithium | 19 | prostaglandin A$_2$ methyl ester | 11-deoxy-11α-propenylprostaglandin E$_2$ methyl ester |
| 24 | dimethylcopperlithium | 18 | prostaglandin A$_1$ methyl ester | 11-deoxy-11α-methylprostaglandin E$_1$ methyl ester |
| 25 | diethylcopperlithium | 18 ester | prostaglandin A$_1$ methyl ester | 11-deoxy-11α-ethylprostaglandin E$_1$ |
| 26 | divinylcopperlithium | 19 ester | prostaglandin A$_1$ methyl ester | 11-deoxy-11α-vinylprostaglandin E$_1$ |
| 27 | dipropenylcopperlithium | 19 | prostaglandin A$_1$ methyl ester | 11-deoxy-11α-propenylprostaglandin E$_1$ methyl ester |
| 28a | divinylcopperlithium | 19 | 13,14-dihydroprostaglandin A$_1$ methyl ester | 11-deoxy-11α-vinyl-13,14-dihydroprostaglandin E$_1$ methyl ester |

-continued

| Example | Cuprate Reagent | Method of Example | Starting Prostaglandin Ester | Product 11α-alkyl/alkenyl-11-deoxyprostaglandin-E |
|---|---|---|---|---|
| 28b | divinylcopperlithium | 19 | prostaglandin A₂ methyl ester | 11-deoxy-11α-vinylprostaglandin E₂ methyl ester |

EXAMPLE 29

Preparation of 11-deoxy-11α-methyl-13,14-dihydroprostaglandin $E_1$

To a suspension of 300 mg. of 5% rhodium-on-carbon in 10 ml. of ethylacetate is added a solution of 1.02 g. of 11-deoxy-11α-methylprostaglandin $E_2$ (Example 57) in 10 ml. ethylacetate. The resulting suspension is hydrogenated at 50 psi of hydrogen for 1 hour. The solution is filtered and the solvent is evaporated in vacuo to afford 1.04 g. of an oil. The oil is purified by dry column chromatography on a 29"×1½" flat diameter nylon tube filled with acid washed silica gel. The column is developed with ethyl acetate/benzene/acetic acid (10:40:1) and the section corresponding to rf=0.38-0.53 was eluted with 20% methanol in chloroform to afford 542 mg. of the product as an oil; λmax 3400 cm$^{-1}$ (carboxyl and hydroxyl), 1740-1710 cm$^{-1}$ (carboxyl and saturated ketone); $[\alpha]_D^{25} = -49.5$ (C=0.8, chloroform).

EXAMPLES 30-32

Treatment of the 11-deoxy-11-alkylprostaglandin $E_2$ methyl esters listed in the table below by the procedure of Example 29 yields the 11α-alkyl-11-deoxy-13,14-dihydro-prostaglandins $E_1$ of the table.

| Example | Starting Prostaglandin-$E_2$ | Product - 11α-alkyl-11-deoxy-13,14-dihydroprostaglandin-$E_1$ |
|---|---|---|
| 30 | 11-deoxy-11α-ethyl-prostaglandin $E_2$ | 11-deoxy-11α-ethyl-13,14-dihydroprostaglandin $E_1$ |
| 31 | 11-deoxy-11α-propyl-prostaglandin $E_2$ | 11-deoxy-11α-propyl-13,14-dihydroprostaglandin $E_1$ |
| 32 | 11-deoxy-11-isopropylprostaglandin $E_2$ | 11-deoxy-11α-isopropyl-13,14-dihydroprostaglandin $E_1$ |

EXAMPLE 33

Preparation of 11-deoxy-11α-dicarboethoxymethyl-15-O-acetyl-prostaglandin $E_2$ methyl ester To a solution of 97 mg. of the methyl ester of 15-O-acetyl-prostaglandin $A_2$ and 44 mg. of diethylmalonate in one ml. of tetrahydrofuran is added one drop of a 35% solution of benzyltrimethyl ammonium hydroxide in methanol. Two ml. of tetrahydrofuran is added and the solution is stirred overnight.

The solution is applied directly to a 2 mm silica-gel thin layer chromatography plate and developed with 20% ethyl acetate/benzene. The band corresponding to the product is scraped off of the plate and the product is isolated by elution off of the silica with 20% methanol/chloroform. The resulting solution is evaporated to afford 76 mg. of an oil; λmax 1740 cm$^{-1}$ (saturated carbonyls), 1225 cm$^{-1}$ (OAc), 1180 and 1020 cm$^{-1}$ (CO₂Et), $[\alpha]_D^{25} = -60.98°$ (C=0.305, chloroform).

EXAMPLE 34

Preparation of 11-deoxy-11α-(α,α-dicarboethoxy)methylprostaglandin $E_2$

To a solution of 11-deoxy-11α-(α,α-dicarboethoxy)-methyl-15-O-acetyl-prostaglandin $E_2$ methyl ester (Example 33) in methanol is added 2.2 equivalents of a 2.5 N aqueous sodium hydroxide solution. The resulting solution is stirred for 4 hours and then poured into water. Extraction of the aqueous solution with ether removes unreacted ester. The aqueous solution is acidified and extracted with ether. The ether solution is washed with brine, dried with magnesium sulfate and evaporated in vacuo to afford the product. Purification via dry column chromatography affords 11-deoxy-11α-(α,α-dicarboethoxy)methylprostaglandin $E_2$.

EXAMPLE 35

Preparation of 11-deoxy-11α-(α,α-dicarboxy)methylprostaglandin $E_2$

To the product derived from the treatment of 5.5 g. of 15-O-acetyl-prostaglandin $A_2$ methyl ester with diethylmalonate as per Example 33, in 25 ml. of tetrahydrofuran is added 30 ml. of 2.5 N aqueous sodium hydroxide. The solution is stirred overnight at room temperature, and is then heated at 80° C. for one hour. The cooled solution is poured into 50 cc ether and 100 cc water. The aqueous phase is separated and extracted with ether.

The aqueous phase is acidified with 6 N aqueous hydrochloric acid, saturated with sodium chloride and extracted with ether. The ether solution is dried with magnesium sulfate and evaporated in vacuo to afford 4.48 g. of nearly pure product; λmax 3400-2600 cm$^{-1}$ (carboxyl and hydroxyl groups), 1710-1750 cm$^{-1}$ (saturated ketone and carboxyls).

EXAMPLES 36-38

Treatment of the indicated A-type prostaglandins with the designated malonates by the procedure of Example 33 furnishes the products of the table.

| Example | Reagent Malonate | Starting Prostaglandin A | Product Prostaglandin E |
|---|---|---|---|
| 36 | α-methyldiethylmalonate | 15-O-acetylprostaglandin $A_2$ methyl ester | 11-deoxy-11α-(α,α-dicarboethoxy ethyl-15-O-acetyl-prostaglandin $E_2$ methyl ester |
| 37 | α-ethyldiethylmalonate | 15-O-acetylprostaglandin $A_2$ methyl ester | 11-deoxy-11α-(α,α-dicarboethoxy propyl-15-O-acetyl-prostaglandin $E_2$ methyl ester |
| 38 | diethylmalonate | prostaglandin $A_1$ methyl ester | 11-deoxy-11α-(α,α-dicarboethoxy methylprostaglandin $E_1$ methyl ester |

EXAMPLE 39

Preparation of 11-deoxy-11α-nitromethyl-15-O-acetylprostaglandin $E_2$ methyl ester To a solution of 15.1 g. of the methyl ester of 15-O-acetylprostaglandin $A_2$ in 15 ml. of tetrahydrofuran is added a solution of 15 ml. nitromethane containing 1 ml. of a 35% solution of triton B (benzyl-trimethyl ammonium hydroxide) in methanol. The solution is stirred for one hour and is then poured into a mixture of 75 ml. of water and 70 ml. of ether. One ml. of 6 N aqueous hydrochloric acid is added and the aqueous layer is extracted with ether. The ether extracts are combined, washed with brine, dried (anhydrous magnesium sulfate) and evaporated in vacuo to afford 17.5 g. of an oil that can be purified by dry column chromatography; λmax 1740 cm$^{-1}$ (saturated carbonyls), 1555 cm$^{-1}$ ($NO_2$), 1375 cm$^{-1}$ ($NO_2$), 1225 cm$^{-1}$ (OAc), $[\alpha]_D^{25} = -45.5$, (C=0.530, chloroform).

EXAMPLES 40–45

Treatment of the indicated A-type prostaglandins with the designated nitroalkanes via the procedure of Example 39 is productive of the products of the following table.

| Example | Reagent Nitroalkane | Starting Prostaglandin A | Product - 11-deoxy-11α-(nitroalkyl)-prostaglandin E |
|---|---|---|---|
| 40 | nitroethane | 15-O-acetylprostaglandin $A_2$ methyl ester | 11-deoxy-11α-(α-nitroethyl)-15-O-acetylprostaglandin $E_2$ methyl ester |
| 41 | 2-nitropropane | 15-O-acetylprostaglandin $A_2$ methyl ester | 11-deoxy-11α-(α-nitro, α-methylethyl)-15-O-acetylprostaglandin $E_2$ methyl ester |
| 42 | 1-nitropropane | 15-O-acetylprostaglandin $A_2$ methyl ester | 11-deoxy-11α-(α-nitropropyl)-15-O-acetylprostaglandin $E_2$ methyl ester |
| 43 | nitromethane | prostaglandin $A_1$ methyl ester | 11-deoxy-11α-nitromethyl prostaglandin $E_1$ methyl ester |
| 44 | nitroethane | prostaglandin $A_1$ methyl ester | 11-deoxy-11α-(α-nitroethyl)prostaglandin $E_1$ methyl ester |
| 45 | nitromethane | 13,14-dihydroprostaglandin $A_1$ methyl ester | 11-deoxy-11α-nitromethyl-13,14-dihydroprostaglandin $E_1$ methyl ester |

EXAMPLE 46

Preparation of 11-deoxyprostaglandin $E_2$ methyl ester

To a suspension of 300 mg. potassium carbonate in 30 ml. of methanol is added 11-deoxy-15-O-acetyl-prostaglandin $E_2$ methyl ester (Example 96) in one ml. of methanol. The solution is stirred for 48 hours and is then acidified with 6 N aqueous hydrochloric acid. The solution is diluted with water and extracted with ether. The ether solution is washed with brine, dried with magnesium sulfate and evaporated in vacuo to yield 540 mg. of crude product. The product is purified by dry column chromatography using acid washed silica gel and eluting with 20% ethylacetate in benzene; λmax: 3400 cm$^{-1}$ (hydroxyl), 1735 cm$^{-1}$ (saturated ketone and ester).

EXAMPLE 47

Preparation of 11-deoxy-11α-nitromethyl prostaglandin $E_2$

To a solution of 11.54 g. of the methyl ester of 11-deoxy-11α-nitromethyl-15-O-acetyl-prostaglandin $E_2$ (Example 39) in 40 ml. of methanol is added 45 ml. of a 2.5 N sodium hydroxide solution and the resulting solution is stirred at room temperature for 2 hours. The solution is poured into 100 ml. of ether and 100 ml. of water. The aqueous layer is separated and extracted with ether. The aqueous layer is covered with ether and acidified with 23 ml. of 6 N aqueous hydrochloric acid. The acidic solution is saturated with sodium chloride and extracted with ether. The ether is dried with magnesium sulfate and evaporated in vacuo to give 10.3 g. of a viscous oil that is purified by dry column chromatography on acid washed silica gel; λmax 3600-3400 cm$^{-1}$ (hydroxyl and carboxyl), 1735 cm$^{-1}$ (saturated carbonyl), 1700 cm$^{-1}$ (carboxyl), 1550 cm$^{-1}$ (nitro); $[\alpha]_D^{25} = -41.5°$ (C=1.0, chloroform).

EXAMPLES 48–67

Saponification of the prostaglandin esters listed in the table by the indicated procedures yields the product prostaglandin acids of the following table.

| Example | Starting Prostaglandin Ester | Method of | Product Acid |
|---|---|---|---|
| 48 | Example 36 | Example 34 | 11-deoxy-11α-(α,α-dicarboethoxyethyl)prostaglandin $E_2$ |
| 49 | Example 37 | Example 34 | 11-deoxy-11α-(α,α-dicarboethoxypropyl)-prostaglandin $E_2$ |
| 50 | Example 38 | Example 34 | 11-deoxy-11α-(α,α-dicarboethoyxmethyl)-prostaglandin $E_1$ |
| 51 | Example 40 | Example 47 | 11-deoxy-11α-(α-nitroethyl)prostaglandin $E_2$ |
| 52 | Example 41 | Example 47 | 11-deoxy-11α-(α-nitro, α-methylethyl)prostaglandin $E_2$ |
| 53 | Example 42 | Example 47 | 11-deoxy-11α-(α-nitropropyl)prostaglandin $E_2$ |
| 54 | Example 43 | Example 47 | 11-deoxy-11α-nitromethyl prostaglandin $E_1$ |
| 55 | Example 44 | Example 47 | 11-deoxy-11α-(α-nitroethyl)prostaglandin $E_1$ |
| 56 | Example 45 | Example 47 | 11-deoxy-11α-nitromethyl-13,14-dihydroprostaglandin $E_1$ |
| 57 | Example 18 | Example 47 | 11-deoxy-11α-methyl-prostaglandin $E_2$ |
| 58 | Example 19 | Example 47 | 11-deoxy-11α-vinyl-prostaglandin $E_2$ |
| 59 | Example 20 | Example 47 | 11-deoxy-11α-ethyl-prostaglandin $E_2$ |
| 60 | Example 21 | Example 47 | 11-deoxy-11α-propyl-prostaglandin $E_2$ |
| 61 | Example 22 | Example 47 | 11-deoxy-11α-isopropyl-prostaglandin $E_2$ |
| 62 | Example 23 | Example 47 | 11-deoxy-11α-pentyl-prostaglandin $E_2$ |
| 63 | Example 24 | Example 47 | 11-deoxy-11α-methyl-prostaglandin $E_1$ |
| 64 | Example 25 | Example 47 | 11-deoxy-11α-ethylprostaglandin $E_1$ |
| 65 | Example 26 | Example 47 | 11-deoxy-11α-vinylprostaglandin $E_1$ |
| 66 | Example 27 | Example 47 | 11-deoxy-11α-propenyl-prostaglandin $E_1$ |
| 67 | Example 28 | Example 47 | 11-deoxy-11α-vinyl-13,14-dihydroprostaglandin $E_1$ |
| 67a | Example 173 | Example 47 | 11-deoxy-11α-(1-hydroxy-1-methylethyl)-prosta- |

-continued

| Example | Starting Prostaglandin Ester | Method of | Product Acid |
|---|---|---|---|
| | | | glandin $E_2$ |

EXAMPLE 68

Preparation of
11α/11β-cyano-11-deoxy-15-O-acetyl-prostaglandin $E_2$ methyl ester To a solution of 9.4 g. of the methyl ester of 15-O-acetyl-prostaglandin-$A_2$ in a mixtuure of 10 ml. acetonecyanohydrin and 10 ml. methanol is added 1 ml. of 5% aqueous sodium carbonate. The resulting solution is refluxed overnight and after cooling, poured into cold water and extracted with ether. The combined ether extracts are washed with brine and dried with anhydrous magnesium sulfate and evaporated in vacuo to give 12.3 g. of an oil.

The material is redissolved in benzene and washed with water to remove acetonecyanohydrin. The benzene solution is dried with magnesium sulfate and evaporated in vacuo. The material is purified by dry column chromatography to afford 8.5 g. of subject compound as an oil; λmax 2220 cm$^{-1}$ (nitrile), 1735 cm$^{-1}$ (saturated carbonyls); $[\alpha]_D^{25} = -56.23°$, (C=0.918, chloroform).

EXAMPLES 69–70

Treatment of the listed A-type prostaglandins by the procedure of Example 68 is productive of the 11α/β-cyano products of the following table.

| Example | Starting Prostaglandin-A | Product 11α/β-11-deoxy-prostaglandin-E |
|---|---|---|
| 69 | prostaglandin $A_1$ | 11α/β-cyano-11-deoxyprostaglandin $E_1$ |
| 70 | 13,14-dihydroprostaglandin $A_1$ | 11α/β-cyano-11-deoxy-13,14-dihydroprostaglandin $E_1$ |

EXAMPLE 71

Preparation of 11α/β-cyano-11-deoxy-prostaglandin $E_2$

To a solution of 3 g. of the methyl ester of 11α/β-cyano-11-deoxy-15-O-acetyl-prostaglandin $E_2$ (Example 68) in 36 ml. of methanol is added 12 ml. of an aqueous saturated solution of sodium cyanide. The solution is stirred for 96 hours and then poured into 100 ml. of ether. 20 ml. of water is added and the ether is extracted twice with 15 ml. 5% aqueous sodium bicarbonate. The combined aqueous extracts are acidified to pH 3 with 6 N aqueous hydrochloric acid, saturated with sodium chloride, and extracted with ether. The ether extracts are combined, dried with magnesium sulfate, and evaporated in vacuo to afford 1.64 g. of 11α/β-cyano-11-deoxyprostaglandin $E_2$ as an oil; λmax 3400 cm$^{-1}$ (carboxyl, hydroxyl), 2220 cm$^{-1}$ (nitrile), 1735 cm$^{-1}$ (saturated carbonyl), 1700 cm$^{-1}$ (carboxyl).

The first ether extract is dried with magnesium sulfate and evaporated in vacuo to afford 0.8 g. of 11α/β-cyano-11-deoxyprostaglandin $E_2$ methyl ester as an oil; λmax 3400 cm$^{-1}$ (hydroxyl), 2220 cm$^{-1}$ (nitrile), 1735 cm$^{-1}$ (saturated carbonyl, ester).

EXAMPLES 72–73

Ester hydrolysis of the following compounds by this procedure of Example 71 yields the products of the following table.

| Example | Starting Prostaglandin | Product 11α/β-cyano-11-deoxyprostaglandin E |
|---|---|---|
| 72 | Example 69 | 11α/β-cyano-11-deoxyprostaglandin $E_1$ |
| 73 | Example 70 | 11α/β-cyano-11-deoxy-13,14-dihydroprostaglandin $E_1$ |

EXAMPLE 74

Preparation of
11α/β-carboxamido-11-deoxy-15-O-acetyl prostaglandin $E_2$ methyl ester To a solution of 5.04 g. of the methyl ester of 11α/β-cyano-11-deoxy-15-O-acetylprostaglandin $E_2$ (Example 68) in 10 ml. of ethanol, 10 ml. tetrahydrofuran and 10 ml. cyclohexene is added a solution consisting of 1.5 ml. of 25% methanolic tetramethylammonium hydroxide in 7.0 ml. of 30% hydrogen peroxide. The resulting solution is heated to 60° C. for one hour and then stirred 48 hours at room temperature. One drop of methyltricaprylammonium chloride is added and the solution is heated for 2 hours at 55° C. The solution is cooled and poured into 100 ml. ether and 100 ml. water. The aqueous layer is extracted with ether. The ether extracts are combined, dried with anhydrous magnesium sulfate and evaporated in vacuo to give 4.96 g. of an oil. The oil is purified by dry column chromatography on a 20"×¼" column of silica gel and developed with 20% ethyl acetate in benzene to give 2.5 g. of the product carboxamide as an oil; λmax 3400–3600 cm$^{-1}$ (NH$_2$ of carboxamide), 1735 cm$^{-1}$ (saturated ketone and esters), 1675 cm$^{-1}$ (carboxamide carbonyl), 1620 cm$^{-1}$ (carboxamide), 1220 cm$^{-1}$ (acetate), 1180 cm$^{-1}$ (methyl ester); $[\alpha]_D^{25} = -114.7°$ (C=0.63, chloroform).

EXAMPLE 75

Preparation of
11α-carboxamido-11-deoxyprostaglandin $E_2$

To a solution of 1.41 g. of 11α/β-carboxamido-11-deoxy-15-O-acetylprostaglandin $E_2$ methyl ester (Example 74) in 5 ml. of methanol is added 2.8 ml. of a 2.5 N aqueous sodium hydroxide solution and 2.2 ml. of water. The solution is stirred overnight and poured into 50 ml. of ether and 50 ml. of water. The water is extracted with ether and the ether solutions are discarded. The aqueous solution is acidified to pH 2 with 6 N aqueous hydrochloric acid and saturated with sodium chloride. The aqueous solution is extracted with ether; the ethereal solution is dried with magnesium sulfate and the ether is evaporated in vacuo to yield 1.1 g. of the product as an oil; λmax: 3400 cm$^{-1}$ (carboxyl, hydroxyl, and amido hydrogens), 1740 cm$^{-1}$ (saturated ketone), 1710 cm$^{-1}$ (amide carbonyl); $[\alpha]_D^{25} = -25°$ (C=−76 chloroform, acetone).

EXAMPLE 76

Preparation of 11α-carboxy-11-deoxyprostaglandin $E_2$

To a solution of 737 mg. of 11α-carboxamido-11-deoxy-15-O-acetylprostaglandin $E_2$ methyl ester (Example 74) in 5 ml. of methanol is added dropwise 5 ml.

of a 2.5 N aqueous sodium hydroxide solution. The solution is heated at 80° C. for two hours and an additional 5 ml. of 2.5 N aqueous sodium hydroxide then is added and the solution is heated at 80° C. for 15 hours. The solution is cooled and extracted with ether. The aqueous solution is acidified with 6 N aqueous hydrochloric acid and extracted with ether. The ethereal solution is washed with brine, dried with magnesium sulfate and evaporated in vacuo to yield 520 mg. of the crude product; λmax: 3400-2700 cm$^{-1}$ (hydroxyl and carboxyl groups), 1740-1710 cm$^{-1}$ (saturated ketone and carboxyl groups).

EXAMPLES 77-79

Hydrogenation of the listed prostaglandin $E_2$ derivative by the procedure of Example 29 furnishes the product 13,14-dihydroprostaglandin $E_1$ of the following table.

| Example | Starting 11-substituted-prostaglandin $E_2$ | Product 11-substituted-13,14-dihydroprostaglandin $E_1$ |
|---|---|---|
| 77 | Example 74 | 11α-carboxamido-11-deoxy-13,14-dihydro-15-O-acetyl prostaglandin $E_1$ methyl ester |
| 78 | Example 75 | 11α-carboxamido-11-deoxy-13,14-dihydroprostaglandin $E_1$ |
| 79 | Example 76 | 11α-carboxy-11-deoxy-13,14-dihydroprostaglandin $E_1$ |

EXAMPLE 80

Preparation of 11-deoxy-11α-methyl-prostaglandin $F_{2\alpha}$

To a −78° C. solution of 877 mg. 11-deoxy-11α-methylprostaglandin $E_2$ (Example 57) in 8 ml. tetrahydrofuran is added 9.8 ml. of 0.66 M lithium perhydro-9-b-boraphenalyl hydride in tetrahydrofuran. The solution is stirred for 30 minutes and then 15 ml. of water is added and the dry-ice bath is removed. The solution is poured into 20 ml. of water and extracted with ether. The combined ether extracts are washed with 5% sodium bicarbonate. The combined aqueous solutions are acidified with 6 N hydrochloric acid, saturated with sodium chloride and extracted with ether. The ether is dried with anhydrous magnesium sulfate and evaporated in vacuo to an oil; λmax 3400 cm$^{-1}$ (OH), 1700 cm$^{-1}$ (COOH); 420 Hz (2H) 15-H and 9β-H; $[\alpha]_D^{25}=+15°$ (C=0.4, chloroform).

EXAMPLE 81

Preparation of 11α-carboxamido-11-deoxyprostaglandin $F_{2\alpha}$

To a −78° C. solution of 1.59 g. of the methyl ester of 11α-carboxamido-11-deoxy-15-O-acetyl-prostaglandin $E_2$ (Example 75) in 10 ml. tetrahydrofuran is added 7.35 ml. of 0.65 M lithium perhydro-9-b-boraphenalyl hydride in tetrahydrofuran. The solution is stirred for 60 minutes at −78°, then stirred at room temperature for 20 minutes. The tetrahydrofuran is evaporated in vacuo at 25° C. The residue is dissolved in 2 ml. methanol, 6 ml. water and 4 ml. of 2.5 N aqueous sodium hydroxide and stirred 3 hours at room temperature. The solution containing the 11-carboxamido-11-deoxy-15-O-acetyl-prostaglandin $E_2$ methyl ester is poured into 50 ml. of water and extracted with ether. The ether solution is washed with 5% aqueous sodium bicarbonate and combined with the aqueous solution. The combined aqueous solution is acidified with 6 N aqueous hydrochloric acid, saturated with sodium chloride, and extracted with ether. The ether is dried with magnesium sulfate and evaporated in vacuo to afford 1.48 g. of a viscous oil; λmax, 3400 cm$^{-1}$ (O$\underline{H}$, NH$_2$, COO$\underline{H}$), 1700 cm$^{-1}$ (COOH), 1660 cm$^{-1}$ (CONH$_2$); 405 Hz (15-$\underline{H}$, 9β-$\underline{H}$); $[\alpha]_D^{25}=+8.2°$ (C=0.65, chloroform).

EXAMPLES 82-89

Carbonyl reduction of the listed prostaglandin E derivatives by the procedure of the example designated furnishes the product prostaglandin $F_\alpha$, of the following table.

| Example | Starting 11-substituted prostaglandin E | Method | Product 11-substituted-prostaglandin F |
|---|---|---|---|
| 82 | Example 21 | 81 | 11α-propyl-11-deoxyprostaglandin $F_{2\alpha}$ |
| 83 | Example 22 | 81 | 11α-isopropyl-11-deoxyprostaglandin $F_{2\alpha}$ |
| 84 | Example 6 | 80 | 11α-methylthio-11-deoxyprostaglandin $F_{2\alpha}$ and 11α-methylthio-11-deoxyprostaglandin-$F_{2\beta}$ |
| 85 | Example 39 | 81 | 11α-nitromethyl-11-deoxyprostaglandin $F_{2\alpha}$ and 11α-nitromethyl-11-deoxyprostaglandin $F_{2\beta}$ |
| 86 | Example 35 | 80 | 11α-dicarboxymethyl-11-deoxyprostaglandin $F_{2\alpha}$ |
| 87 | Example 25 | 81 | 11α-ethyl-11-deoxyprostaglandin $F_{1\alpha}$ |
| 88 | Example 38 | 81 | 11α-(α,α-dicarboethoxy)-methyl-11-deoxyprostaglandin $F_{1\alpha}$ |
| 89 | Example 29 | 80 | 11α-methyl-11-deoxy-13,14-dihydroprostaglandin $F_{1\alpha}$ |

EXAMPLE 90

Conversion of 11α-methyl-11-deoxyprostaglandin $E_2$ to 11α-methyl-11-deoxyprostaglandin $F_{2\alpha}$ and 11α-methyl-11-deoxyprostaglandin $F_{2\beta}$ To a solution of 11α-methyl-11-deoxyprostaglandin $E_2$ in methanol at 0° C. is added 1 molar equivalent of sodium borohydride. After 60 minutes the solution is poured into water, acidified to pH=3 with 6 N hydrochloric acid, saturated with sodium chloride and extracted with ether. The ethereal solution is dried with magnesium sulfate and the ether is evaporated in vacuo to afford a mixture of 11α-methyl-11-deoxyprostaglandin $F_{2\alpha}$ and 11α-methyl-11-deoxyprostaglandin $F_{2\beta}$.

EXAMPLES 91-95

Carbonyl reduction of the listed 11-substituted prostaglandin (E type) by the method of Example 90 is productive of the 11-substituted prostaglandins (F type) of the table.

| Example | Starting 11-substituted prostaglandin | Product 11-substituted prostaglandin $F\alpha/\beta$ |
|---|---|---|
| 91 | Example 29 | 11α-methyl-11-deoxy-13,14-dihydroprostaglandin $F_{1\alpha}/F_{2\beta}$ |
| 92 | Example 51 | 11α-(α-nitroethyl)-11-deoxyprostaglandin $F_{2\alpha}/F_{2\beta}$ |
| 93 | Example 65 | 11α-vinyl-11-deoxyprostaglandin $F_{1\alpha}/F_{2\beta}$ |

| Example | Starting 11-substi-tuted prostaglandin | Product 11-substituted prostaglandin Fα/β |
|---------|----------------------------------------|-------------------------------------------|
| 94 | Example 75 | 11α-carboxamido-11-deoxyprostaglandin $F_{2\alpha}/F_{2\beta}$ |
| 95 | Example 66 | 11α-propenyl-11-deoxyprostaglandin $F_{1\alpha}/F_{1\beta}$ |

EXAMPLE 96

Preparation of 11-deoxyprostaglandin $E_2$ from 15-O-acetyl prostaglandin $A_2$ methyl ester To a solution of 1.04 g. of 15-O-acetylprostaglandin $A_2$ methyl ester in 5 ml. of methanol is added a solution of 209 mg. of sodium cyanoborohydride in 2 ml. of methanol. The solution is adjusted to pH 3 with 2 N methanolic hydrogen chloride and maintained at this pH by addition of methanolic hydrochloric acid as necessary. After 90 minutes the solution is evaporated in vacuo, 5 ml. of water is added. The solution is saturated with sodium chloride and extracted with ether. The ether extracts are dried with magnesium sulfate and evaporated in vacuo to yield 1.02 g. of an oil consisting mainly of 11-deoxy-15-O-acetyl-prostaglandin $F_{2\alpha}/F_{2\beta}$ methyl esters.

To a solution of 900 mg. of the above mixture of 11-deoxy-15-O-acetyl-prostaglandin $F_{2\alpha}/F_{2\beta}$ methyl esters in 30 ml. of acetone at 0° C. is added 0.8 ml. of a standard chromic acid solution. The solution is stirred 10 minutes and poured into 70 ml. of ice and water. The aqueous solution is extracted with ether. The ether solution is dried with magnesium sulfate and evaporated in vacuo to afford 830 mg. of 11-deoxy-15-O-acetyl-prostaglandin $E_2$ methyl ester as an oil.

To a solution of 11-deoxy-15-O-acetyl-prostaglandin $E_2$ methyl ester in methanol is added 4 equivalents of 2.5 N aqueous sodium hydroxide. The solution is stirred for 3 hours, poured into water, saturated with sodium chloride and acidified with 6 N aqueous hydrochloric acid to pH 3.

The acidic solution is extracted with ether. The ethereal extracts are dried with magnesium sulfate and evaporated in vacuo to afford 11-deoxyprostaglandin $E_2$; λmax: 3400-2700 cm$^{-1}$ (carboxyl and hydroxyl), 1745-1710 cm$^{-1}$ (saturated ketone and carboxyl groups).

EXAMPLE 97

Epimerization of 11-deoxyprostaglandin $E_2$ methyl ester

To a solution of 24 mg. of 11-deoxyprostaglandin $E_2$ methyl ester (Example 46) in 0.5 ml. of methylenechloride at $-5°$ C. is added 15 μl of triethylamine followed by 28 mg. of methanesulfonic acid anhydride in 0.5 cc methylenechloride. The solution is stirred at $-5°$ C. for 30 minutes and then all solvents are removed in vacuo.

The residue is dissolved in 5 ml. of ether and the ether solution is added to a flask containing 245 mg. of tetraethylammonium formate. The ether is evaporated in vacuo at $-5°$ C. and replaced by 2 cc of dry acetone. The solution is maintained at 10° C. for 18 hours. The acetone is removed in vacuo and the residue is dissolved in 10 cc ether. The ether solution is washed with 5 ml. of 5% aqueous sodium bicarbonate solution and 5 ml. of brine. The ether solution is dried with magnesium sulfate and the ether evaporated in vacuo to yield 26.7 mg. of 11-deoxy-15R-O-formylprostaglandin $E_2$ methyl ester as an oil.

Treatment of a solution of the 11-deoxy-15R-O-formylprostaglandin $E_2$ methyl ester in 0.5 ml. of methanol with a crystal of p-toluenesulfonic acid overnight yields 15R-11-deoxyprostaglandin $E_2$ methyl ester as as oil that chromatographs slightly ahead of the starting 15S-11-deoxyprostaglandin $E_2$ methyl ester on silica gel. The residue also contains some of the starting 15S material.

EXAMPLE 98

Racemization of 15S-11-deoxyprostaglandin $E_2$ methyl ester

To 13 mg. of 15S-11-deoxyprostaglandin $E_2$ methyl ester (Example 46) is added a solution of 5 mg. potassium carbonate in 0.5 ml. of 97% formic acid. The solution is stirred under nitrogen for 60 minutes. Benzene is added and the solution is evaporated in vacuo.

The residue is placed on a 2 mm silica gel plate and developed with 20% ethylacetate in benzene. The area corresponding to rf=0.45-0.65 is removed and the compound is eluted off of the silica-gel with 20% methanol in chloroform. The silica-gel is filtered and the organic solvents are evaporated in vacuo to yield 9 mg. of a mixture of 11-deoxy-15-O-formylprostaglandin $E_2$ methyl ester and the corresponding 15R epimer.

The mixture of 15-O-formyl compounds is dissolved in 1 ml. of methanol and one small crystal of p-toluenesulfonic acid is added. The solution is stirred overnight to afford approximately a 1:1 mixture of 15S-11-deoxyprostaglandin $E_2$ methyl ester and 15R-11-deoxyprostaglandin $E_2$ methyl ester.

Thin layer chromatography on silica-gel indicates the newly formed epimer (15R) is slightly less polar than the starting (15S) epimer.

EXAMPLE 99

Conversion of 11-deoxy-11α-nitromethylprostaglandin $E_2$ to 11-deoxy-11-formylprostaglandin $E_2$ A solution of 208 mg. 11-deoxy-11α-nitromethylprostaglandin $E_2$ (Example 47) in 5.5 ml. of 0.21 N aqueous sodium hydroxide is added dropwise to a very rapidly stirred solution of 0.5 ml. 6 N hydrochloric acid in 5 ml. methanol. The solution is poured into 30 ml. of ether and 25 ml. of brine is added. The ether extracts are washed with brine, dried with magnesium sulfate and evaporated in vacuo to afford 167 mg. of a viscous oil. Purification by dry column chromatography using ethyl acetate/benzene/acetic acid for development followed by elution from the silica-gel with 20% methanol/chloroform affords the product as a mixture of 11-formyl-11-deoxyprostaglandin $E_2$ and the corresponding acetyl, 11-dimethoxymethyl-11-deoxyprostaglandin $E_2$.

EXAMPLE 100

Conversion of 11-deoxy-11α-(α,α-dicarboxy)methylprostaglandin $E_2$ to 11-deoxy-11α-carboxymethylprostaglandin $E_2$ A solution of 11-deoxy-11α-(α,α-dicarboxy)methylprostaglandin $E_2$ (Example 35) is dissolved in xylene and heated until carbon dioxide evolution begins. The solution is maintained at that temperature until the starting material has been consumed (thin layer chromatography evidence). The xylene solution is evaporated in vacuo to afford the product.

EXAMPLE 101

Preparation of 11α-(β-dimethylaminoethylthio)-11-deoxy-15-O-acetyl-prostaglandin $A_2$ methyl ester A solution of 164 mg. of 2-diethylaminoethanethiol hydrochloride in 1 ml. of methanol containing 6 drops of a 5% aqueous sodium bicarbonate solution (pH ~ 8) is added to a solution of 104 mg. 15-O-acetylprostaglandin $A_2$ methyl ester in 1 ml. of methanol. The solution is stirred twenty minutes and then evaporated in vacuo to a paste. The paste was dissolved in 20 ml. of ether and 20 ml. of water. A small amount of sodium chloride is added to break up the emulsion formed. The aqueous layer is extracted with ether. The ether extracts are dried with magnesium sulfate and the ether is evaporated in vacuo to afford the product as an oil; λmax: 1745 cm$^{-1}$ (saturated ketone and esters), 1240 cm$^{-1}$ (acetate).

EXAMPLE 102

Preparation of 11-mercapto-15-O-acetylprostaglandin $F_{2\alpha}$ methyl ester

To a solution of 1.0 g. of 11-acetylthio-11-deoxy-15-O-acetyl prostaglandin $A_2$ methyl ester in 4 ml. of tetrahydrofuran maintained at −78° C. is added a solution of 0.65 M lithium perhydro-9-b-boraphenalyl hydride in tetrahydrofuran. The solution is stirred at −78° C. for 1 hour. The solution is then poured into 50 ml. of ether and 50 ml. of water and the aqueous layer is saturated with sodium chloride.

The aqueous layer is extracted with ether and the combined ether extracts are dried with magnesium sulfate and the ether is evaporated in vacuo to afford 1.7 g. of residue. Trituration of the residue with benzene/hexane followed by filtration and evaporation of the organic solvents affords 1.1 g. of crude product. The material is purified by partition chromatography to afford 150 mg. of 11-mercapto-11-deoxy-15-O-acetyl prostaglandin $F_{2\alpha}$ methyl ester.

EXAMPLE 103

Preparation of 1 20-ethyl prostaglandin $A_2$

A solution of 1 20-ethyl-9-oxo-11,15(S)-bis-(tetrahydropyran-2-yloxy)-5-cis-13-trans-prostadienoic acid [Patent No. 2,150,361 (West Germany, 1972)] in tetrahydrofuran containing 1.5 N hydrochloric acid is kept at ambient temperature for 70 hours. The solution is flooded with saturated sodium chloride and extracted several times with ether. The combined extracts are washed with water, dried with anhydrous magnesium sulfate and taken to dryness to afford the subject compound.

EXAMPLES 104–114

The prostaglandins E of the table below when treated in the manner of Example 103 furnish the corresponding prostaglandins A.

| Example | Starting Prostaglandins E | Product Prostaglandins A |
|---|---|---|
| 104 | 1-17,20-tetranor-16-m-chlorophenoxy-prostaglandin-$E_2$[a] | 1-17,20-tetranor-16-m-chlorophenoxy-prostaglandin-$A_2$ |
| 105 | 1-17,20-tetranor-16-phenoxyprosta-glandin-$E_2$[a] | 1-17,20-tetranor-16-phenoxyprosta-glandin-$A_2$ |
| 106 | 1-17,20-tetranor-16-p-fluorophenoxy-prostaglandin-$E_2$[a] | 1-17,20-tetranor-16-p-fluorophenoxy-prostaglandin-$A_2$ |
| 107 | 1-17,20-tetranor-16-m-trifluoro-methylphenoxyprostaglandin-$E_2$[a] | 1-17,20-tetranor-16-m-trifluoro-methylphenoxyprostaglandin-$A_2$ |
| 108 | 1-20-methylprostaglandin-$E_2$[b] | 1-20-methylprostaglandin-$A_2$ |
| 109 | 1-prostaglandin-$E_3$ - E. J. Corey, et al. Journ. Amer. Chem. Soc., 93, 1490 (1971) | 1-prostaglandin-$A_3$ |
| 110 | dl-prostaglandin-$E_2$ E. J. Corey, et al., Journ. Amer. Chem. Soc., 91, 5675 (1969) | dl-prostaglandin-$A_2$ |
| 111 | dl-17,20-tetranor-16-m-chlorophenoxy-prostaglandin-$E_2$[c] | dl-17,20-tetranor-16-m-chlorophenoxy-prostaglandin-$A_2$ |
| 112 | dl-17,20-tetranor-16-phenxoyprosta-glandin-$E_2$[c] | dl-17,20-tetranor-16-phenoxyprosta-glandin-$A_2$ |
| 113 | dl-17,20-tetranor-16-p-fluoro-phenoxyprostaglandin-$E_2$[c] | dl-17,20-tetranor-16-p-fluorophenoxy-prostaglandin-$A_2$ |
| 114 | dl-17,20-tetranor-16-m-trifluoromethyl-prostaglandin-$E_2$[c] | dl-17,20-tetranor-16-m-trifluoromethyl-phenoxyprostaglandin-$A_2$ |

References:
[a] D. Binder et al., Prostaglandins, Vol. 6, No. 1, 87 (1974).
[b] D. van Dorp, Annal of the New York Academy of Sciences, Volume 180, 181 (1971).
[c] Netherlands Patent No. 7,206,361, May 11, 1971.

EXAMPLES 115–129

Treatment of the A type prostaglandins, listed in the table below, with the listed alkyl mercaptans in the manner of Example 2 (method A) or Example 3 (method B) is productive of the 11α-alkylthioprostaglandins of the table.

| Example | Starting Prostaglandin A | Alkyl Reagent Mercaptan | Method | Product 11α-alkylthio-11-deoxyprostaglandin E |
|---|---|---|---|---|
| 115 | 1-prosataglandin-$A_3$ (Example 109) | Ethanethiol | B | 1-11-deoxy-11α-ethylthioprostaglandin-$E_3$ |
| 116 | 1-15-epiprosta-glandin-$A_2$ | Methanethiol | B | 1-11-deoxy-11α-methylthio-15-epi-prosta-glandin-$E_2$ |
| 117 | 1-15-epi-O-acetyl- | 1-propanethiol | A | 1-11-deoxy-11α-(1-propylthio)-15- |

-continued

| Example | Starting Prostaglandin A | Alkyl Reagent Mercaptan | Method | Product 11α-alkylthio-11-deoxyprostaglandin E |
|---|---|---|---|---|
| | prostaglandin-$A_2$ methyl ester | | | epi-O-acetylprostaglandin-$E_2$ methyl ester |
| 118 | dl-prostaglandin-$A_1$ | 1-butanethiol | B | dl-11-deoxy-11α-butylthioprostaglandin $E_1$ |
| 119 | l-15-methylprostaglandin-$A_1$ methyl ester | methanethiol | B | l-11-deoxy-11α-methylthiolprostaglandin-$E_1$ methyl ester |
| 120 | l-15-methylprostaglandin-$A_2$ methyl ester | ethanethiol | B | l-11-deoxy-11α-ethylthio-15-methylprostaglandin-$E_2$ methyl ester |
| 121 | l-16,16-dimethylprostaglandin-$A_2$ | 1-propanethiol | B | l-11-deoxy-11α-propylthiol-16,16-dimethylprostaglandin-$E_2$ |
| 122 | l-16(S)-methylprostaglandin-$A_2$ | ethanethiol | B | l-11-deoxy-11α-ethylthio-16(S)-methylprostaglandin-$E_2$ |
| 123 | l-16,16-difluoroprostaglandin-$A_2$ | Methanethiol | B | l-11-deoxy-11α-methylthio-16,16-difluoroprostaglandin-$E_2$ |
| 124 | l-16-fluoroprostaglandin-$A_2$ | Methanethiol | B | l-11-deoxy-11α-methylthio-16-fluoroprostaglandin-$E_2$ |
| 125 | l-20-ethylprostaglandin-$A_2$ (EX. 103) | Methanethiol | B | l-11-deoxy-11α-methylthiol-20-ethylprostaglandin-$E_2$ |
| 126 | dl-17,20-tetranor-16-p-fluorophenoxyprostaglandin-$A_2$ (EX. 113) | Ethanethiol | B | dl-11-deoxy-11α-ethylthio-17,20-tetranor-16-p-fluorophenoxyprostaglandin-$E_2$ |
| 127 | dl-17,20-tetranor-16-m-trifluoromethylphenoxyprostaglandin-$A_2$ (EX. 114) | Methanethiol | B | dl-11-deoxy-11α-methylthio-17,20-tetranor-16-m-trifluoromethylphenoxyprostaglandin-$E_2$ |
| 128 | l-17,20-tetranor-16-m-trifluoromethylphenoxyprostaglandin-$A_2$ (EX. 107) | Butanethiol | B | l-11-deoxy-11α-butylthio-17,20-tetranor-16-m-trifluoromethylphenoxyprostaglandin-$E_2$ |
| 129 | l-17,20-tetranor-16-m-chlorophenoxyprostaglandin-$A_2$ (EX. 104) | Methanethiol | B | l-11-deoxy-11α-methylthio-17,20-tetranor-16-m-chlorophenoxyprostaglandin-$E_2$ |

EXAMPLES 130–140

Treatment of the following prostaglandins $A_1$, listed in the table below, with the following indicated oganic lithium cuprate reagents in the manner of Examples 18 or 19 as indicated is productive of the 11-alkyl, or 11-alkenyl prostaglandin E type.

| Example | Starting Prostaglandin A | Cuprate Reagent | Method | Product 11-Substituted-11-deoxyprostaglandin E |
|---|---|---|---|---|
| 130 | l-prostaglandin-$A_3$ (Example 109) | dimethyl copper lithium | 18 | l-11-deoxy-11α-methylprostaglandin-$E_3$ |
| 131 | l-prostaglandin-$A_2$ methyl ester | dimethyl copper lithium | 18 | l-11-deoxy-11α-methylprostaglandin-$E_2$ methyl ester |
| 132 | l-15-epiprostaglandin-$A_2$ | diethyl copper lithium | 18 | l-11-deoxy-11α-ethyl-15-epi-prostaglandin-$E_2$ |
| 133 | l-prostaglandin-$A_2$ methyl ester | diphenylcopper lithium | 19 | dl-11-deoxy-11α-phenylprostaglandin $E_2$ and dl-11-deoxy-11β-phenylprostaglandin-$E_2$ methyl ester |
| 134 | l-15-methylprostaglandin-$A_2$ methyl ester | dimethyl copper lithium | 19 | l-deoxy-11α-methyl-15-methylprostaglandin-$E_2$ methyl ester |
| 135 | l-16,16-dimethylprostaglandin-$A_1$ methyl ester | dimethyl copper lithium | 18 | l-11-deoxy-11α-methyl-16,16-dimethylprostaglandin-$E_1$ methyl ester |
| 136 | l-16(S)-methylprostaglandin-$A_2$ | divinylcopper lithium | 19 | l-11-deoxy-11α-vinyl-16(S)-methylprostaglandin-$E_2$ |
| 137 | l-16-fluoroprostaglandin-$A_1$ | di(1-butenyl)-copper lithium | 19 | l-11-deoxy-11α-(1-butentyl)-16-fluoroprostaglandin-$E_2$ |

| Example | Starting Prostaglandin | Cuprate Reagent | Method of Example | Product 11-Substituted-11-deoxyprostaglandin-E |
|---|---|---|---|---|
| 138 | l-20-ethylprostaglandin-$A_2$ (Ex. 103) | dipropentyl-copper lithium | 19 | l-11-deoxy-11α-propenyl-20-ethylprostaglandin-$E_2$ |
| 139 | l-17,20-tetranor-16-m-trifluorophenoxyprostaglandin-$A_2$ (Ex. 114) | dimethyl-copper lithium | 18 | l-11-deoxy-11α-methyl-17,20-tetranor-m-trifluoromethylphenylprostaglandin-$E_2$ |
| 140 | l-17,20-tetranor-16-m-chlorophen- | dimethyl-copper lithium | 18 | l-11-deoxy-11α-methyl-17,20-tetranor-16-m-chlorophenoxyprostaglandin-$E_2$ |

| | | -continued | | |
|---|---|---|---|---|
| | oxyprostaglandin-$A_2$ (Ex. 104) | | | |
| 140A | 1-17,20-tetranor-16-m-trifluoro-methylphenoxyprosta-glandin-$A_2$ (Ex. 114) | divinyl-copper lithium | 19 | 1-11-deoxy-11α-vinyl-17,20-tetranor-16-m-trifluoromethylphenoxyprostaglandin-$E_2$ |
| 140B | 1-17,20-tetranor-16-m-chlorophenoxy-prostaglandin-$A_2$ (Ex. 104) | divinyl-copper lithium | 19 | 1-11-deoxy-11α-vinyl-17,20-tetranor-16-m-chlorophenoxyprostaglandin-$E_2$ |
| 140C | 1-17,20-tetranor-16-p-fluorophenoxy-prostaglandin-$A_2$ (Ex. 106) | divinyl-copper lithium | 19 | 1-11-deoxy-11α-vinyl-17,20-tetranor-16-p-fluorophenoxyprostaglandin-$E_2$ |
| 140D | 1-16,16-dimethyl-prostaglandin-$A_2$ | divinyl-copper lithium | 19 | 1-11-deoxy-11α-vinyl-16,16-dimethyl-prostaglandin-$E_2$ |

EXAMPLES 141–145

Reduction of the 11-deoxy-11-alkylprostaglandins E listed in the table below by the procedure of Example 29 yields the 11-alkyl-11-deoxy-13,14-dihydroprosta-glandins-$E_1$ of the table.

| Example | Starting 11α-alkyl prostaglandin E | Product 13,14-dihydroprostaglandin $E_1$ |
|---|---|---|
| 141 | 1-11-deoxy-11α-methyl-15-methyl-prostaglandin-$E_2$ methyl ester (EX. 134) | 1-11-deoxy-11α-methyl-13,14-dihydro-15-methyl-prostaglandin-$E_1$ methyl ester |
| 142 | 1-11-deoxy-11α-ethyl-15-epi-prostaglandin-$E_2$ (EX. 132) | 1-11-deoxy-11α-ethyl-15-epi-13,14-dihydro-prostaglandin-$E_1$ |
| 143 | 1-11-deoxy-11α-methyl-16,16-dimethylprostaglandin-$E_1$ methyl ester (EX. 135) | 1-11-deoxy-11αmethyl-13,14-dihydro-16,16-dimethylprostaglandin-$E_1$ methyl ester |
| 144 | 1-11-deoxy-11α-phenylprostaglandin-$E_2$ methyl ester (EX. 133) | 1-11-deoxy-11α-phenyl-13,14-dihydroprostaglandin-$E_1$ methyl ester |
| 145 | 1-11-deoxy-11α-methyl-17,20-tetra-nor-16-m-trifluoromethylphenoxy-prostaglandin-$E_2$ (EX. 139) | 1-11-deoxy-11α-methyl-13,14-dihydro-17,20-tetra-nor-16-m-trifluoromethylphenoxyprostaglandin-$E_1$ |

EXAMPLES 146–157

Treatment of the 11-deoxy-11α/β-acetylmercapto-prostaglandin E of the following table by the method of Example 236 is productive of the 11-deoxy-11α-mercaptoprostaglandin F of the table.

| Example | Starting 11-deoxy-11α/β-acetylmercaptoprostaglandin E | Product 11-deoxy-11α-mercaptoprostaglandin Fα |
|---|---|---|
| 146 | 223 | 1-11-deoxy-13,14-dihydro-11α-mercaptoprostaglandin-$F_{1α}$ |
| 147 | 224 | 1-11-deoxy-11α-mercaptoprostaglandin-$F_{3α}$ |
| 148 | 226 | 1-11-deoxy-15-epi-11α-mercaptoprostaglandin-$F_{2α}$ |
| 149 | 227 | dl-11-deoxy-11α-mercaptoprostaglandin-$F_{1α}$ |
| 150 | 228 | 1-11-deoxy-16,16-dimethyl-11α-mercaptoprostaglandin-$F_{1α}$ |
| 151 | 229 | 1-11-deoxy-16,16-dimethyl-11α-mercaptoprostaglandin-$F_{2α}$ |
| 152 | 230 | 1-11-deoxy-16(S)-methyl-11α-mercaptoprostaglandin-$F_{2α}$ |
| 153 | 231 | 1-11-deoxy-16-fluoro-11α-mercaptoprostaglandin-$F_{2α}$ |
| 154 | 232 | 1-11-deoxy-20-methyl-11α-mercaptoprostaglandin-$F_{2α}$ |
| 155 | 233 | dl-11-deoxy-17,20-tetranor-11α-mercapto-16-m-tri-fluoromethylphenoxyprostaglandin-$F_{2α}$ |
| 156 | 234 | 1-11-deoxy-16-p-fluorophenoxy-17,20-tetranor-11α-mercaptoprostaglandin-$F_{2α}$ |
| 157 | 235 | 1-16-m-chlorophenoxy-11-deoxy-17,20-tetranor-11α-mercaptoprostaglandin-$F_{2α}$ |

EXAMPLES 158–167

Treatment of the following A type prostaglandins by the procedure of Example 68 is productive of the 11α and 11β-cyano prostaglandins of the table. The 11α and 11β-epimers are separable from each other by chromatographic procedures (see Example 212).

| Example | Starting Prostaglandin A | Product 11α/β-cyano-11-deoxyprostaglandin E |
|---|---|---|
| 158 | 1-prostaglandin-$A_3$ (EX. 109) | 1-11-deoxy-11α-cyanoprostaglandin-$E_3$ and 1-11-deoxy-11β-cyanoprostaglandin-$E_3$ |
| 159 | dl-prostaglandin-$A_2$ | dl-11-deoxy-11α-cyanoprostaglandin-$E_2$ and dl-11-deoxy-11β-cyanoprostaglandin-$E_2$ |
| 160 | 1-15-methylprostaglandin-$A_2$ methyl ester | 1-11-deoxy-11α-cyano-15-methylprostaglandin-$E_2$ and 1-11-deoxy-11β-cyano-15-methylprosta- |

-continued

| Example | Starting Prostaglandin A | Product 11α/β-cyano-11-deoxyprostaglandin E |
|---|---|---|
| | | glandin-E₂ methyl esters |
| 161 | l-16,16-dimethylprostaglandin-A₂ | l-11-deoxy-11α-cyano-16,16-dimethylprostaglandin-E₂ and l-11-deoxy-11β-cyano-16,16-dimethylprostaglandin-E₂ |
| 162 | l-16(S)-methylprostaglandin-A₂ | l-11-deoxy-11α-cyano-16(S)-methylprostaglandin-E₂ and l-11-deoxy-11β-cyano-16(S)-methylprostaglandin-E₂ |
| 163 | l-16,16-difluoroprostaglandin-A₂ | l-11-deoxy-11α-cyano-16,16-difluoroprostaglandin-E₂ and l-11-deoxy-11β-cyano-16,16-difluoroprostaglandin-E₂ |
| 164 | l-16-fluoroprostaglandin-A₂ | l-11-deoxy-11α-cyano-16-fluoroprostaglandin-E₂ and d-11-deoxy-11β-cyano-16-fluoroprostaglandin-E₂ |
| 165 | dl-17,20-tetranor-16-p-fluorophenoxyprostaglandin-A₂ methyl ester (EX. 113) | dl-11-deoxy-11α-cyano-17,20-tetranor-16-p-fluorophenoxyprostaglandin-E₂ and dl-11-deoxy-11β-cyano-17,20-tetranor-16-p-fluorophenoxyprostaglandin-E₂ |
| 166 | l-17,20-tetranor-16-m-trifluoromethylphenoxyprostaglandin-A₂ (EX. 107) | l-11-deoxy-11α-cyano-17,20-tetranor-16-m-trifluoromethylphenoxyprostaglandin-E₂ and l-11-deoxy-11β-cyano-17,20-tetranor-16-m-trifluoromethylphenoxyprostaglandin-E₂ |
| 167 | l-17,20-tetranor-16-m-chlorophenoxyprostaglandin-A₂ (EX. 104) | l-11-deoxy-11α-cyano-17,20-tetrano-16-m-chlorophenoxyprostaglandin-E₂ and l-11-deoxy-11β-cyano-17,20-tetranor-16-m-chlorophenoxyprostaglandin-E₂ |

EXAMPLE 168

Preparation of
11-deoxy-11α-hydroxymethyl-15-O-acetyl prostaglandin-E₂ methyl ester,
11-deoxy-11β-hydroxymethyl-15-O-acetyl prostaglandin-E₂ methyl ester, and
8-iso-11-deoxy-11α-hydroxymethyl-15-O-acetyl prostaglandin-E₂ methyl ester A solution of 30 gm. (77 mmol) of 15-O-acetylprostaglandin-A₂ methyl ester benzophenone in 4 l. of methanol is irradiated with a Hanovia 450 medium pressure lamp thru a pyrex immersion well for 5 hours at ambient temperature. The solvent is removed in vacuo and the residue is triturated 10 times with 100 ml. of petroleum ether (30°–60° C.). The insoluble material (35 gm.) is chromatographed on a 4 foot ×6 inch (flat diaeter) nylon column of acid washed silica gel using ethyl acetate/benzene (1:3). The column is developed several times and fractions are collected.

From the chromatography is obtained 6 gm. of 11-deoxy-11β-hydroxymethyl-15-O-acetylprostaglandin-E₂ methyl ester: νmax 3400, 1735 cm$^{-1}$; $[\alpha]_D^{25}=-86°$. (c=0.2, MeOH); CDΔε=−3.2 at 293 nm. There is obtained both 8-iso and 8-normal-11-deoxy-11α-hydroxymethyl-15-O-acetylprostaglandin-E₂ methyl ester. These two products are further purified by dry column chromatography to give pure 11-deoxy-11α-hydroxymethyl-15-O-acetylprostaglandin-E₂ methyl ester: νmax−2.8 3400, 1735 cm$^{-1}$, $[\alpha]_D^{25}=-40°$. (c=0.2, MeOH), CD:Δε=−at 293 nm; and pure 8-iso-11-deoxy-15-O-acetylprostaglandin-E₂ methyl ester: νmax 3400, 1735 cm$^{-1}$; $[\alpha]_D^{25}=+25°$ (c=0.2, MeOH); CD:Δε=+2.04 at 293 nm.

EXAMPLES 169–182

Treatment of the following A type prostaglandins with the indicated alcohols in the manner of Example 168 gives the products of the table.

| Example | Starting Prostaglandin | Alcohol | Product |
|---|---|---|---|
| 169 | l-13-dihydroprostaglandin-A₁ | Ethanol | l-11-deoxy-11α-(1-hydroxyethyl)-13-dihydroprostaglandin-E₁ and 11-deoxy-11α-(1-hydroxyethyl)-13-dihydroprostaglandin-E₁ and 8-iso-11-deoxy-11α-(1-hydroxyethyl)-13-dihydroprostaglandin-E₁ |
| 170 | l-prostaglandin-A₁ | Isopropanol | l-11-deoxy-11α-(1-hydroxy-1-methylethyl)-prostaglandin-E₁ |
| 171 | l-prostaglandin-A₃ (EX. 109) | Methanol | l-11-deoxy-11α-hydroxymethyl-prostaglandin-E₃ and l-11-deoxy-11α-hydroxymethylprostaglandin-E₃ and 8-iso-11-deoxy-11α-hydroxymethylprostaglandin-E₃ |
| 172 | l-15-epiprostaglandin-A₂ | Methanol | l-11-deoxy-11α-hydroxymethyl-15-epiprostaglandin-E₂ and l-11-deoxy-11α-hydroxymethyl-15-epiprostaglandin E₂ and 8-iso-11-deoxy-11-hydroxymethyl-15-epiprostaglandin-E₂ |
| 173 | l-15-O-acetylprostaglandin-A₂ methyl ester | Isopropanol | l-11-deoxy-11α-(1-hydroxy-1-methylethyl)-15-O-acetylprostaglandin-E₂ methyl ester |
| 174 | dl-prostaglandin-A₂ | methanol | dl-11-deoxy-11α-hydroxymethylprostaglandin-E₂ dl-11-deoxy-11β-hydroxymethylprostaglandin-E₂ and dl-8-iso-11α-hydroxymethylprostaglandin-E₂ |
| 175 | l-15-methylprostaglandin-A₂ methyl ester | Methanol | l-11-deoxy-11α-hydroxymethyl-15-methylprostaglandin-E₂ methyl ester; l-11-deoxy-11β-hydroxymethyl-15-methylprostaglandin-E₂ and 8-iso-11-deoxy-11α-hydroxymethyl-15-methylprosta- |

-continued

| Example | Starting Prostaglandin | Alcohol | Product |
|---|---|---|---|
| | | | glandins-$E_2$ methyl ester |
| 176 | 1-16,16-dimethylprostaglandin-$A_1$ | Methanol | 1-11-deoxy-11α-(1-hydroxymethyl)-16,16-dimethylprostaglandin-$E_1$; 1-11-deoxy-11β-(1-hydroxymethyl)-16,16-dimethylprostaglandin-$E_1$ and 8-iso-11-deoxy-11α-(hydroxymethyl)-16,16-dimethylprostaglandin-$E_1$ |
| 177 | 1-16(R)-methylprostaglandin-$A_2$ | Methanol | 1-11-deoxy-11α-hydroxymethyl-16(R)-methylprostaglandin-$E_2$; 1-11-deoxy-11β-hydroxymethyl-16(R)-methylprostaglandin-$E_2$ and 8-iso-11-deoxy-11α-hydroxymethyl-16(R)-methylprostaglandin-$E_2$ |
| 178 | 1-16,16-difluoroprostaglandin-$A_2$ | Methanol | 1-11-deoxy-11α-hydroxymethyl-16,16-difluoroprostaglandin-$E_2$; 1-11-deoxy-11β-hydroxymethyl-16,16-difluoroprostaglandin-$E_2$ and 8-iso-11-deoxy-11α-hydroxymethyl-16,16-difluoroprostaglandin-$E_2$ |
| 179 | 1-20-ethylprostaglandin-$A_2$ | Methanol | 1-11-deoxy-11α-hydroxymethyl-20-ethylprostaglandin-$E_2$; 1-11-deoxy-11β-hydroxymethyl-20-ethylprostaglandin-$E_2$ and 8-iso-11-deoxy-11α-hydroxymethyl-20-ethylprostaglandin-$E_2$ |
| 180 | dl-17,20-tetranor-16-m-trifluoromethylphenoxyprostaglandin-$A_2$ (Example 114) | Methanol | dl-11-deoxy-11α-hydroxymethyl-17,20-tetranor-16-m-trifluoromethylphenoxyprostaglandin-$E_2$; dl-11-deoxy-11β-hydroxymethyl-17,20-tetranor-16-m-trifluoromethylphenoxyprostaglandin-$E_2$ and dl-8-iso-11-deoxy-11α-hydroxymethyl-17,20-tetranor-16-m-trifluoromethylprostaglandin-$E_2$ |
| 181 | 1-17,20-tetranor-16-p-fluorophenoxyprostaglandin-$A_2$ (Example 113) | Isopropanol | 1-11-deoxy-11α-(1-hydroxy-1-methylethyl)-17,20-tetranor-16-p-fluorophenoxyprostaglandin-$E_2$ |
| 182 | 1-17,20-tetranor-16-m-chlorophenoxyprostaglandin-$A_2$ (Example 111) | Methanol | 1-11-deoxy-11α-hydroxymethyl-17,20-tetranor-16-m-chlorophenoxyprostaglandin-$E_2$; 1-11-11β-hydroxymethyl-17,20-tetranor-16-m-chlorophenoxyprostaglandin-$E_2$ and 1-8-iso-11-deoxy-11α-hydroxymethyl-17,20-tetranor-16-m-chlorophenoxyprostaglandin-$E_2$ |

EXAMPLE 183

Preparation of
11-deoxy-11β-hydroxymethyl-prostaglandin $E_2$

To a solution of 395 mg. (0.94 mmol) of 11-deoxy-11β-hydroxymethyl-15-O-acetyl prostaglandin $E_2$ methyl ester (Example 168) in 2 ml. of methanol is added 1.6 ml. of a 2.5 N aqueous sodium hydroxide solution. The solution is stirred at ambient temperature for 1.5 hour and is then diluted with 20 ml. of water, saturated with sodium chloride, acidified with 6 N aqueous hydrochloricacid and extracted twice with 50 ml. of ether. The ether solutions are combined, dried with anhydrous magnesium sulfate and concentrated in vacuo to give 320 mg. of 11-deoxy-11β-hydroxymethyl-prostaglandin-$E_2$; $\nu$max 3400-2700 cm$^{-1}$, 1735 cm$^{-1}$; $[\alpha]_D^{25} = -59.3°$ (C=0.43 MeOH); CD: $\Delta E = -3.2$.

EXAMPLE 184

Preparation of
11-deoxy-11α-hydroxymethyl-prostaglandin-$E_2$ and 8-iso-11-deoxy-11α-hydroxymethyl-prostaglandin-$E_2$ To a solution of 810 mg. of 11-deoxy-11α-hydroxymethyl-15-O-acetyl prostaglandin methyl ester (Example 168) in 5 ml. of methanol is added 2.5 ml. of 2.5 N aqueous sodium hydroxide solution. The solution is stirred at room temperature for 2.5 hours and is then diluted with 25 ml. of water, saturated with sodium chloride, acidified with 1.1 ml. 6 N aqueous hydrochloric acid and extracted twice with 20 ml. of ether. The etheral solutions are combined, dried with anhydrous magnesium sulfate and concentrated in vacuo to give 680 mg. of a mixture of 8-normal and 8-iso-11α-hydroxymethyl-15-O-acetyl prostaglandin $E_2$. The mixture of 8-isomers is chromatographed on a 48″×1⅜″ flat diameter dry column of acid washed silica gel using ethyl acetate/benzene/acetic acid (3:2:2%). The column was developed 3 times and then cored at each 0.1 Rf unit to determine the position of each isomer. Rf fractions 0.1-0.25 and 0.35-0.7 were washed with ether to give 11-deoxy-11α-hydroxymethyl prostaglandin $E_2$: $\nu$max 3400, 1720-1690, 975 cm$^{-1}$; $[\alpha]_D^{25} = -6°$ (c=0.21, MeOH); CD:$\Delta\epsilon = -2.5$ at 293 nm and 8-iso-11-deoxy-11α-hydroxymethyl prostaglandin-$E_2$: $\nu$max 3400, 1720-1690, 975 cm$^{-1}$; $[\alpha]_D^{25} = +37°$ (c=0.23, MeOH); CD:$\Delta\epsilon = +2.04$ at 293 nm, respectively.

EXAMPLE 184A

Preparation of
11-deoxy-11α-(1-hydroxy-1-methylethyl)prostaglandin-$E_2$

The subject compound is prepared from the corresponding 15-O-acetyl methyl ester (Example 173) by saponification according to the method described in Example 183 above.

EXAMPLE 185

Preparation of
11-deoxy-11α-(1,3-dioxolan-2-yl)-15-O-acetylprostaglandin-$E_2$ methyl ester and
11-deoxy-11α-(1,3-dioxolan-2-yl)-15-O-acetylprostaglandin-$E_2$ methyl ester A solution of 5.0 gm. of 1-15-O-acetylprostaglandin-$A_2$ methyl ester and 1.2 gm. of benzophenone in 300 ml. of undistilled 1,3-dioxolan is irradiated with a medium pressure Hanovia U.V. Lamp through a Pyrex filter. After 20 minutes tlc indicates the reaction is complete.

The solvent is removed in vacuo to afford 8 gm. of an oil.

The material is purified by partition chromatography using heptane-acetonitrile to give: 4.4 gm of 1-11-deoxy-11α-(1,3-dioxolan-2-yl)-15-O-acetprostaglandin-$E_2$ methyl ester (low Rf material) and 1.72 gm of 1-11-deoxy-11α-(1,3-dioxolan-2-yl)-15-O-acetylprostaglandin-$E_2$ methyl ester (high Rf material) (tlc system 20% ethylacetate in benzene, silica gel, 2x).

The above products have nearly identical IR spectra 3400 cm$^{-1}$; 1740-1720 cm$^{-1}$, 975 cm$^{-1}$, $[\alpha]_D^{25}$ of high Rf material = $-19°$ (c=0.42 MeOH), $[\alpha]_D^{25}$ of low Rf material = $-81°$ (c=0.36 MeOH), CD of high Rf: 294 = $-3.30$ CD of low Rf: $-3.72$.

The configuration of the 1,3-dioxolano-2-yl function is assigned to each compound on the basis of the products derived from saponification of each diester. The high Rf material, upon saponification (see Example 184) gives two products which are assigned 1-11-deoxy-11α-(1,3-dioxolan-2-yl)-$PGE_2$ and 8-iso-11-deoxy-11α-(1,3-dioxolan-2-yl)-$PGE_2$. The low Rf diester upon identical saponfication conditions gave only a single isomer: 1-11-deoxy-11α-(1,3-dioxolan-2-yl)-$PGE_2$. Since it is very unlikely that a derivative with the 11α-configuration would give an 8-iso compound, the high Rf diester is assigned 11α.

EXAMPLES 186–198

Treatment of the following A type prostaglandins with the following in the manner of Example 185 is productive of the 11-(1,3-dioxolanyl-prostaglandins-E of the table.

| Example | Starting Prostaglandin | | Product |
|---|---|---|---|
| 186 | 1-13-dihydroprostaglandin-$A_1$ | 1,3-dioxolan | 1-11-deoxy-11β-(1,3-dioxolan-2-yl)-13-dihydroprostaglandin-$E_1$ and 11-deoxy-11α-(1,3-dioxolan-2-yl)-13-dihydroprostaglandin-$E_1$ |
| 187 | 1-prostaglandin-$A_1$ | 2-methyl-1,3-dioxolan | 1-11-deoxy-11α-(2-methyl-1,3-dioxolan-2-yl)-prostaglandin-$E_1$ and 1-11-deoxy-11β-(2-methyl-1,3-dioxolan-2-yl)-prostaglandin-$E_1$ |
| 188 | 1-prostaglandin-$A_3$ (EX. 109) | 1,3-dioxolan | 1-11-deoxy-11α-(1,3-dioxolan-2-yl)-prostaglandin-$E_3$ and 1-11-deoxy-11β-(1,3-dioxolan-2-yl)-prostaglandin-$E_3$ |
| 189 | 1-15-epiprostaglandin-$A_2$ | 1,3-dioxolan | 1-11-deoxy-11α-(1,3-dioxolan-2-yl)-15-epi-prostaglandin-$E_2$ and 1-11-deoxy-11β-(1,3-dioxolan-2-yl)-15-epi-prostaglandin-$E_2$ |
| 190 | dl-prostaglandin-$A_2$ | 1,3-dioxolan | dl-11-deoxy-11α-(1,3-dioxolan-2-yl)-prostaglandin-$E_2$ and dl-11-deoxy-11β-(1,3-dioxolan-2-yl)-prostaglandin-$E_2$ |
| 191 | 1-15-methylprostaglandin-$A_1$ methyl ester | 1,3-dioxolan | 1-11-deoxy-11α-(1,3-dioxolan-2-yl)-15-methylprostaglandin-$E_1$ methyl ester and 1-11-deoxy-11β-(1,3-dioxolan-2-yl)-15-methylprostaglandin-$E_1$ methyl ester |
| 192 | 1-16,16-dimethylprostaglandin-$A_2$ | 2-methyl-1,3-dioxolan | 1-11-deoxy-11α-(2-methyl-1,3-dioxolan-2-yl)-16,16-dimethylprostaglandin-$E_2$ and 1-11-deoxy-11β-(2-methyl-1,3-dioxolan-2-yl)-16,16-dimethylprostaglandin-$E_2$ |
| 193 | 1-16(R)-methylprostaglandin-$A_2$ | 1,3-dioxolan | 1-11-deoxy-11α-(1,3-dioxolan-2-yl)-16(R)-methylprostaglandin-$E_2$ and 1-11-deoxy-11β-(1,3-dioxolan-2-yl)-16(R)-methylprostaglandin-$E_2$ |
| 194 | 1-16,16-difluoroprostaglandin-$A_2$ | 1,3-dioxolan | 1-11-deoxy-11α-(1,3-dioxolan-2-yl)-16,16-difluoroprostaglandin-$E_2$ and 1-11-deoxy-11β-(1,3-dioxolan-2-yl)-16,16-difluoroprostaglandin-$E_2$ |
| 195 | 1-20-ethylprostaglandin-$A_2$ | 1,3-dioxolan | 1-11-deoxy-11α-(1,3-dioxolan-2-yl)-20-ethylprostaglandin-$E_2$ and 1-11-deoxy-11β-(1,3-dioxolan-2-yl)-20-ethyl-prostaglandin-$E_2$ |
| 196 | dl-17,20-tetranor-16-m-trifluorophenoxyprostaglandin-$A_2$ (Example 114) | 1,3-dioxolan | dl-11-deoxy-11α-(1,3-dioxolan-2-yl)-17,20-tetranor-16-m-trifluoromethylphenoxyprostaglandin-$E_2$ and dl-11-deoxy-(1,3-dioxolan-2-yl)-17,20-tetranor-16-m-trifluoromethylphenoxyprostaglandin-$E_2$ |
| 197 | 1-17,20-tetranor-16-p-fluorophenoxyprostaglandin-$A_2$ (Example 113) | 1,3-dioxolan | 1-11-deoxy-11α-(1,3-dioxolan-2-yl)-17,20-tetranor-16-p-fluorophenoxyprostaglandin-$E_2$ and 1-11-deoxy-11β-(1,3-dioxolan-2-yl)-17,20-tetranor-16-p-fluorophenoxyprostaglandin-$E_2$ |
| 198 | 1-17,20-tetranor-16-m-chlorophenoxyprostaglandin-$A_2$ (Example 111) | 1,3-dioxolan | 1-11-deoxy-11α-(1,3-dioxolan-2-yl)-17,20-tetranor-16-m-chlorophenoxyprostaglandin-$E_2$ and 1-11-deoxy-11β-(1,3-dioxolan-2-yl)-17,20-tetranor-16-m-chloroprostaglandin-$E_2$ |

EXAMPLE 199

Preparation of a mixture of the methyl esters of 11-deoxy-11α-(1-hydroxy-1-methylethyl-15-O-acetyl prostaglandin $F_2B$ and $F_2β$ and their separation To a cold solution of 816 mg. of 11-deoxy-11α-(1-hydroxy-1-methyl ethyl)-15-O-acetylprostaglandin methyl ester (Example 173) in 10 ml. of ethanol is added to a solution of 280 mg. of sodium borohydride in 15 ml. of methanol. After 10 minutes the solution is poured into 100 ml. of saturated ammonium chloride and extracted three times with 50 ml. of ether. The ether is combined, dried with magnesium sulfate, and concentrated in vacuo to give 990 mg. of a yellow oil. The mixture of the alcohols (900 mg.) is chromatographed on a 35"×1½ flat diameter dry column of acid washed silica using ethyl acetate/benzene (2:3). The column is cored at each 0.1 Rf unit. The following portions are removed: 0.75–1.0 and 0.2–0.5. Elution of the 0.75–1.0 portion with 20% methanol in chloroform gave 513 mg. of 11-deoxy-11α-(1-hydroxy-1-methylethyl)-15-O-acetyl prostaglandin F$_2$α methyl ester as an oil; νmax 3400, 1720 cm$^{-1}$; nmr (CDCl$_3$ δ:4.2 (m, 1H, H-9β); $[α]^{25}=-19°$; (c=0.21, MeOH). Similar elution of the 0.2–0.5 portion gave 270 mg. of 11-deoxy-11α-(1-hydroxy-1-methylethyl-15-O-acetyl prostaglandin F$_2$α/β methyl ester; νmax: 3400, 1720 cm$^{-1}$ pmr (CDCl3) δ:3.9 (m, 1H, H-9β) $[α]_D^{25}=-26°$ (0.22, MeOH).

EXAMPLES 200–211

Treatment of the following E type prostaglandins with sodium borohydride in ethanol by the procedure of Example 199 provides the mixture of 9-hydroxy prostanoic acids or esters of the following table. The F$_α$ and F$_β$ components are separable by chromatography.

EXAMPLE 212

Separation of 1-11-deoxy-11α-cyanoprostaglandin E$_2$ and 1-11-deoxy-11α-cyanoprostaglandin-E$_2$ by silica gel chromatography A solution of 2.6 gm. of a mixture of 1-11-deoxy-11α-cyanoprostaglandins-E$_2$ and 11-deoxy-11β-cyanoprostaglandin-E$_2$ (Example 71) in 5 ml. of methylene chloride was placed on top of a 40"×2" flat diameter nylon column placed with acid washed silica. The column was developed with 40% ethylacetate in benzene containing 2% acetic acid. A single development required 700 ml. A total of 1700 ml. was used with 100 ml. fractions being collected. Fraction 6 contained 540 mg. of pure 1-11-deoxy-11α-cyanoprostaglandin-E$_2$ $[α]_D^{25}=0°$ (C=0.65 MeOH) λmax. 3400, 1730–1690; 975 cm$^{-1}$; pmr CDCl$_3$ (δ): 3.2–3.5 (m, 1H, H-11), 4.2–4.3 (m, 1H, H$_{15}$), 5.2–5.5 (m, 2H, H5, H6), 5.7–5.85 (m, 2H, H13, H14), Δε296=−2.46. Fraction 4 consisted of primarily 1-11-deoxy-11β-cyanoprostaglandin-E$_2$ $[α]_D^{25}=35°$ (C=0.67 MeOH) λmax. 3400, 1730–1710, 975 cm$^{-1}$; pmr CDCl$_3$ (δ): 4.2 (m, 1H, H15), 5.3–5.6 (m, 2H, H5, H6), 5.6–6.0 (mM, 2H, H13, H14), Δε296=−0.26.

EXAMPLES 213–216

Treatment of the following E type prostanoic acids with lithium tri-sec-butyl borohydride in tetrahydrofuran by the method of Example 81 furnishes the 9-

| Example | Starting E Prostaglandin | Product F Prostaglandins |
|---|---|---|
| 200 | 1-11-deoxy-11α-ethylthioprostaglandin-E$_3$ (EX. 115) | 1-11-deoxy-11α-ethylthioprostaglandins-F$_3$α and F$_3$β |
| 201 | 1-11-deoxy-11α-ethylthio-16-p-fluorophenoxyprostaglandin-E$_2$ (EX. 126) | 1-11-deoxy-11α-ethylthio-16-p-fluorophenoxyprostaglandins-F$_2$α and F$_2$β |
| 202 | 1-11-deoxy-11α-vinyl-16(S)-methyl-prostaglandin-E$_2$ (EX. 136) | 1-11-deoxy-11α-vinyl-16(S)-methylprostaglandins-F$_2$α and F$_2$β |
| 203 | 1-11-deoxy-11α-methyl-13,14-dihydro-17,20-tetranor-16-m-trifluoromethylphenoxyprostaglandin-E$_1$ (EX. 145) | 1-11-deoxy-11α-methyl-13,14-dihydro-17,20-tetranor-16-m-trifluoromethylphenoxyprostaglandins-F$_1$α and F$_1$β |
| 204 | 1-11-deoxy-11α-methyl-16,16-dimethyl prostaglandin-E$_2$ (EX. 135) | 1-11-deoxy-11α-methyl-16,16-dimethylprostaglandins-F$_2$α and F$_2$β |
| 205 | 1-11-deoxy-11α-methyl-17,20-tetranor-16-m-chlorophenoxyprostaglandin-E$_2$ (EX. 140) | 1-11-deoxy-11α-methyl-17,20-tetranor-16-m-chlorophenoxyprostaglandins F$_2$α and F$_2$β |
| 206 | dl-11-deoxy-11α-cyano-17,20-tetranor-16-p-fluorophenoxyprostaglandin-E$_2$ (Ex. 165) | dl-11-deoxy-11α-cyano-17,20-tetranor-16-p-fluorophenoxyprostaglandins-F$_2$α and F$_2$β |
| 207 | 1-11-deoxy-11α-hydroxymethyl-prostaglandin-E$_2$ (EX. 184) | 1-11-deoxy-11α-hydroxymethylprostaglandin-F$_2$β |
| 208 | 1-11-deoxy-11β-hydroxymethyl-15-epiprostaglandin-E$_2$ (EX. 172) | 1-11-deoxy-11β-hydroxymethyl-15-epiprostaglandins-F$_2$α and F$_2$β |
| 209 | 8-iso-11-deoxy-11α-hydroxymethyl-16(R)-methylprostaglandin-E$_2$ (EX. 177) | 8-iso-11-deoxy-11α-hydroxymethyl-16(R)-methylprostaglandins-F$_2$α and F$_2$β |
| 210 | 1-11-deoxy-11β-(1,3-dioxolan-2-yl)-prostaglandin-E$_2$ (EX. 185) | 1-11-deoxy-11β-(1,3-dioxolan-2-yl)-prostaglandins-F$_2$α and F$_2$β |
| 211 | 1-11-deoxy-11α1,3-dioxolan-2-yl)-17,20-tetranor-16-p-fluorofluorophenoxyprostaglandin-E$_2$ (EX. 197) | 1-11-deoxy-11α-(1,3-dioxolano-2-yl)-17,20-tetranor-16-p-fluorophenoxyprostaglandins-F$_2$α and F$_2$β | hydroxy prostanoic acids of the following wherein the 9-hydroxy group is cis to the 11-substituent.

| Example | Starting 9-oxo prostaglandin | Product 9-hydroxy prostaglandin |
|---|---|---|
| 213 | 1-11-deoxy-11β-cyanoprostaglandin-E$_2$ (EX. 212) | 1-11-deoxy-11β-cyanoprostaglandin-F$_2$β |
| 214 | 1-11-deoxy-11α-phenylprostaglandin-E$_2$ (EX. 133) | 1-11-deoxy-11α-phenylprostaglandin-F$_2$α |

-continued

| Example | Starting 9-oxo prostaglandin | Product 9-hydroxy prostaglandin |
|---|---|---|
| 215 | l-11-deoxy-11α-(1,3-dioxolan-2-yl)-prostaglandin-$E_2$ (EX. 188) | l-11-deoxy-11α-(1,3-dioxolan-2-yl)-prostaglandin-$F_{2\alpha}$ |
| 216 | dl-11-deoxy-11α-(1,3-dioxolan-2-yl)-17,20-tetranor-16-p-fluoro-prostaglandin-$E_2$ (EX. 211) | dl-11-deoxy-11α-(1,3-dioxolan-2-yl)-17,20-tetranor-16-p-fluoroprostaglandin-$F_{2\alpha}$ |

EXAMPLE 217

Preparation of
1-11-deoxy-11α-formyl-15-O-acetylprostaglandin-$E_2$
methyl ester from
1-11-deoxy-11α-(1,3-dioxolan-2-yl)-15-O-acetylprostaglandin-$E_2$ methyl ester A solution of 1 gm. of 1-11-deoxy-11α-(1,3-dioxolan-2-yl)-15-O-acetylprostaglandin-$E_2$ methyl ester (Example 185) in 20 ml. of a solution consisting of acetic acid, tetrahydrofuran and water in a 2:1:1 ratio is heated to 45° C. for 16 hours. The cooled solution is concentrated in vacuo and the residue is diluted with 100 ml. of benzene and washed twice with 100 ml. of brine. The benzene layer is separated and after drying with magnesium sulfate is concentrated in vacuo to give the subject compound: λmax: 1740–1710 cm$^{-1}$, 975 cm$^{-1}$.

EXAMPLES 218–222

Subjection of the following 11-1,3-dioxolan-2-yl prostaglandins of the table to the reaction conditions of Example 217 is productive of the products listed in the table.

| Example | Starting Prostaglandin | Product Prostaglandin |
|---|---|---|
| 218 | l-11-deoxy-11β-(2-methyl-1,3-dioxolan-2-yl)prostaglandin-$E_1$ (EX. 187) | l-11-deoxy-11β-acetylprostaglandin-$E_1$ |
| 219 | l-11-deoxy-11α-(1,3-dioxolan-2-yl)-15-epi-prostaglandin-$E_2$ (Ex. 189) | l-11-deoxy-11α-formyl-15-epi-prostaglandin-$E_2$ |
| 220 | l-11-deoxy-11α-(1,3-dioxolan-2-yl)-16(R)-methylprostaglandin-$E_2$ (EX. 193) | l-11-deoxy-11α-formyl-16(R)-methylprostaglandin-$E_2$ |
| 221 | l-11-deoxy-11β-(1,3-dioxolan-2-yl)-16,16-difluoroprostaglandin-$E_2$ (EX. 194) | l-11-deoxy-11β-formyl-16,16-difluoroprostaglandin-$E_2$ |
| 221A | dl-11-deoxy-11α-(1,3-dioxolan-2-yl)-17,20-tetranor-16-m-trifluoromethylprostaglandin-$E_2$ (Ex. 196) | dl-11-deoxy-11α-formyl-17,20-tetranor-16-m-trifluoromethylprostaglandin-$E_2$ |
| 222 | l-11-deoxy-11α-(1,3-dioxolan-2-yl)-17,20-tetranor-16-m-chlorophenoxyprostaglandin-$E_2$ (EX. 198) | l-11-deoxy-11α-formyl-17,20-tetranor-16-m-chlorophenoxyprostaglandin-$E_2$ |
| 222A | l-11-deoxy-11β-(1,3-dioxolan-2-yl)prostaglandin $E_2$ (EX. 210) | l-11-deoxy-11β-formylprostaglandin $E_2$ |
| 222B | l-11-deoxy-11β-(1,3-dioxolo-2-yl)prostaglandin $F_2$ (EX. 210) | l-11-deoxy-11β-formylprostaglandin-$F_2$ |
| 222C | l-11-deoxy-11β-(1,3-dioxolan-2-yl)prostaglandin $E_2$ (EX. 185) | l-11-deoxy-11β-formylprostaglandin-$E_2$ |

EXAMPLES 223–235

Treatment of the following A type prostaglandins with the indicated lower alkanoylthiol carboxylic acid in the manner of Example 13 is productive of the 11-lower alkanoylthioprostaglandins of the table.

| Example | Starting Prostaglandin A | Reagent thiol alkanoic acid | Product 11α/β-11-deoxy-alkanylthio-prostaglandin E |
|---|---|---|---|
| 223 | l-13-dihydroprostaglandin-$A_1$ | thiolpropanoic acid | l-11-deoxy-11α-propanoylthio-13-dihydroprostaglandin-$E_1$ and 11-deoxy-11β-propanoylthiol-13-dihydro-prostaglandin-$E_1$ |
| 224 | l-prostaglandin-$A_3$ | thiolacetic acid | l-11-deoxy-11α-acetylthioprostaglandin-$E_3$ and l-11-deoxy-11β-acetyl-thioprostaglandin-$E_3$ |
| 225 | l-prostaglandin-$A_2$ methyl ester | thiolacetic acid | l-11-deoxy-11α-acetylthioprostaglandin-$E_2$ methyl ester and l-11-deoxy-11β-acetylthioprostaglandin-$E_2$ methyl ester |
| 226 | l-15-epiprostaglandin-$A_2$ | thiolacetic acid | l-11-deoxy-11α-acetylthio-15-epi-prostaglandin-$E_2$ and l-11-deoxy-11β-acetylthio-15-epiprostaglandin-$E_2$ |
| 227 | dl-prostaglandin-$A_1$ | thiolacetic acid | dl-11-deoxy-11α-acethylthioprostaglandin-$E_1$ and dl-11-deoxy-11β-acetyl-thiolprostaglandin-$E_1$ |
| 228 | l-16,16-dimethylprostaglandin-$A_1$ | thiolacetic acid | l-11-deoxy-11α-acetylthio-16,16-dimethylprostaglandin-$E_1$ and l-11-deoxy-11β-acetylthio-16,16-dimethylprosta- |

-continued

| Example | Starting Prostaglandin A | Reagent thiol alkanoic acid | Product 11α/β-11-deoxy-alkanylthio-prostaglandin E |
|---|---|---|---|
| | | | glandin-E$_1$ |
| 229 | l-16,16-dimethylprosta-glandin-A$_2$ | thiolacetic acid | l-11-deoxy-11-6O-acetylthiol-16,16-dimethylprostaglandin-E$_2$ and l-11-deoxy-11β-acetylthio-16,16-dimethylprostaglandin-E$_2$ |
| 230 | l-16(S)-methylprosta-glandin-A$_2$ | thiolacetic acid | l-11-deoxy-11α-acetylthiol-16(S)-methylprostaglandin-E$_2$ and l-11--deoxy-11β-acetylthio-16(S)-methyl-prostaglandin-E$_2$ |
| 231 | l-16-fluoroprostaglandin-A$_2$ | thiolacetic acid | l-11-deoxy-11α-acetylthio-16-fluoro-prostaglandin-E$_2$ and l-11-deoxy-11β-acetylthio-16-fluoroprostaglandin-E$_2$ |
| 232 | l-20-methylprostaglandin-A$_2$ | thiolacetic acid | l-11-deoxy-11α-acetylthio-20-methyl-prostaglandin-E$_2$ and l-11-deoxy-11β-acetylthiol-20-methylprostaglandin-E$_2$ |
| 233 | dl-17,20-tetranor-16-m-trifluoromethylphenoxy-prostaglandin-E$_2$ (EX. 114) | thiolacetic acid | dl-11-deoxy-11α-acetylthio-17,20-tetranor-16-m-trifluoromethylphenoxy-prostaglandin-E$_2$ and dl-11-deoxy-11β-acetylthiol-17,20-tetranor-16-m-trifluoromethylphenoxyprostaglandin-E$_2$ |
| 234 | l-17,20-tetranor-16-p-fluorophenoxyprosta-glandin-A$_2$ (EX. 113) | thiolacetic acid | l-11-deoxy-11α-acetylthio-17,20-tetranor-16-p-fluorophenoxyprosta-glandin-E$_2$ and l-11-deoxy-11β-acetyl-thiol-17,20-tetranor-16-p-fluoro-phenoxyprostaglandin-E$_2$ |
| 235 | l-17,20-tetranor-16-m-chlorophenoxyprosta-glandin-A$_2$ (EX. 111) | thiolacetic acid | l-11-deoxy-11α-acetylthio-17,20-tetranor-16-m-chlorophenoxyprosta-glandin-E$_2$ and l-11-deoxy-11β-acetyl-thiol-17,20-tetranor-16-m-chloro-phenoxyprostaglandin-E$_2$ |

EXAMPLE 236

Preparation of
1-11-deoxy-11α-mercaptoprostaglandin-F$_2$α

A solution of 2.25 gm. of the crude prostaglandin A$_2$ extract (60% real) from *plexaura homomalla* in 10 ml. of thiolacetic acid is heated at 60° C. for 3 hours. After cooling, the solution is diluted with 20 ml. of benzene and concentrated in vacuo to an oil. Benzene (40 ml.) is added and removed in vacuo to provide 2.6 gm. of an oil.

The crude oil is purified by partition chromatography using heptane methanol on celite to provide 1.4 gm. of l-11α/β-acetylthio-11-deoxyprostaglandin-E$_2$ as an oil; λmax: 1740, 1720, 975 cm$^{-1}$.

To a −78° C. solution of 15 ml. of 1.0 M lithium tri-sec-butylborohydride in tetrahydrofuran/pentane (1:1) is added 1.15 gm. (2.8 mmol) of l-11α/β-acet-ylthio-11-deoxyprostaglandin-E$_2$ in 5 ml. of tetrahydrofuran. After 30 minutes at −78° C., 10 ml. of water is added and the resulting mixture is stirred in a 30° C. both for 30 minutes. The solution is diluted with an additional 30 ml. of water and extracted four times with 50 ml. of ether.

The aqueous solution is acidified to pH 4 with 2.5 ml. of 6 N hydrochloric acid, saturated with sodium chloride and extracted twice with 50 ml. of ether and twice with 50 ml. of ethyl acetate. The combined organic extracts are dried with magnesium sulfate and concentration in vacuo to provide 900 mg. of an oil.

The crude oil is purified on Wolem acid-washed silica-gel using chloroform as solvent to provide 240 mg. of l-11-deoxy-11α-mercaptoprostaglandin-F$_2$α as a was: λmax: 3400, 1700, 975 cm$^{-1}$; pmr (CDCl$_3$): δ(4.1-4.4, m, 2-H, H9$_b$ and H$_{15}$), (5.05-5.25, M, 4H, exchangeable with CD$_3$OD), (5.25-5.7, M, 4H, H$_5$, H$_6$, H$_{13}$ and H$_{14}$); [α]$_D^{25}$ = +16° (C=0.35 MeOH).

EXAMPLE 237

Preparation of 11α-cyano-11-deoxyprostaglandin F$_2$α, 11β-cyano-11-deoxyprostaglandin F$_2$β and 11β-cyano-11-deoxyprostaglandin F$_2$α

To a solution of 2.84 g. of 40 in 15 ml. of tetrahydrofuran at −78° C. is added 14 ml. of a 0.65 M solution of LPBH. After 60 minutes at −78° C. tlc indicated some ketone remaining after warming to room temperature, the solvent is removed in vacuo and 10 ml. of methanol, 5 ml. of water and 5 ml. of 2.5 N sodium hydroxide are added. After 3 hours, 50 ml. of water is added and the solution is extracted with 3×50 ml. of ether. The aqueous phase is acidified with 6 N hydrochloric acid, saturated with sodium chloride and extracted with ether. The ether is washed with brine, dried and evaporated to yield 2.4 g. of an oil that consists of 4 spots of tlc (EtOAc-benzene-HOAc: 40:60:1.5, 2x, silica-gel).

The oil is chromatographed on a 30"×1½" flat diameter silica-gel) dry column using EtOAc-benzene-HOAc (60-40:3) as solvent. TLC of plugs indicates pooling the following Rf fractions: 0.45–0.65 (A), 0.65–0.73 (B) and 0.73–0.83 (C). The compound is eluted from the silica-gel with 20% MeOH/CHCl$_3$ to give: A: 912 mg., B: 650 mg., and C: 550 mg.

A and B are combined and rechromatographed on a 30"×1½" flat diameter dry silica-gel column using ETOAc-OH-HOAc (40-60:3). TLC indicates combining Fr: 0.2–0.41 (A), 0.41–0.48 (B) and 0.48–0.7 (C). Elution from the absorbant will give: A': 230 mg., B': 210 mg. and C': 650 mg. TLC indicates A' nearly pure. Recrystallization of A' from ETOAc-hexane gives 130 mg. of 11β-cyano-11-deoxyprostaglandin-F$_2$β: m.p. 76°–78° C.; λmax. 3400-2700, 2220, 1710 cm$^{-1}$; pmr (CDCl$_3$): $\delta$2.98 (q, 1H, W$_{\frac{1}{2}}$=20 Hz, H$_{11\alpha}$), 3.96 (q, 1H, W$_{\frac{1}{2}}$=20 Hz, H$_{11\alpha}$), 3.96 (q, 1H, W$_{\frac{1}{2}}$=20 Hz, H$_{9\alpha}$), 4.17 (q, 1H, W$_{\frac{1}{2}}$=18 Hz, H$_{15}$), 5.48 (m, 2H, H$_{5,6}$), 5.70 (m, 2H, H$_{13,14}$); [$\alpha$]$_D^{25}$=+68.8° (C+0.93 chloroform). N.O.E.[20] indicates that H-11 and the beta alkyl chain are trans.

A portion of the major component (C+C' combined, 790 mg.) is treated with a semicarbizide-acetic acid solution to form the semicarbizone of unreacted ketone that possesses nearly the same Rf as the products. The resulting oil is chromatographed on a 24"×1" flat diameter dry silica-gel column using EtOAc-benzene-HOAc (20:30:1). Elution of the material from Rf 0.35-0.55 with 20% methanol-chloroform give 375 mg. of 11$\alpha$-cyano-11-deoxyprostaglandin F$_{2\alpha}$ as an oil that solidifies upon storage at −10°; $\lambda$max 3400-2200, 2220, 1710 cm$^{-1}$; pmr (CDCl$_3$): $\delta$2.6 (m, ~2H, H$_{11,12}$), 4.17-4.3 (m, 2H, H$_{9\beta,15}$), 5.50 (m, 3H, H$_{5,6,13}$), 5.76 (d-d, 1H, J=15 Hz, Jobs 14,15=5 Hz, H$_{14}$); [$\alpha$]$_D^{25}$=+2.24°, (C=0.713, chloroform). N.O.E.[20] indicates that H-11 and the beta alkyl chain were cis.

B' is recrystallized to give a solid that is a mixture of 11$\beta$-cyano-11-deoxyprostaglandin F$_{2\beta}$ and the next less plar component. The pmr spectrum (CDCl$_3$) indicated this material consists of 11$\beta$-cyano-11-deoxyprostaglandin F$_{2\beta}$ and 11$\beta$-cyano-11-deoxyprostaglandin F$_{2\beta}$ and (1:1): $\delta$2.96 (two overlapping quartets, H$_{11\alpha}$), 3.97 (q, $\frac{1}{2}$H, W $\frac{1}{2}$−20 Hz, H$_{9\alpha}$), 4.18 (m, H$_{15}$ and H$_{9\beta}$, 1$\frac{1}{2}$H), 5.48 (m, H$_{5,6}$) and 5.65-5.9 (m, H$_{13,14}$). Compounds are assumed epimeric at C-9 since their H$_{11}$ resonances are nearly coincident.

EXAMPLES 238-326

Carbonyl reduction of the listed prostaglandin E derivatives by the procedure of the example designated will furnish the product prostaglandins F of the following table. In these instances where a prostaglandin F$\alpha$ and a prostaglandin F$\beta$ are formed, these components are separable by chromatographic procedures (see Example 237 for an illustrative example).

| Example | Starting 11-Substituted Prostaglandin-E | Method of Example | Product 11-Substituted Prostaglandin F |
|---|---|---|---|
| 238 | 11-deoxyprostaglandin methyl ester (Ex. 46) | 81 | 11-deoxyprostaglandin F$_{2\alpha}$ |
| 239 | 11-deoxy-11$\alpha$-vinylprostaglandin E$_2$ methyl ester (Ex. 28a) | 81 | 11-deoxy-11$\alpha$-vinylprostaglandin F$_{2\alpha}$ |
| 240 | 11-deoxy-11$\alpha$-hydroxymethylprostaglandin-E$_2$ (Ex. 83) | 80 | 11-deoxy-11$\alpha$-hydroxymethylprostaglandin-F$_{2\alpha}$ |
| 241 | 11-deoxy-11$\alpha$-hydroxymethylprostaglandin-E$_2$ (Ex. 184) | 80 | 11-deoxy-11$\alpha$-hydroxymethylprostaglandin-F$_{2\alpha}$ |
| 242 | 11$\alpha$-acetylthio-11-deoxyprostaglandin-E$_2$ (Ex. 14) | 80 | 11$\alpha$-acetylthio-11-deoxyprostaglandin-F$_{2\alpha}$ |
| 243 | 11-deoxy-11$\alpha$-ethylprostaglandin-E$_2$ methyl ester (Ex. 20) | 81 | 11-deoxy-11$\alpha$-ethylprostaglandin-F$_{2\alpha}$ |
| 244 | 11-deoxy-11,15-bisdeoxy-11,15-dimethylprostaglandin-E$_2$ (Ex. 17) | 81 | 11,15-bisdeoxy-11,15-dimethylprostaglandin-F$_{2\alpha}$ |
| 245 | 11-deoxy-11$\alpha$-(1-hydroxy-1-methylethyl)prostaglandin-E$_2$ (Ex. 184A) | 80 | 11-deoxy-11$\alpha$-(1-hydroxy-1-methylethyl)prostaglandin-F$_{2\alpha}$ |

| Example | Starting 11$\alpha$-alkylthio-11-deoxyprostaglandin E | Method of Example | Product 11$\alpha$-alkylthio-11-deoxyprostaglandin F |
|---|---|---|---|
| 246 | l-11-deoxy-11$\alpha$-ethylthioprostaglandin-E$_3$ (Ex. 115) | 80 | l-11-deoxy-11$\alpha$-ethylthioprostaglandin-F$_{3\alpha}$ |
| 247 | l-11-deoxy-11$\alpha$-methylthio-15-epi-prostaglandin-E$_2$ (Ex. 116) | 80 | l-11-deoxy-11$\alpha$-methylthio-15-epi-prostaglandin-F$_{2\alpha}$ |
| 248 | l-11-deoxy-11$\alpha$-(1-propylthio)-15-epi-O-acetyl-prostaglandin-E$_2$ methyl ester (Ex. 117) | 81 | l-11-deoxy-11$\alpha$-(propylthio)-15-epi-O-acetyl-prostaglandin-F$_{2\alpha}$methyl ester |
| 249 | dl-11-deoxy-11$\alpha$-butylthio-prostaglandin-E$_1$ (Ex. 118) | 80 | dl-11-deoxy-11$\alpha$-butylthioprostaglandin-F$_{1\alpha}$ |
| 250 | l-11-deoxy-11$\alpha$-methylthio-prostaglandin-E$_1$ methyl ester (Ex. 119) | 81 | l-11-deoxy-11$\alpha$-methylthioprostaglandin-F$_{1\alpha}$ methyl ester |
| 251 | l-11-deoxy-11$\alpha$-ethylthio-15-methylprostaglandin-E$_2$ methyl ester (Ex. 120) | 81 | l-11-deoxy-11$\alpha$-ethylthio-15-methylprostaglandin-F$_{2\alpha}$methyl ester |
| 252 | l-11-deoxy-11$\alpha$-propylthiol-16,16-dimethylprostaglandin-E$_2$ (Ex. 121) | 80 | l-11-deoxy-11$\alpha$-propylthiol-16,16-dimethylprostaglandin-F$_{2\alpha}$ |
| 253 | l-11-deoxy-11$\alpha$-ethylthio-16(S)-methylprostaglandin-E$_2$ (Ex. 122) | 80 | l-11-deoxy-11$\alpha$-ethylthio-16(S)-methylprostaglandin-F$_{2\alpha}$ |
| 254 | l-11-deoxy-11$\alpha$-methylthio-16,16-difluoroprostaglandin-E$_2$ (Ex. 123) | 80 | l-11-deoxy-11$\alpha$-methylthio-16,16-difluoroprostaglandin-F$_{2\alpha}$ |
| 255 | l-11-deoxy-11$\alpha$-methylthio-16-fluoroprostaglandin-E$_2$ (Ex. 124) | 80 | l-11-deoxy-11$\alpha$-methylthio-16-fluoroprostaglandin-F$_{2\alpha}$ |
| 256 | l-11-deoxy-11$\alpha$-methylthiol-20-ethylprostaglandin-E$_2$ | 80 | l-11-deoxy-11$\alpha$-methylthiol-20-ethylprostaglandin-F$_{2\alpha}$ |

| Example | (continued) | | |
|---|---|---|---|
| 257 | dl-11-deoxy-11α-ethylthio-17,20-tetranor-16-p-fluorophenoxyprostaglandin-$E_2$ (Ex. 126) | 80 | dl-11-deoxy-11α-ethylthio-17,20-tetranor-16-p-fluorophenoxyprostaglandin-$F_{2α}$ |
| 258 | dl-11-deoxy-11α-methylthio-17,20-tetranor-16-m-trifluoromethylphenoxyprostaglandin-$E_2$ (Ex. 127) | 80 | dl-11-deoxy-11α-methylthio-17,20-tetranor-16-m-trifluoromethylphenoxyprostaglandin-$F_{2α}$ |
| 259 | l-11-deoxy-11α-butylthio-17,20-tetranor-16-m-trifluoromethylphenoxyprostaglandin-$E_2$ (Ex. 128) | 80 | l-11-deoxy-11α-butylthio-17,20-tetranor-16-m-trifluoromethylphenoxyprostaglandin-$F_{2α}$ |
| 260 | l-11-deoxy-11α-methylthio-17,20-tetranor-16-m-chlorophenoxyprostaglandin-$E_2$ (Ex. 129) | 80 | l-11-deoxy-11α-methylthio-17,20-tetranor-16-m-chlorophenoxyprostaglandin-$F_{2α}$ |

| Example | Starting 11-Substituted-11-deoxyprostaglandin E | Method of Example | Product 11-Substituted-11-deoxyprostaglandin F |
|---|---|---|---|
| 261 | l-11-deoxy-11α-methylprostaglandin-$E_3$ (Ex. 130) | 80 | l-11-deoxy-11α-methylprostaglandin-$F_{3α}$ |
| 262 | l-11-deoxy-11α-methylprostaglandin-$E_2$ methyl ester (Ex. 131) | 81 | l-11-deoxy-11α-methylprostaglandin-$F_{2α}$ methyl ester |
| 263 | l-11-deoxy-11α-ethyl-15-epi-prostaglandin-$E_2$ (Ex. 132) | 80 | l-11-deoxy-11α-ethyl-15-epi-prostaglandin-$F_{2α}$ |
| 264 | dl-11-deoxy-11α-phenylprostaglandin $E_2$ and dl-11-deoxy-11-phenylprostaglandin-$E_2$ methyl ester (Ex. 133) | 81 | dl-11-deoxy-11α-phenylprostaglandin-$E_{2α}$ and dl-11-deoxy-11α-phenylprostaglandin-$F_{2α}$ methyl ester |
| 265 | l-11-deoxy-11α-methyl-15-methyl-prostaglandin-$E_2$ methyl ester (Ex. 134) | 81 | l-11-deoxy-11α-methyl-15-methylprostaglandin-$F_{2α}$ methyl ester |
| 266 | l-11-deoxy-11α-methyl-16,16-dimethylprostaglandin-$E_1$ methyl ester (Ex. 135) | 81 | l-11-deoxy-11α-methyl-16,16-dimethylprostaglandin-$F_{1α}$ methyl ester |
| 267 | l-11-deoxy-11α-vinyl-16(S)-methylprostaglandin-$E_2$ (Ex. 136) | 80 | l-11-deoxy-11α-vinyl-16(S)-methylprostaglandin-$F_{2α}$ |

| Example | Starting 11-Substituted-11-deoxyprostaglandin-E | Method of Example | Product 11-Substituted-11-deoxyprostaglandin F |
|---|---|---|---|
| 268 | l-11-deoxy-11α-(1-butenyl)-16-fluoroprostaglandin-$E_2$ (Ex. 137) | 80 | l-11-deoxy-11α-(1-butenyl)-16-fluoroprostaglandin-$F_{2α}$ |
| 269 | l-11-deoxy-11α-propenyl-20-ethylprostaglandin-$E_2$ (Ex. 138) | 80 | l-11-deoxy-11α-propenyl-20-ethylprostaglandin-$F_{2α}$ |
| 270 | l-11-deoxy-11α-methyl-17,20-tetranor-16-m-trifluoromethylphenylprostaglandin-$E_2$ (Ex. 139) | 80 | l-11-deoxy-11α-methyl-17,20-tetranor-16-m-trifluoromethylphenylprostaglandin-$F_{2α}$ |
| 271 | l-11-deoxy-11α-methyl-17,20-tetranor-16-m-chlorophenoxyprostaglandin-$E_2$ (Ex. 140) | 80 | l-11-deoxy-11α-methyl-17,20-tetranor-16-m-chlorophenoxyprostaglandin-$F_{2α}$ |
| 271A | l-11-deoxy-11α-vinyl-17,20-tetranor-16-m-trifluoromethylphenoxyprostaglandin-$E_2$ (Ex. 140A) | 80 | l-11-deoxy-11α-vinyl-17,20-tetranor-16-m-trifluoromethylphenoxyprostaglandin-$F_{2α}$ |
| 271B | l-11-deoxy-11α-vinyl-17,20-tetranor-16-m-chlorophenoxyprostaglandin-$E_2$ (Ex. 140B) | 80 | l-11-deoxy-11α-vinyl-17,20-tetranor-16-m-chlorophenoxyprostaglandin-$F_{2α}$ |
| 271C | l-11-deoxy-11α-vinyl-17,20-tetranor-16-p-fluorophenoxyprostaglandin-$E_2$ (Ex. 140C) | 80 | l-11-deoxy-11α-vinyl-17,20-tetranor-16-p-fluorophenoxyprostaglandin-$F_{2α}$ |
| 271D | l-11-deoxy-11α-vinyl-16,16-dimethylprostaglandin-$E_2$ (Ex. 140D) | 80 | l-11-deoxy-11α-vinyl-16,16-dimethylprostaglandin-$F_{2α}$ |

| Example | Starting 13,14-dihydro-prostaglandin $E_1$ | Method of Example | Product 13,14-dihydroprostaglandin $F_{1α}$ |
|---|---|---|---|
| 272 | l-11-deoxy-11α-methyl-13,14-dihydro-15-methyl-prosta- | 81 | l-11-deoxy-11α-methyl-13,14-dihydro-15-methyl-prostaglandin-$F_{1α}$ methyl ester |
| 273 | l-11-deoxy-11α-ethyl-15-epi-13,14-dihydroprostaglandin-$E_1$ (Ex. 142) | 80 | l-11-deoxy-11α-ethyl-15-epi-13,14-dihydroprostaglandin-$F_{1α}$ |
| 274 | l-11-deoxy-11α-methyl-13,14-dihydro-16,16-dimethyl- | 81 | l-11-deoxy-11α-methyl-13,14-dihydro-16,16-dimethylprostaglandin-$F_{1α}$ methyl ester |

-continued

| | | | |
|---|---|---|---|
| 275 | prostaglandin-$E_1$ methyl ester (Ex. 143) l-11-deoxy-11α-phenyl-13,14-di-hydroprostaglandin-$E_1$ methyl ester (Ex. 144) | 81 | l-11-deoxy-11α-phenyl-13,14-dihydroprostaglandin-$F_{1α}$methyl ester |
| 276 | l-11-deoxy-11α-methyl-13,14-dihydro-17,20-tetranor-16-m-trifluoromethylphenoxy-prostaglandin-$E_1$ | 80 | l-11-deoxy-11α-methyl-13,14-dihydro-17,20-tetranor-16-m-trifluoromethylphenoxyprostaglandin-$F_{1α}$ |

| Example | 11α/β-cyano-11-deoxy-prostaglandin E | Method of Example | Product 11α/β-cyano-11-deoxyprostaglandin F |
|---|---|---|---|
| 277 | l-11-deoxy-11α-cyanoprostaglandin-$E_3$ and l-11-deoxy-11β-cyanoprostaglandin-$E_3$ (Ex. 158) | 80 | l-11-deoxy-11α-cyanoprostaglandin-$F_{3α}$ and l-11-deoxy-11β-cyanoprostaglandin-$F_{3β}$ |
| 278 | dl-11-deoxy-11α-cyanoprostaglandin-$E_2$ and dl-11-deoxy-11β-cyanoprostaglandin-$E_2$ (Ex. 159) | 80 | dl-11-deoxy-11α-cyanoprostaglandin-$F_{2α}$ and dl-11-deoxy-11β-cyanoprostaglandin-$F_{2β}$ |
| 279 | l-11-deoxy-11α-cyano-15-methylprostaglandin-$E_2$ and l-11-deoxy-11β-cyano-15-methylprostaglandin-$E_2$ methyl esters (Ex. 160) | 81 | l-11-deoxy-11α-cyano-15-methylprostaglandin-$F_{2α}$ and l-11-deoxy-11β-cyano-15-methylprostaglandin-$F_{2β}$ methyl esters |
| 280 | l-11-deoxy-11α-cyano-16,16-dimethylprostaglandin-$E_2$ and l-11-dioxy-11β-cyano-16,16-dimethylprostaglandin-$E_2$ (Ex. 161) | 80 | l-11-deoxy-11α-cyano-16,16-dimethylprostaglandin-$F_{2β}$ and l-11-deoxy-11β-cyano-16,16-dimethylprostaglandin-$F_{2α}$ |
| 281 | l-11-deoxy-11α-cyano-16(S)-methylprostaglandin-$E_2$ and l-11-deoxy-11β-cyano-16(S)-methylprostaglandin-$E_2$ (Ex. 162) | 80 | l-11-deoxy-11α-cyano-16(S)-methylprostaglandin-$F_{2α}$ and l-11-deoxy-11β-cyano-16(S)-methyl prostaglandin-$F_{2β}$ |

| Example | Starting 11α/β-cyano-11-deoxyprostaglandin-E | Method of Example | Product 11α/β-cyano-11-deoxyprostaglandin F |
|---|---|---|---|
| 282 | l-11-deoxy-11α-cyano-16,16-difluoroprostaglandin-$E_2$ and l-11-deoxy-11β-cyano-16,16-difluoroprostaglandin-$E_2$ (Ex. 163) | 80 | l-11-deoxy-11α-cyano-16,16-difluoroprostaglandin-$F_{2α}$ and l-11-deoxy-11β-cyano-16,16-difluoroprostaglandin-$F_{2α}$ |
| 283 | l-11-deoxy-11α-cyano-16-fluoroprostaglandin-$E_2$ and d-11-deoxy-11β-cyano-16-Fluoroprostaglandin-$E_2$ (Ex. 164) | 80 | l-11-deoxy-11α-cyano-16-fluoroprostaglandin-$F_{2α}$ and d-11-deoxy-11β-cyano-16-fluoroprostaglandin-$F_{2α}$ |
| 284 | dl-11-deoxy-11α-cyano-17,20-tetranor-16-p-fluorophenoxyprostaglandin-$E_2$ and dl-11-deoxy-11β-cyano-17,20-tetranor-16-p-fluorophenoxyprostaglandin-$E_2$ (Ex. 165) | 80 | di-11-deoxy-11α-cyano-17,20-tetranor-16-p-fluorophenoxyprostaglandin-$F_{2α}$ and dl-11-deoxy-11β-cyano-17,20-tetranor-16-p-fluorophenoxyprostaglandin-$F_{2α}$ |
| 285 | l-11-deoxy-11α-cyano-17,20-tetranor-16-m-trifluoromethylphenoxyprostaglandin-$E_2$ and l-11-deoxy-11β-cyano-17,20-tetranor-16-m-trifluoromethylphenoxyprostaglandin-$E_2$ (Ex. 166) | 80 | l-11-deoxy-11α-cyano-17,20-tetranor-16-m-trifluoromethylphenoxyprostaglandin-$F_{2α}$ and l-11-deoxy-11β-cyano-17,20-tetranor-16-m-trifluoromethylphenoxyprostaglandin-$F_{2α}$ |

| Example | Starting 11α/β-cyano-11-deoxyprostaglandin E | Method of Example | Product 11α/β-cyano-11-deoxyprostaglandin F |
|---|---|---|---|
| 286 | l-11-deoxy-11α-cyano-17,20-tetranor-16-m-chlorophenoxyprostaglandin-$E_2$ and l-11-deoxy-11β-cyano-17,20-tetranor-16-m-chlorophenoxyprostaglandin-$E_2$(Ex. 167) | 80 | l-11-deoxy-11α-cyano-17,20-tetranor-16-m-chlorophenoxyprostaglandin-$F_{2α}$ and l-11-deoxy-11-cyano-17,20-tetranor-16-m-chlorophenoxyprostaglandin-$F_{2β}$ |

| Example | Starting 11-Substituted-11-deoxy-prostaglandin E | Method of Example | Product 11-Substituted-11-deoxyprostaglandin F |
|---|---|---|---|
| 287 | dl-11-deoxy-11α-hydroxyprostaglandin-$E_2$; dl-11-deoxy-11β-hydroxymethylprostaglandin-$E_2$ (Ex. 174) | 80 | dl-11-deoxy-11α-hydroxymethylprostaglandin-$F_{2α}$ dl-11-deoxy-11β-hydroxymethylprostaglandin-$F_{2α}$ and dl-8-iso-11α-hydroxymethylprostaglandin-$F_{2α}$ |
| 288 | l-11-deoxy-11α-hydroxymethyl-15-methylprostaglandin-$E_2$ methyl ester; l-11-deoxy-11β-hydroxymethyl-15-methylprostaglandin-$E_2$ and 8-iso-11-deoxy-11α- | 81 | l-11-deoxy-11α-hydroxymethyl-15-methylprostaglandin-$F_{2α}$ methyl ester; l-11-deoxy-11β-hydroxymethyl-15-methylprostaglandia-$F_{2α}$ and 8-iso-11-deoxy-11α-hydroxymethyl-15-methyl-prostaglandins-$F_{2α}$ methyl ester |

-continued

| Example | | Method | |
|---|---|---|---|
| 289 | hydroxymethyl-15-methylprosta-glandins-E$_2$ methyl ester (Ex. 175) l-11-deoxy-11α-(1-hydroxy-methyl)-16,16-dimethylprosta-glandin-E$_1$; l-11-deoxy-11β-(1-hydroxymethyl)-16,16-dl-methylprostaglandin-E$_1$ and 8-oxo-11-deoxy-11α-(hydroxy-methyl)-16,16-dimethylprosta-glandin-E$_1$ (Ex. 176) | 80 | l-11-deoxy-11α-(1-hydroxymethyl)-16,16-dimethyl-prostaglandin-F$_{1α}$; l-11-deoxy-11α-(1-hydroxy-methyl)-16,16-dimethylprostaglandin-F$_{1α}$ and 8-iso-11-deoxy-11α-(hydroxymethyl)-16,16-dl-methylprostaglandin-F$_{1α}$ |

| Example | Starting 11-substituted-11-deoxyprostaglandin E | Method of Example | Product 11-Substituted-11-deoxyprostaglandin F |
|---|---|---|---|
| 290 | l-11-deoxy-11α-hydroxy-methyl-16(R)-methylprosta-glandin-E$_2$; l-11-deoxy-11β-hydroxymethyl-16(R)-methylprostaglandin-E$_2$ and dl-8-iso-11α-hydroxymethyl-prostaglandin-E$_2$ (Ex. 177) | 80 | l-11-deoxy-11α-hydroxymethyl-16(R)-methylprosta-glandin-F$_2$; l-11-deoxy-11β-hydroxymethyl-16(R)-methylprostaglandin-F$_{2α}$ and 8-iso-11-deoxy-11α-hydroxymethyl-16(R)-methylprostaglandin-F$_{2α}$ |
| 291 | l-11-deoxy-11α-hydroxy-methyl-16,16-difluoro-prostaglandin-E$_2$; l-11-deoxy-11β-hydroxymethyl-16,16-difluoroprosta-glandin-E$_2$ and 8-iso-11-deoxy-11β-hydroxymethyl-16,16-difluoroprosta-glandin-E$_2$ (Ex. 178) | 80 | l-11-deoxy-11α-hydroxymethyl-16,16-difluoro-prostaglandin-F$_{2α}$; l-11-deoxy-11β-hydroxy-methyl-16,16-difluoroprostaglandin-F$_2$ and 8-iso-11-deoxy-11α-hydroxymethyl-16,16-difluoro-prostaglandin-F$_{2α}$ |

| Example | Starting prostaglandin E | Method of Example | Product Prostaglandin Fα |
|---|---|---|---|
| 292 | l-11-deoxy-11α-(1-hydroxy-ethyl)-13-dihydroprosta-glandin-E$_1$ and 11-deoxy-11α-(1-hydroxymethyl)-13-di-hydroprostaglandin-E$_1$ and 8-iso-11-deoxy-11α-(1-hydroxyethyl)-13-dihydro-prostaglandin-E$_1$(Ex. 169) | 80 | l-11-deoxy-11α-(1-hydroxyethyl)-13-dihydro-prostaglandin-F$_{1α}$ and 11-deoxy-11α-(1-hydroxy-ethyl)-13-dihydroprostaglandin-F$_{1α}$ and 8-iso-(1-hydroxyethyl)-13-dihydro-prostaglandin-F$_1$ |
| 293 | l-11-deoxy-11α-(1-hydroxy-1-methylethyl)prostaglandin-E$_1$ (Ex. 170) | 80 | l-11-dioxy-11α-(1-hydroxy-1-methylethyl)-prostaglandin-F$_{1α}$ |
| 294 | l-11-deoxy-11α-hydroxy-methyl-prostaglandin-E$_3$ and l-11-deoxy-11α-hydroxy-methylprostaglandin-E$_2$ and 8-iso-11-deoxy-11α-hydroxy-methylprostaglandin-E$_3$ (Ex. 171) | 80 | l-11-deoxy-11α-hydroxymethyl-prostaglandin-F$_{3α}$ and l-11-deoxy-11α-hydroxymethylprostaglandin-F$_{3α}$ and 8-iso-11-deoxy-11α-hydroxymethylprosta-glandin-F$_{3α}$ |
| 295 | l-11-deoxy-11α-hydroxy-methyl-15-epiprostaglandin-E$_2$ and l-11-deoxy-11α-hy-droxymethyl-15-epiprosta-glandin-E$_2$ and 8-iso-11-deoxy-11α-hydroxymethyl-15-epiprostaglandin-E$_2$ (Ex. 172) | 80 | l-11-deoxy-11α-hydroxymethyl-15-epiprosta-glandin-F$_{2α}$ and l-11-deoxy-11α-hydroxymethyl-15-epiprostaglandin-F$_{2α}$ and 8-iso-11-deoxy-11α hydroxymethyl-15-epiprostaglandin-F$_{2α}$ |
| 296 | l-11-deoxy-11α-(1-hydroxy-1-methylethylacetylprosta-glandin-E$_2$ methyl ester (Ex. 173) | 81 | l-11-deoxy-11α-(1-hydroxy-1-methylethylacetyl-prostaglandin-F$_{2α}$ methyl ester |
| 297 | l-11-deoxy-11α-hydroxy-methyl-20-ethylprostaglandin-E$_2$; l-11-deoxy-11β-hydroxy-methyl-20-ethylprostaglandin-E$_2$ and 8-iso-11-deoxy-11α-hydroxymethyl-20-ethyl-prostaglandin-E$_2$ (Ex. 179) | 80 | l-11-deoxy-11α-hydroxymethyl-20-ethylprosta-glandin-F$_2$; l-11-deoxy-11β-hydroxymethyl-20-ethylprostglandin-F$_{2α}$ and 8-iso-11-deoxy-11α-hydroxymethyl-20-ethylprostaglandin-F$_{2α}$ |
| 298 | dl-11-deoxy-11α-hydroxy-methyl-17,20-tetranor-16-m-trifluoromethylphenoxy-prostaglandin-E$_2$; dl-11-deoxy-11β-hydroxymethyl-17,20-tetranor-16-m-tri-fluoromethylphenoxyprosta-glandin-E$_2$ and dl-8-iso-11-deoxy-11α-hydroxymethyl-17,20-tetranor-16-m-tri-fluoromethylprostaglandin-E$_2$ (Ex. 180) | 80 | dl-11-deoxy-11α-hydroxymethyl-17,20-tetranor-16-m-trifluoromethylphenoxyprostaglandin-F$_{2α}$; dl-11-deoxy-11β-hydroxymethyl-17,20-tetranor-16-m-trifluoromethylphenoxyprosta-glandin-F$_{2α}$ and dl-8-iso-11-deoxy-11α-hydroxy-methyl-17,20-tetranor-16-m-trifluoromethyl-prostaglandin-F$_{2α}$ |
| 299 | l-11-deoxy-11α-(-hydroxy-1- | 80 | l-11-deoxy-11α-(1-hydroxy-1-methylethyl)- |

-continued

| | | | |
|---|---|---|---|
| | methylethyl)-17,20-tetranor-16-p-fluorophenoxyprostaglandin-E$_2$ (Ex. 181) | | 17,20-tetranor-16-p-fluorophenoxyprostaglandin-F$_2$ |
| 300 | l-11-deoxy-11α-hydroxymethyl-17,20-tetranor-16-m-chlorophenoxyprostaglandin-E$_2$; l-11-deoxy-11β-hydroxymethyl-17,20-tetranor-16-m-chlorochlorophenoxyprostaglandin-E$_2$ and l-8-iso-11-deoxy-11α-hydroxymethyl-17,20-tetranor-16-m-chlorophenoxyprostaglandin-E$_2$ | 80 | l-11-deoxy-11α-hydroxymethyl-17,20-tetranor-16-m-chlorophenoxyprostaglandin-F$_{2α}$; l-11-11β-hydroxymethyl-17,20-tetranor-16-m-chlorophenoxyprostaglandin-F$_{2α}$ and l-8-iso-11-deoxy-11α-hydroxymethyl-17,20-tetranor-16-m-chlorophenoxyprostaglandin-F$_{2α}$ |
| 301 | l-11-deoxy-11α-(1,3-dioxoan-2-yl)-1,3-dihydroprostaglandin-E$_1$ (Ex. 186) | 80 | l-11-deoxy-11α-(1,3-dioxolan-2-yl)-13-dihyroprostaglandin-F$_{1α}$ |
| 302 | l-11-deoxy-11α-(2-methyl-1,3-dioxolan-2-yl)prostaglandin-E$_1$ (Ex. 187) | 80 | l-11-deoxy-11α-(2-methyl-1,3-dioxolan-2-yl)-prostaglandin-F$_{1α}$ |
| 303 | l-11-deoxy-11α-(1,3-dioxolan-2-yl)-prostaglandin-E$_3$ | 80 | l-11-deoxy-11α-(1,3-dioxolan-2-yl)-prostaglandin-F$_{3α}$ |
| 304 | l-11-deoxy-11α-(1,3-dioxolan-2-yl)-15-epi-prostaglandin-E$_2$ (Ex. 189) | 80 | l-11-deoxy-11α-(1,3-dioxolan-2-yl)-15-epi-prostaglandin-F$_{2α}$ |
| 305 | dl-11-deoxy-11α-(1,3-dioxolan-2-yl)-prostaglandin-E$_2$ (Ex. 190) | 80 | dl-11-deoxy-11α-(1,3-dioxolan-2-yl)-prostaglandin-F$_{2α}$ |
| 306 | l-11-deoxy-11α-(1,3-dioxolan-2-yl)-15-methylprostaglandin-E$_1$ methylester (Ex. 191) | 81 | l-11-deoxy-11α-(1,3-dioxolan-2-yl)-15-methyl-prostaglandin-F$_{1α}$ methyl ester |
| 307 | l-11-deoxy-11α-(2-methyl-1,3-dioxolan-2-yl)-16,16-dimethylprostaglandin-E$_2$ | 80 | l-11-deoxy-11α-(2-methyl-1,3-dioxolan-2-yl)-16,16-dimethylprostaglandin-F$_{2α}$ |
| 308 | l-11-deoxy-11α-(1,3-dioxolan-2-yl)-16(R)-methylprostaglandin-E$_2$ (Ex. 193) | 80 | l-11-deoxy-11α-(1,3-dioxolan-2-yl)-16-(R)methyl-prostaglandin-F$_{2α}$ |
| 309 | l-11-deoxy-11α-(1,3-dioxolan-2-yl)-16,16-difluoroprostaglandin-E$_2$ (Ex. 194) | 80 | l-11-deoxy-11α-(1,3-dioxolan-2-yl)-16,16-difluoroprostaglandin-F$_{2α}$ |
| 310 | l-11-deoxy-11α-(1,3-dioxolan-2-yl)-20-ethylprostaglandin-E$_2$ (Ex. 195) | 80 | l-11-deoxy-11α-(1,3-dioxolan-2-yl)-20-ethyl-prostaglandin-F$_{2α}$ |
| 311 | dl-11-deoxy-11α-(1,3-dioxolan-2-yl)-17,20-tetranor-16-m-trifluoromethylphenoxyprostaglandin-E$_2$ (Ex. 196) | 80 | dl-11-deoxy-11α-(1,3-dioxolan-2-yl)-17,20-tetranor-16-m-trifluoromethylphenoxyprostaglandin-F$_{2α}$ |
| 312 | l-11-deoxy-11α-(1,3-dioxolan-2-yl)-17,20-tetranor-16-p-fluorophenoxyprostaglandin-E$_2$ (Ex. 197) | 80 | l-11-deoxy-11α-(1,3-dioxolan-2-yl)-17,20-tetranor-16-p-fluorophenoxyprostaglandin-F$_{2α}$ |
| 313 | l-11-deoxy-11α-(1,3-dioxolan-2-yl)-17,20-tetranor-16-m-chlorophenoxyprostaglandin-F$_2$ (Ex. 198) | 80 | l-11-deoxy-11α-(1,3-dioxolan-2-yl)-17,20-tetranor-16-m-chlorophenoxyprostaglandin-F$_{2α}$ |

| Example | Starting 11-deoxy-11α/β-alkanoylthioprostaglandin E | Method of Example | Product 11-deoxy-11α/β-mercaptoprostaglandin E |
|---|---|---|---|
| 314 | l-11-deoxy-11α-propanoylthio-13-dihydroprostaglandin-F$_1$ and 11-deoxy-11β-propanoylthio-13-dihydroprostaglandin-E$_1$ (Ex. 223) | 80 | l-11-deoxy-11α-mercapto-13-dihydroprostaglandin-F$_{1α}$ and 11-deoxy-11β-propanoylthiol-13-didihydroprostaglandin-F$_{1α}$ |
| 315 | l-11-deoxy-11α-acetylthioprostaglandin-E$_3$ and l-11-deoxy-11β-acetylthioprostaglandin-E$_3$ (Ex. 224) | 80 | l-11-deoxy-11α-mercaptoprostaglandin-F$_{2α}$ and l-11-deoxy-11β-mercaptoprostaglandin-F$_{3α}$ |
| 316 | l-11-deoxy-11α-acetylthio-prostaglandin-E$_2$ methyl ester and l-11-deoxy-11β-acetylthio-prostaglandin-E$_2$ methyl ester (Ex. 225) | 80 | l-11-deoxy-11α-mercaptoprostaglandin-F$_{2α}$ methyl ester and l-11-deoxy-11β-mercaptoprostaglandin-F$_{2α}$ methyl ester |
| 317 | l-11-deoxy-11α-acetylthio-15-epi-prostaglandin-E$_2$ and l-11-deoxy-11β-acetylthio-15-epiprostaglandin-E$_2$ (Ex. 226) | 80 | l-11-deoxy-11α-mercaptoprostaglandin-15-epi-prostaglandin-F$_{2α}$ and l-11-deoxy-11β-mercapto-15-epiprostaglandin-F$_{2α}$ |
| 318 | dl-11-deoxy-11α-acetylthio-prostaglandin-E$_1$ and dl-11-deoxy-11β-acetylthiol-prostaglandin-E$_1$ (Ex. 227) | 80 | dl-11-deoxy-11α-mercaptoprostaglandin-E$_{1α}$ and dl-11-deoxy-11β-mercaptoprostaglandin-F$_{1α}$ |
| 319 | l-11-deoxy-11α-acetylthio- | 80 | l-11-deoxy-11α-mercapto-16,16-dimethylprosta- |

-continued

| | | | |
|---|---|---|---|
| | 16,16-dimethylprostaglandin-E$_1$ and l-11-deoxy-11β-acetylthio-16,16-dimethylprostaglandin-E$_1$ (Ex. 228) | | glandin-F$_{1α}$ and l-11-deoxy-11β-mercapto-16,16-dimethylprostaglandin-F$_{1α}$ |
| 320 | l-11-deoxy-11α-acetylthio-16,16-dimethylprostaglandin-E$_2$ and l-11-deoxy-11β-acetylthio-16,16-dimethylprostaglandin-E$_2$ (Ex. 229) | 80 | l-11-deoxy-11α-mercapto-16,16-dimethylprostaglandin-F$_{2α}$ and l-11-deoxy-11β-mercapto-16,16-dimethylprostaglandin-F$_{2α}$ |
| 321 | l-11-deoxy-11α-acetylthiol-16(S)methylprostaglandin-E$_2$ and l-11-deoxy-11β-acetylthio-16(S)-methylprostaglandin-E$_2$ (Ex. 230) | 80 | l-11-deoxy-11α-mercapto-16,16(S)-methylprostaglandin-F$_{2α}$ and l-11-deoxy-11β-mercapto-16(S)-methylprostaglandin-F$_{2α}$ |
| 322 | l-11-deoxy-11α-acetylthio-16-fluoroprostaglandin-E$_2$ and l-11-deoxy-11β-acetylthio-16-fluoroprostaglandin-E$_2$ (Ex. 231) | 80 | l-11-deoxy-11α-mercapto-16-fluoroprostaglandin-F$_{2α}$ and l-11-deoxy-11β-mercapto-16-fluoroprostaglandin-F$_{2α}$ |
| 323 | l-11-deoxy-11α-acetylthio-20-methylprostaglandin-E$_2$ and l-11-deoxy-11β-acetylthiol-20-methylprostaglandin-E$_2$ (Ex. 232) | 80 | l-11-deoxy-11α-mercapto-20-methylprostaglandin-E$_{2α}$ and l-11-deoxy-11β-mercapto-20-methylprostaglandin-F$_{2α}$ |
| 324 | dl-11-deoxy-11α-acetylthio-17,20-tetranor-16-m-trifluoromethylphenoxyprostaglandin-E$_2$ and dl-11-deoxy-11β-acetylthiol-17,20-tetranor-16-m-trifluoromethylphenoxyprostaglandin-E$_2$ (Ex. 233) | 80 | dl-11-deoxy-11α-mercapto-17,20-tetranor-16-m-trifluoromethylphenoxyprostaglandin-E$_2$ and dl-11-deoxy-11β-mercapto-17,20-tetranor-16-m-trifluoromethylphenoxyprostaglandin-E$_2$ trifluoromethylphenoxyprostaglandin-E$_2$ |
| 325 | l-11-deoxy-11α-acetylthio-17,20-tetranor-16-p-fluorophenoxyprostaglandin-E$_2$ and l-11-deoxy-11β-acetylthiol-17,20-tetranor-16-p-fluorophenoxyprostaglandin-E$_2$ (Ex. 234) | 80 | l-11-deoxy-11α-mercapto-17,20-tetranor-16-p-fluorophenoxyprostaglandin-F$_{2α}$ and l,-11-deoxy-11β-mercapto-17,20-tetranor-16-p-fluorophenoxyprostaglandin-F$_{2α}$ |
| 326 | l-11-deoxy-11α-acetylthio-17,20-tetranor-16-m-chlorophenoxyprostaglandin-E$_2$ and l-11-deoxy-11β-acetylthio-17,20-tetranor-16-m-chlorophenoxyprostaglandin-E$_2$ (Ex. 235) | 80 | l-11-deoxy-11α-mercapto-17,20-tetranor-16-m-chlorophenoxyprostaglandin-F$_{2α}$ and l-11-deoxy-11β-mercapto-17,20-tetranor-16-m-chlorophenoxyprostaglandin-F$_{2α}$ |

EXAMPLES 327–343

Hydrolysis of the starting prostaglandins of the table below by the method of Example 217 is productive of the product prostaglandins of the table.

| Example | Starting Prostaglandin | Product |
|---|---|---|
| 327 | l-11-deoxy-11α-(1,3-dioxolan-2-yl)-13-dihydroprostaglandin-F$_{1α}$ (Ex. 301) | l-11-deoxy-11α-(formyl)-13-dihydroprostaglandin-E$_{1α}$ |
| 328 | l-11-deoxy-11α-(2-methyl-1,3-dioxolan-2-yl)-prostaglandin-F$_{1α}$ (Ex. 302) | l-11-deoxy-11α-(acetyl)-prostaglandin-F$_{1α}$ |
| 329 | l-11-deoxy-11α-(1,3-dioxolan-2-yl)-prostaglandin-F$_{3α}$ (Ex. 303) | l-11-deoxy-11α-(formyl)-prostaglandin-F$_{3α}$ |
| 330 | l-11-deoxy-11α-(1,3-dioxolan-2-yl)-15-epi-prostaglandin-F$_{2α}$ (Ex. 304) | l-11-deoxy-11α-(formyl)-15-epi-prostaglandin-F$_{2α}$ |
| 331 | dl-11-deoxy-11α-(1,3-dioxolan-2-yl)-prostaglandin-F$_{2α}$ (Ex. 305) | dl-11-deoxy-11α-(formyl)-prostaglandin-F$_{2α}$ |
| 332 | l-11-deoxy-11α-(1,3-dioxolan-2-yl)-15-methylprostaglandin-F$_{1α}$ methyl ester (Ex. 306) | l-11-deoxy-11α-(formyl)-15-methylprostaglandin-F$_{1α}$ methyl ester |
| 333 | l-11-deoxy-11α-(2-methyl-1,3-dioxolan-2-yl)-16,16-dimethylprostaglandin-F$_{2α}$ (Ex. 307) | l-11-deoxy-11α-(acetyl)-16,16-dimethylprostaglandin-F$_{2α}$ |
| 334 | l-11-deoxy-11α-(1,3-dioxolan-2-yl)-16(R)-methylprostaglandin-F$_{2α}$ (Ex. 308) | l-11-deoxy-11α-(formyl)-16(R)-methylprostaglandin-F$_{2α}$ |
| 335 | l-11-deoxy-11α-(1,3-dioxolan-2-yl)-16,16-difluoroprostaglandin-F$_{2α}$ (Ex. 309) | l-11-deoxy-11α-(formyl)-16,16-difluoroprostaglandin-F$_{2α}$ |
| 336 | l-11-deoxy-11α-(1,3-dioxolan-2-yl)-20-ethylprostaglandin-F$_{2α}$ (Ex. 310) | l-11-deoxy-11α-(formyl)-20-ethylprostaglandin-F$_{2α}$ |
| 337 | dl-11-deoxy-11α-(1,3-dioxolan-2-yl)- | dl-11-deoxy-11α-(formyl)-17,20-tetranor-16-m- |

-continued

| | | |
|---|---|---|
| | 17,20-tetranor-16-m-trifluoromethyl-phenoxyprostaglandin-$F_{2\alpha}$ (Ex. 311) | trifluoromethylphenoxyprostaglandin-$F_{2\alpha}$ |
| 338 | 1-11-deoxy-11α-(1,3-dioxolan-2-yl)-17,20-tetranor-16-p-fluorophenoxy-prostaglandin-$F_{2\alpha}$ (Ex. 312) | 1-11-deoxy-11α-(formyl)-17,20-tetranor-16-p-fluorophenoxyprostaglandin-$F_{2\alpha}$ |
| 339 | 1-11-deoxy-11α-(1,3-dioxolan-2-yl)-17,20-tetranor-16-m-chlorophenoxy-prostaglandin-$F_{2\alpha}$ (Ex. 313) | 1-11-deoxy-11α-(formyl)-17,20-tetranor-16-m-chlorophenoxyprostaglandin-$F_{2\alpha}$ |
| 340 | 1-11-deoxy-11α-(1,3-dioxolan-2-yl)-prostaglandin-$F_{2\alpha}$ (Ex. 215) | 1-11-deoxy-11α-(formyl)-prostaglandin-$F_{2\alpha}$ |
| 341 | dl-11-deoxy-11α-(1,3-dioxolan-2-yl)-17,20-tetranor-16-p-fluoroprosta-glandin-$F_{2\alpha}$ (Ex. 216) | dl-11-deoxy-11α-(formyl)-17,20-tetranor-16-p-fluoroprostaglandin-$F_{2\alpha}$ |

| Example | Starting E Prostaglandins | Product F Prostaglandins |
|---|---|---|
| 342 | 1-11-deoxy-11β-(1,3-dioxolan-2-yl)-prostaglandin-$F_{2\alpha}$ and $F_{2\beta}$ (Ex. 210) | 1-11-deoxy-11β-(formyl)-prostaglandin-$F_{2\alpha}$ and $F_{2\beta}$ |
| 343 | 1-11-deoxy-11β-(1,3-dioxolano-2-yl)-17,20-tetranor-16-p-fluoroprosta-glandins-$F_{2\alpha}$ and $F_{2\beta}$ (Ex. 211) | 1-11-deoxy-11α-(formyl)-17,20-tetranor-16-p-fluoroprostaglandin-$F_{2\alpha}$ and $F_{2\beta}$ |

We claim:

1. A compound selected from the group consisting of an optically active compound of the formula

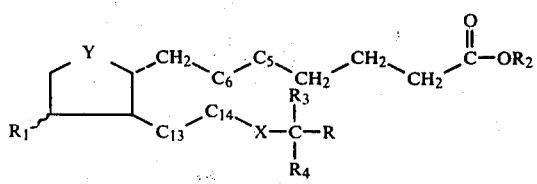

and a racemic compound of that formula and the mirror image thereof wherein R is phenyl, phenoxy or phenoxy substituted with one or more groups selected from the group consisting of lower alkyl, lower alkoxy, nitro, halo and trifluoromethyl; $R_1$ is selected from the group consisting of lower alkyl and lower 1-alkenyl; $R_2$ is selected from the group consisting of hydrogen and an alkyl group having from 1 to 12 carbon atoms; $R_3$ and $R_4$ are hydrogen; X is a divalent moiety selected from the group consisting of those of the formula

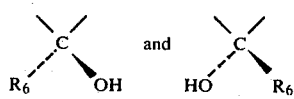

wherein $R_6$ is selected from the group consisting of hydrogen and lower alkyl; Y is a divalent moiety selected from the group consisting of those of the formula

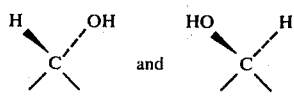

the moiety -$C_5$-$C_6$- is ethylene or cis vinylene and the moiety -$C_{13}$-$C_{14}$- is ethylene or trans vinylene with the proviso that when -$C_5$-$C_6$- is cis-vinylene then -$C_{13}$-$C_{14}$- must be trans-vinylene; and the non-toxic, cationic salts thereof when $R_2$ is hydrogen.

2. A compound according to claim 1 wherein R is phenoxy, and phenoxy substituted with one or more groups selected from the groups consisting of lower alkyl, lower alkoxy, nitro, halogen and trifluoromethyl.

3. A compound according to claim 2 wherein the moiety -$C_5$-$C_6$- is cis-vinylene and the moiety -$C_{13}$-$C_{14}$- is trans-vinylene.

4. A compound according to claim 3 wherein $R_1$ is a methyl or ethyl group or vinyl-moiety and Y is the divalent moiety

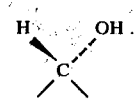

5. A compound according to claim 4 wherein $R_1$ is methyl.

6. A compound according to claim 2 wherein $R_1$ is methyl; $R_2$ is hydrogen; $R_3$ is hydrogen, $R_4$ is hydrogen; R is m-trifluoromethylphenoxy; -$C_5$-$C_6$- is ethylene; -$C_{13}$-$C_{14}$- is ethylene; X is

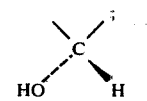

Y is

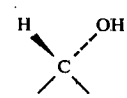

11-deoxy-11α-methyl-13,14-dihydro-17,20-tetranor-16-m-trifluoromethylphenoxy prostaglandin-$F_{1\alpha}$.

7. A compound according to claim 2 wherein $R_1$ is methyl; $R_2$ is hydrogen; $R_3$ is hydrogen; $R_4$ is hydrogen; R is n-trifluoromethylphenoxy; -$C_5$-$C_6$- is ethylene; X is

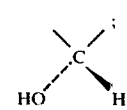

Y is

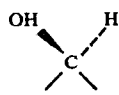

11-deoxy-11α-methyl-13,14-dihydro-17,20-tetranor-16-m-trifluoromethylphenoxy prostaglandin-$F_{1\beta}$.

8. The compound according to claim 3, 1-11-deoxy-11α-methyl-17,20-tetranor-16-m-chlorophenoxy-$F_{2\beta}$.

9. The compound according to claim 4, 1-11-deoxy-11α-vinyl-17,20-tetranor-16-m-trifluoromethylphenoxy-$F_{2\alpha}$.

10. The compound according to claim 4, 1-11-deoxy-11α-vinyl-17,20-tetranor-16-p-fluorophenoxy-$F_{2\alpha}$.

11. The optically active compound according to claim 4 wherein $R_1$ is α-vinyl; $R_2$ is hydrogen; $R_3$ is hydrogen; $R_4$ is hydrogen; R is m-chlorophenoxy; $C_{13}$-$C_{14}$ is trans-vinylene; $C_5$-$C_6$ is cis-vinylene; X is

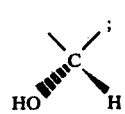

Y is

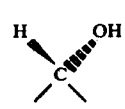

11α-vinyl-17-20-tetranor-16-m-chlorophenoxy-11-deoxyprostaglandin-$F_{2\alpha}$.

12. The optically active compound according to claim 5 wherein $R_1$ is α-methyl; $R_2$ is hydrogen; $R_3$ is hydrogen; $R_4$ is hydrogen; R is m-chlorophenoxy; $C_{13}$-$C_{14}$ is trans-vinylene; $C_5$-$C_6$ is cis-vinylene; X is

Y is

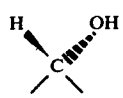

11α-methyl-16-m-chlorophenoxy-17,18,19,20-tetranor-11-deoxyprostaglandin-$F_{2\alpha}$.

13. The optically active compound according to claim 5 wherein $R_1$ is α-methyl; $R_2$ is hydrogen; $R_3$ is hydrogen; $R_4$ is hydrogen; R is m-trifluoromethylphenoxy; $C_{13}$-$C_{14}$ is trans-vinylene; $C_5$-$C_6$ is cis-vinylene; X is

Y is

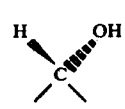

11α-methyl-16-m-trifluoromethylphenoxy-17,18,19,20-tetranor-11-deoxyprostaglandin-$F_{2\alpha}$.

* * * * *